US011723347B2

(12) United States Patent
Kaczorowski et al.

(10) Patent No.: US 11,723,347 B2
(45) Date of Patent: Aug. 15, 2023

(54) TRPC3 AS A THERAPEUTIC TARGET FOR ALZHEIMER'S DISEASE

(71) Applicant: The Jackson Laboratory, Bar Harbor, ME (US)

(72) Inventors: Catherine Kaczorowski, Bar Harbor, ME (US); Sarah M. Neuner, Bar Harbor, ME (US); Kristen M. S. O'Connell, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 505 days.

(21) Appl. No.: 16/688,435

(22) Filed: Nov. 19, 2019

(65) Prior Publication Data

US 2020/0154683 A1 May 21, 2020

Related U.S. Application Data

(60) Provisional application No. 62/770,095, filed on Nov. 20, 2018.

(51) Int. Cl.

| | |
|---|---|
| ***C12N 15/11*** | (2006.01) |
| ***A01K 67/027*** | (2006.01) |
| ***A61P 25/28*** | (2006.01) |
| ***C07K 14/705*** | (2006.01) |
| ***A61K 31/445*** | (2006.01) |
| ***C12N 15/113*** | (2010.01) |
| ***A61K 31/713*** | (2006.01) |

(52) U.S. Cl.

CPC ........ *A01K 67/0275* (2013.01); *A61K 31/445* (2013.01); *A61K 31/713* (2013.01); *A61P 25/28* (2018.01); *C07K 14/705* (2013.01); *C12N 15/1138* (2013.01); *A01K 2207/15* (2013.01); *A01K 2217/15* (2013.01); *A01K 2217/206* (2013.01); *A01K 2227/105* (2013.01); *A01K 2267/0318* (2013.01); *A01K 2267/0356* (2013.01); *C12N 2310/14* (2013.01)

(58) Field of Classification Search

CPC .............................. A61K 31/713; A61P 25/28

See application file for complete search history.

(56) References Cited

PUBLICATIONS

Tryba et al , Role of TRPC3 channels in BDNF-induced plasticity, hippocampal neuronal excitability and memory, The FASEB Journal, 2012, vol. 26, issue S1, p. 1056.14 (Year: 2012).*

GenBank NM_001130698 , *Homo sapiens* transient receptor potential cation channel subfamily C member 3 (TRPC3), transcript variant 1, mRNA, GenBank, 2005, pp. 1-5 (Year: 2005).*

Montecinos-Oliva et al , Tetrahydrohyperforin: a neuroprotective modified natural compound against Alzheimer's disease, Neural Regeneration Research, 2015, vol. 10, issue 4: 552-554 (Year: 2015).*

Zhang et al , Relathionship between BDNF and TRPC3 in a rat model of Alzheimer's disease induced by beta-amyloid protein, Journal of China Medical University, 2018, 12: 217-221 (Year: 2018).*

Neuner et al—2017 , Systems genetics identifies modifiers of Alzheimer's disease risk and resilience, bioRxiv, Nov. 2017, 225714, pp. 1-38 (Year: 2017).*

Berchtold et al., Synaptic genes are extensively downregulated across multiple brain regions in normal human aging and Alzheimer's disease. Neurobiol Aging. Jun. 2013;34(6):1653-61. doi: 10.1016/j.neurobiolaging.2012.11.024. Epub Dec. 27, 2012.

Blalock et al., Microarray analyses of laser-captured hippocampus reveal distinct gray and white matter signatures associated with incipient Alzheimer's disease. J Chem Neuroanat. Oct. 2011;42(2): 118-26. doi: 10.1016/j.jchemneu.2011.06.007. Epub Jul. 2, 2011.

Blalock et al., Incipient Alzheimer's disease: microarray correlation analyses reveal major transcriptional and tumor suppressor responses. Proc Natl Acad Sci U S A. Feb. 17, 2004;101(7):2173-8. Epub Feb. 9, 2004.

Brier et al., Tau and A? imaging, CSF measures, and cognition in Alzheimer's disease. Sci Transl Med. May 2016 11;8(338):1-9. doi: 10.1126/scitranslmed.aaf2362.

Fanselow, Contextual fear, gestalt memories, and the hippocampus. Behav Brain Res. Jun. 1, 2000;110(1-2):73-81.

Hargis et al., Transcriptional signatures of brain aging and Alzheimer's disease: What are our rodent models telling us? Behav Brain Res. Mar. 30, 2017;322(Pt B):311-328. doi: 10.1016/j.bbr.2016.05.007. Epub May 4, 2016.

Hokama et al., Altered expression of diabetes-related genes in Alzheimer's disease brains: the Hisayama study. Cereb Cortex. Sep. 2014;24(9):2476-88. doi: 10.1093/cercor/bht101. Epub Apr. 17, 2013.

Hong et al., Complement and microglia mediate early synapse loss in Alzheimer mouse models. Science. May 6, 2016;352(6286):712-716. doi: 10.1126/science.aad8373. Epub Mar. 31, 2016.

Jackson et al., DBA/2J genetic background exacerbates spontaneous lethal seizures but lessens amyloid deposition in a mouse model of Alzheimer's disease. PLoS One. May 1, 2015;10(5):e0125897. doi: 10.1371/journal.pone.0125897.

Kaczorowski et al., Memory deficits are associated with impaired ability to modulate neuronal excitability in middle-aged mice. Learn Mem. May 23, 2009;16(6):362-6. doi: 10.1101/lm.1365609.

Kaczorowski et al., Mechanisms underlying basal and learning-related intrinsic excitability in a mouse model of Alzheimer's disease. Neurobiol Aging. Aug. 2011;32(8):1452-65. doi: 10.1016/j.neurobiolaging.2009.09.003. Epub Oct. 14, 2009.

Karch et al., Expression of novel Alzheimer's disease risk genes in control and Alzheimer's disease brains. PLoS One. 2012;7(11):e50976. doi: 10.1371/journal.pone.0050976. Epub Nov. 30, 2012.

Kitazawa et al., Transgenic mouse models of Alzheimer disease: developing a better model as a tool for therapeutic interventions. Curr Pharm Des. 2012;18(8):1131-47.

Lambert et al., Meta-analysis of 74,046 individuals identifies 11 new susceptibility loci for Alzheimer's disease. Nat Genet. Dec. 2013;45(12): 1452-8. doi: 10.1038/ng.2802. Epub Oct. 27, 2013.

(Continued)

*Primary Examiner* — Ekaterina Poliakova-Georgantas

(74) *Attorney, Agent, or Firm* — Wolf, Greenfield & Sacks, P.C.

(57) ABSTRACT

Provided herein, in some embodiments, are methods for modulating expression and/or activity of transient receptor potential cation channel subfamily C, member 3 (TRPC3), as well as methods of treating Alzheimer's disease.

12 Claims, 17 Drawing Sheets

Specification includes a Sequence Listing.

(56) References Cited

PUBLICATIONS

Liao et al., Murine versus human apolipoprotein E4: differential facilitation of and co-localization in cerebral amyloid angiopathy and amyloid plaques in APP transgenic mouse models. Acta Neuropathol Commun. Nov. 10, 2015;3:70. doi: 10.1186/s40478-015-0250-y.
Neuner et al., Systems genetics identifies Hp1bp3 as a novel modulator of cognitive aging. Neurobiol Aging. Oct. 2016;46:58-67. doi: 10.1016/j.neurobiolaging.2016.06.008. Epub Jun. 17, 2016.
Neuner et al., TRPC3 channels critically regulate hippocampal excitability and contextual fear memory. Behav Brain Res. Mar. 15, 2015;281:69-77. doi: 10.1016/j.bbr.2014.12.018. Epub Dec. 13, 2014.
Oakley et al., Intraneuronal beta-amyloid aggregates, neurodegeneration, and neuron loss in transgenic mice with five familial Alzheimer's disease mutations: potential factors in amyloid plaque formation. J Neurosci. Oct. 4, 2006;26(40):10129-40.
Ohno, Failures to reconsolidate memory in a mouse model of Alzheimer's disease. Neurobiol Learn Mem. Oct. 2009;92(3):455-9. doi: 10.1016/j.nlm.2009.05.001. Epub May 10, 2009.
Onos et al., Toward more predictive genetic mouse models of Alzheimer's disease. Brain Res Bull. Apr. 2016;122:1-11. doi: 10.1016/j.brainresbull.2015.12.003. Epub Dec. 17, 2015.
Peirce et al., A new set of BXD recombinant inbred lines from advanced intercross populations in mice. BMC Genet. Apr. 29, 2004;5:7.
Piccio et al., Cerebrospinal fluid soluble TREM2 is higher in Alzheimer disease and associated with mutation status. Acta Neuropathol. Jun. 2016;131(6):925-33. doi: 10.1007/s00401-016-1533-5. Epub Jan. 11, 2016.
Ridge et al., Alzheimer's Disease Genetics Consortium. Alzheimer's disease: analyzing the missing heritability. PLoS One. Nov. 7, 2013;8(11):e79771. doi: 10.1371/journal.pone.0079771.
Ryman et al., Genetic loci modulating amyloid-beta levels in a mouse model of Alzheimer's disease. Neurobiol Aging. Aug. 2008;29(8):1190-8. Epub Apr. 2, 2007.
Ryman et al., Symptom onset in autosomal dominant Alzheimer disease: a systematic review and meta-analysis. Neurology. Jul. 15, 2014;83(3):253-60. doi: 10.1212/WNL.0000000000000596. Epub Jun. 13, 2014.
Sadleir et al., A? reduction in BACE1 heterozygous null 5XFAD mice is associated with transgenic APP level. Mol Neurodegener. Jan. 7, 2015;10:1. doi: 10.1186/1750-1326-10-1.
Sebastiani et al., Mapping genetic modulators of amyloid plaque deposition in TgCRND8 transgenic mice. Hum Mol Genet. Aug. 1, 2006;15(15):2313-23. Epub Jun. 19, 2006.
Taylor et al., Genotyping new BXD recombinant inbred mouse strains and comparison of BXD and consensus maps. Mamm Genome. Apr. 1999;10(4):335-48.
Wang et al., Joint mouse-human phenome-wide association to test gene function and disease risk. Nat Commun. Feb. 2, 2016;7:10464. doi: 10.1038/ncomms10464.
Zerbino et al., Ensembl 2018. Nucleic Acids Res. Jan. 4, 2018;46(D1):D754-D761. doi: 10.1093/nar/gkx1098.
Zhang et al., Integrated systems approach identifies genetic nodes and networks in late-onset Alzheimer's disease. Cell. Apr. 25, 2013;153(3):707-20. doi: 10.1016/j.cell.2013.03.030.
Zokaei et al., Sex and APOE: A memory advantage in male APOE ?4 carriers in midlife. Cortex. 2017;88:98-105. doi:10.1016/j.cortex.2016.12.016.
Amir et al., Lapatinib and HER2 status: results of a meta-analysis of randomized phase III trials in metastatic breast cancer. Cancer Treat Rev. Aug. 2010;36(5):410-5. doi: 10.1016/j.ctrv.2009.12.012. Epub Jan. 25, 2010.
Bang et al., Trastuzumab in combination with chemotherapy versus chemotherapy alone for treatment of HER2-positive advanced gastric or gastro-oesophageal junction cancer (ToGA): a phase 3, open-label, randomised controlled trial. Lancet. Aug. 28, 2010;376(9742):687-97. doi: 10.1016/S0140-6736(10)61121-X. Epub Aug. 19, 2010. Erratum in: Lancet. Oct. 16, 2010;376(9749):1302.
Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.
Harris et al., The genetics of cognitive ability and cognitive ageing in healthy older people. Trends Cogn Sci. Sep. 2011;15(9):388-94. doi: 10.1016/j.tics.2011.07.004. Epub Aug. 15, 2011.
Ito et al., Uroporphyrinogen decarboxylase: optimizing radiotherapy for head and neck cancer. Future Oncol. May 2011;7(5):595-7. doi: 10.2217/fon.11.27.
Joung et al., Genome-scale CRISPR-Cas9 knockout and transcriptional activation screening. Nat Protoc. Apr. 2017;12(4):828-863. doi: 10.1038/nprot.2017.016. Epub Mar. 23, 2017. Erratum in: Nat Protoc. Jul. 2019;14(7):2259.
Kim et al., HISAT: a fast spliced aligner with low memory requirements. Nat Methods. Apr. 2015;12(4):357-60. doi: 10.1038/nmeth.3317. Epub Mar. 9, 2015.
Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.
Lee et al., Molecular targeted therapy: Treating cancer with specificity. Eur J Pharmacol. Sep. 5, 2018;834:188-196. doi: 10.1016/j.ejphar.2018.07.034. Epub Jul. 20, 2018.
Reynolds et al., Rational siRNA design for RNA interference. Nat Biotechnol. Mar. 2004;22(3):326-30. doi: 10.1038/nbt936. Epub Feb. 1, 2004.
Shalem et al., Genome-scale CRISPR-Cas9 knockout screening in human cells. Science. Jan. 3, 2014;343(6166):84-87. doi: 10.1126/science.1247005. Epub Dec. 12, 2013.

* cited by examiner

SEQUENCE LISTING

<160> NUMBER OF SEQ ID NOS: 8

<210> SEQ ID NO 1
<211> LENGTH: 921
<212> TYPE: PRT
<213> ORGANISM: Homo sapiens

<400> SEQUENCE: 1

Met Ser Thr Lys Val Arg Lys Cys Lys Glu Gln Ala Arg Val Thr Phe
1 5 10 15

Pro Ala Pro Glu Glu Glu Glu Asp Glu Gly Glu Asp Glu Gly Ala Glu
20 25 30

Pro Gln Arg Arg Arg Arg Gly Trp Arg Gly Val Asn Gly Gly Leu Glu
35 40 45

Pro Arg Ser Ala Pro Ser Gln Arg Glu Pro His Gly Tyr Cys Pro Pro
50 55 60

Pro Phe Ser His Gly Pro Asp Leu Ser Met Glu Gly Ser Pro Ser Leu
65 70 75 80

Arg Arg Met Thr Val Met Arg Glu Lys Gly Arg Arg Gln Ala Val Arg
85 90 95

Gly Pro Ala Phe Met Phe Asn Asp Arg Gly Thr Ser Leu Thr Ala Glu
100 105 110

Glu Glu Arg Phe Leu Asp Ala Ala Glu Tyr Gly Asn Ile Pro Val Val
115 120 125

Arg Lys Met Leu Glu Glu Ser Lys Thr Leu Asn Val Asn Cys Val Asp
130 135 140

Tyr Met Gly Gln Asn Ala Leu Gln Leu Ala Val Gly Asn Glu His Leu
145 150 155 160

Glu Val Thr Glu Leu Leu Leu Lys Lys Glu Asn Leu Ala Arg Ile Gly
165 170 175

Asp Ala Leu Leu Leu Ala Ile Ser Lys Gly Tyr Val Arg Ile Val Glu
180 185 190

Ala Ile Leu Asn His Pro Gly Phe Ala Ala Ser Lys Arg Leu Thr Leu
195 200 205

Ser Pro Cys Glu Gln Glu Leu Gln Asp Asp Asp Phe Tyr Ala Tyr Asp
210 215 220

Glu Asp Gly Thr Arg Phe Ser Pro Asp Ile Thr Pro Ile Ile Leu Ala
225 230 235 240

Ala His Cys Gln Lys Tyr Glu Val Val His Met Leu Leu Met Lys Gly
245 250 255

Ala Arg Ile Glu Arg Pro His Asp Tyr Phe Cys Lys Cys Gly Asp Cys
260 265 270

Met Glu Lys Gln Arg His Asp Ser Phe Ser His Ser Arg Ser Arg Ile
275 280 285

Asn Ala Tyr Lys Gly Leu Ala Ser Pro Ala Tyr Leu Ser Leu Ser Ser
290 295 300

Glu Asp Pro Val Leu Thr Ala Leu Glu Leu Ser Asn Glu Leu Ala Lys
305 310 315 320

Leu Ala Asn Ile Glu Lys Glu Phe Lys Asn Asp Tyr Arg Lys Leu Ser
325 330 335

Met Gln Cys Lys Asp Phe Val Val Gly Val Leu Asp Leu Cys Arg Asp
340 345 350

Ser Glu Glu Val Glu Ala Ile Leu Asn Gly Asp Leu Glu Ser Ala Glu
355 360 365

-continued

```
Pro Leu Glu Val His Arg His Lys Ala Ser Leu Ser Arg Val Lys Leu
    370                 375                 380

Ala Ile Lys Tyr Glu Val Lys Lys Phe Val Ala His Pro Asn Cys Gln
385                 390                 395                 400

Gln Gln Leu Leu Thr Ile Trp Tyr Glu Asn Leu Ser Gly Leu Arg Glu
                405                 410                 415

Gln Thr Ile Ala Ile Lys Cys Leu Val Val Leu Val Val Ala Leu Gly
            420                 425                 430

Leu Pro Phe Leu Ala Ile Gly Tyr Trp Ile Ala Pro Cys Ser Arg Leu
        435                 440                 445

Gly Lys Ile Leu Arg Ser Pro Phe Met Lys Phe Val Ala His Ala Ala
    450                 455                 460

Ser Phe Ile Ile Phe Leu Gly Leu Leu Val Phe Asn Ala Ser Asp Arg
465                 470                 475                 480

Phe Glu Gly Ile Thr Thr Leu Pro Asn Ile Thr Val Thr Asp Tyr Pro
                485                 490                 495

Lys Gln Ile Phe Arg Val Lys Thr Thr Gln Phe Thr Trp Thr Glu Met
            500                 505                 510

Leu Ile Met Val Trp Val Leu Gly Met Met Trp Ser Glu Cys Lys Glu
        515                 520                 525

Leu Trp Leu Glu Gly Pro Arg Glu Tyr Ile Leu Gln Leu Trp Asn Val
    530                 535                 540

Leu Asp Phe Gly Met Leu Ser Ile Phe Ile Ala Ala Phe Thr Ala Arg
545                 550                 555                 560

Phe Leu Ala Phe Leu Gln Ala Thr Lys Ala Gln Gln Tyr Val Asp Ser
                565                 570                 575

Tyr Val Gln Glu Ser Asp Leu Ser Glu Val Thr Leu Pro Pro Glu Ile
            580                 585                 590

Gln Tyr Phe Thr Tyr Ala Arg Asp Lys Trp Leu Pro Ser Asp Pro Gln
        595                 600                 605

Ile Ile Ser Glu Gly Leu Tyr Ala Ile Ala Val Val Leu Ser Phe Ser
    610                 615                 620

Arg Ile Ala Tyr Ile Leu Pro Ala Asn Glu Ser Phe Gly Pro Leu Gln
625                 630                 635                 640

Ile Ser Leu Gly Arg Thr Val Lys Asp Ile Phe Lys Phe Met Val Leu
                645                 650                 655

Phe Ile Met Val Phe Phe Ala Phe Met Ile Gly Met Phe Ile Leu Tyr
            660                 665                 670

Ser Tyr Tyr Leu Gly Ala Lys Val Asn Ala Ala Phe Thr Thr Val Glu
        675                 680                 685

Glu Ser Phe Lys Thr Leu Phe Trp Ser Ile Phe Gly Leu Ser Glu Val
    690                 695                 700

Thr Ser Val Val Leu Lys Tyr Asp His Lys Phe Ile Glu Asn Ile Gly
705                 710                 715                 720

Tyr Val Leu Tyr Gly Ile Tyr Asn Val Thr Met Val Val Val Leu Leu
                725                 730                 735

Asn Met Leu Ile Ala Met Ile Asn Ser Ser Tyr Gln Glu Ile Glu Asp
            740                 745                 750

Asp Ser Asp Val Glu Trp Lys Phe Ala Arg Ser Lys Leu Trp Leu Ser
        755                 760                 765

Tyr Phe Asp Asp Gly Lys Thr Leu Pro Pro Pro Phe Ser Leu Val Pro
    770                 775                 780

Ser Pro Lys Ser Phe Val Tyr Phe Ile Met Arg Ile Val Asn Phe Pro
```

```
785                 790                 795                 800

Lys Cys Arg Arg Arg Arg Leu Gln Lys Asp Ile Glu Met Gly Met Gly
                805                 810                 815

Asn Ser Lys Ser Arg Leu Asn Leu Phe Thr Gln Ser Asn Ser Arg Val
            820                 825                 830

Phe Glu Ser His Ser Phe Asn Ser Ile Leu Asn Gln Pro Thr Arg Tyr
        835                 840                 845

Gln Gln Ile Met Lys Arg Leu Ile Lys Arg Tyr Val Leu Lys Ala Gln
    850                 855                 860

Val Asp Lys Glu Asn Asp Glu Val Asn Glu Gly Glu Leu Lys Glu Ile
865                 870                 875                 880

Lys Gln Asp Ile Ser Ser Leu Arg Tyr Glu Leu Leu Glu Asp Lys Ser
                885                 890                 895

Gln Ala Thr Glu Glu Leu Ala Ile Leu Ile His Lys Leu Ser Glu Lys
            900                 905                 910

Leu Asn Pro Ser Met Leu Arg Cys Glu
        915                 920


<210> SEQ ID NO 2
<211> LENGTH: 848
<212> TYPE: PRT
<213> ORGANISM: Homo sapiens

<400> SEQUENCE: 2

Met Glu Gly Ser Pro Ser Leu Arg Arg Met Thr Val Met Arg Glu Lys
1               5                   10                  15

Gly Arg Arg Gln Ala Val Arg Gly Pro Ala Phe Met Phe Asn Asp Arg
            20                  25                  30

Gly Thr Ser Leu Thr Ala Glu Glu Glu Arg Phe Leu Asp Ala Ala Glu
        35                  40                  45

Tyr Gly Asn Ile Pro Val Val Arg Lys Met Leu Glu Glu Ser Lys Thr
    50                  55                  60

Leu Asn Val Asn Cys Val Asp Tyr Met Gly Gln Asn Ala Leu Gln Leu
65                  70                  75                  80

Ala Val Gly Asn Glu His Leu Glu Val Thr Glu Leu Leu Leu Lys Lys
                85                  90                  95

Glu Asn Leu Ala Arg Ile Gly Asp Ala Leu Leu Leu Ala Ile Ser Lys
            100                 105                 110

Gly Tyr Val Arg Ile Val Glu Ala Ile Leu Asn His Pro Gly Phe Ala
        115                 120                 125

Ala Ser Lys Arg Leu Thr Leu Ser Pro Cys Glu Gln Glu Leu Gln Asp
    130                 135                 140

Asp Asp Phe Tyr Ala Tyr Asp Glu Asp Gly Thr Arg Phe Ser Pro Asp
145                 150                 155                 160

Ile Thr Pro Ile Ile Leu Ala Ala His Cys Gln Lys Tyr Glu Val Val
                165                 170                 175

His Met Leu Leu Met Lys Gly Ala Arg Ile Glu Arg Pro His Asp Tyr
            180                 185                 190

Phe Cys Lys Cys Gly Asp Cys Met Glu Lys Gln Arg His Asp Ser Phe
        195                 200                 205

Ser His Ser Arg Ser Arg Ile Asn Ala Tyr Lys Gly Leu Ala Ser Pro
    210                 215                 220

Ala Tyr Leu Ser Leu Ser Ser Glu Asp Pro Val Leu Thr Ala Leu Glu
225                 230                 235                 240
```

-continued

```
Leu Ser Asn Glu Leu Ala Lys Leu Ala Asn Ile Glu Lys Glu Phe Lys
                245                 250                 255

Asn Asp Tyr Arg Lys Leu Ser Met Gln Cys Lys Asp Phe Val Val Gly
            260                 265                 270

Val Leu Asp Leu Cys Arg Asp Ser Glu Glu Val Glu Ala Ile Leu Asn
        275                 280                 285

Gly Asp Leu Glu Ser Ala Glu Pro Leu Glu Val His Arg His Lys Ala
    290                 295                 300

Ser Leu Ser Arg Val Lys Leu Ala Ile Lys Tyr Glu Val Lys Lys Phe
305                 310                 315                 320

Val Ala His Pro Asn Cys Gln Gln Gln Leu Leu Thr Ile Trp Tyr Glu
                325                 330                 335

Asn Leu Ser Gly Leu Arg Glu Gln Thr Ile Ala Ile Lys Cys Leu Val
            340                 345                 350

Val Leu Val Val Ala Leu Gly Leu Pro Phe Leu Ala Ile Gly Tyr Trp
        355                 360                 365

Ile Ala Pro Cys Ser Arg Leu Gly Lys Ile Leu Arg Ser Pro Phe Met
    370                 375                 380

Lys Phe Val Ala His Ala Ala Ser Phe Ile Ile Phe Leu Gly Leu Leu
385                 390                 395                 400

Val Phe Asn Ala Ser Asp Arg Phe Glu Gly Ile Thr Thr Leu Pro Asn
                405                 410                 415

Ile Thr Val Thr Asp Tyr Pro Lys Gln Ile Phe Arg Val Lys Thr Thr
            420                 425                 430

Gln Phe Thr Trp Thr Glu Met Leu Ile Met Val Trp Val Leu Gly Met
        435                 440                 445

Met Trp Ser Glu Cys Lys Glu Leu Trp Leu Glu Gly Pro Arg Glu Tyr
    450                 455                 460

Ile Leu Gln Leu Trp Asn Val Leu Asp Phe Gly Met Leu Ser Ile Phe
465                 470                 475                 480

Ile Ala Ala Phe Thr Ala Arg Phe Leu Ala Phe Leu Gln Ala Thr Lys
                485                 490                 495

Ala Gln Gln Tyr Val Asp Ser Tyr Val Gln Glu Ser Asp Leu Ser Glu
            500                 505                 510

Val Thr Leu Pro Pro Glu Ile Gln Tyr Phe Thr Tyr Ala Arg Asp Lys
        515                 520                 525

Trp Leu Pro Ser Asp Pro Gln Ile Ile Ser Glu Gly Leu Tyr Ala Ile
    530                 535                 540

Ala Val Val Leu Ser Phe Ser Arg Ile Ala Tyr Ile Leu Pro Ala Asn
545                 550                 555                 560

Glu Ser Phe Gly Pro Leu Gln Ile Ser Leu Gly Arg Thr Val Lys Asp
                565                 570                 575

Ile Phe Lys Phe Met Val Leu Phe Ile Met Val Phe Phe Ala Phe Met
            580                 585                 590

Ile Gly Met Phe Ile Leu Tyr Ser Tyr Tyr Leu Gly Ala Lys Val Asn
        595                 600                 605

Ala Ala Phe Thr Thr Val Glu Glu Ser Phe Lys Thr Leu Phe Trp Ser
    610                 615                 620

Ile Phe Gly Leu Ser Glu Val Thr Ser Val Val Leu Lys Tyr Asp His
625                 630                 635                 640

Lys Phe Ile Glu Asn Ile Gly Tyr Val Leu Tyr Gly Ile Tyr Asn Val
                645                 650                 655

Thr Met Val Val Val Leu Leu Asn Met Leu Ile Ala Met Ile Asn Ser
```

```
            660                 665                 670

Ser Tyr Gln Glu Ile Glu Asp Asp Ser Asp Val Glu Trp Lys Phe Ala
        675                 680                 685

Arg Ser Lys Leu Trp Leu Ser Tyr Phe Asp Asp Gly Lys Thr Leu Pro
    690                 695                 700

Pro Pro Phe Ser Leu Val Pro Ser Pro Lys Ser Phe Val Tyr Phe Ile
705                 710                 715                 720

Met Arg Ile Val Asn Phe Pro Lys Cys Arg Arg Arg Arg Leu Gln Lys
                725                 730                 735

Asp Ile Glu Met Gly Met Gly Asn Ser Lys Ser Arg Leu Asn Leu Phe
            740                 745                 750

Thr Gln Ser Asn Ser Arg Val Phe Glu Ser His Ser Phe Asn Ser Ile
        755                 760                 765

Leu Asn Gln Pro Thr Arg Tyr Gln Gln Ile Met Lys Arg Leu Ile Lys
    770                 775                 780

Arg Tyr Val Leu Lys Ala Gln Val Asp Lys Glu Asn Asp Glu Val Asn
785                 790                 795                 800

Glu Gly Glu Leu Lys Glu Ile Lys Gln Asp Ile Ser Ser Leu Arg Tyr
                805                 810                 815

Glu Leu Leu Glu Asp Lys Ser Gln Ala Thr Glu Glu Leu Ala Ile Leu
            820                 825                 830

Ile His Lys Leu Ser Glu Lys Leu Asn Pro Ser Met Leu Arg Cys Glu
        835                 840                 845


<210> SEQ ID NO 3
<211> LENGTH: 893
<212> TYPE: PRT
<213> ORGANISM: Homo sapiens

<400> SEQUENCE: 3

Met Ser Thr Lys Val Arg Lys Cys Lys Glu Gln Ala Arg Val Thr Phe
1               5                   10                  15

Pro Ala Pro Glu Glu Glu Glu Asp Glu Gly Glu Asp Glu Gly Ala Glu
            20                  25                  30

Pro Gln Arg Arg Arg Arg Gly Trp Arg Gly Val Asn Gly Gly Leu Glu
        35                  40                  45

Pro Arg Ser Ala Pro Ser Gln Arg Glu Pro His Gly Tyr Cys Pro Pro
    50                  55                  60

Pro Phe Ser His Gly Pro Asp Leu Ser Met Glu Gly Ser Pro Ser Leu
65                  70                  75                  80

Arg Arg Met Thr Val Met Arg Glu Lys Gly Arg Arg Gln Ala Val Arg
                85                  90                  95

Gly Pro Ala Phe Met Phe Asn Asp Arg Gly Thr Ser Leu Thr Ala Glu
            100                 105                 110

Glu Glu Arg Phe Leu Asp Ala Ala Glu Tyr Gly Asn Ile Pro Val Val
        115                 120                 125

Arg Lys Met Leu Glu Glu Ser Lys Thr Leu Asn Val Asn Cys Val Asp
    130                 135                 140

Tyr Met Gly Gln Asn Ala Leu Gln Leu Ala Val Gly Asn Glu His Leu
145                 150                 155                 160

Glu Val Thr Glu Leu Leu Leu Lys Lys Glu Asn Leu Ala Arg Ile Gly
                165                 170                 175

Asp Ala Leu Leu Leu Ala Ile Ser Lys Gly Tyr Val Arg Ile Val Glu
            180                 185                 190
```

```
Ala Ile Leu Asn His Pro Gly Phe Ala Ala Ser Lys Arg Leu Thr Leu
        195                 200                 205

Ser Pro Cys Glu Gln Glu Leu Gln Asp Asp Asp Phe Tyr Ala Tyr Asp
    210                 215                 220

Glu Asp Gly Thr Arg Phe Ser Pro Asp Ile Thr Pro Ile Ile Leu Ala
225                 230                 235                 240

Ala His Cys Gln Lys Tyr Glu Val Val His Met Leu Leu Met Lys Gly
                245                 250                 255

Ala Arg Ile Glu Arg Pro His Asp Tyr Phe Cys Lys Cys Gly Asp Cys
            260                 265                 270

Met Glu Lys Gln Arg His Asp Ser Phe Ser His Ser Arg Ser Arg Ile
        275                 280                 285

Asn Ala Tyr Lys Gly Leu Ala Ser Pro Ala Tyr Leu Ser Leu Ser Ser
    290                 295                 300

Glu Asp Pro Val Leu Thr Ala Leu Glu Leu Ser Asn Glu Leu Ala Lys
305                 310                 315                 320

Leu Ala Asn Ile Glu Lys Glu Phe Lys Asn Asp Tyr Arg Lys Leu Ser
                325                 330                 335

Met Gln Cys Lys Asp Phe Val Val Gly Val Leu Asp Leu Cys Arg Asp
            340                 345                 350

Ser Glu Glu Val Glu Ala Ile Leu Asn Gly Asp Leu Glu Ser Ala Glu
        355                 360                 365

Pro Leu Glu Val His Arg His Lys Ala Ser Leu Ser Arg Val Lys Leu
    370                 375                 380

Ala Ile Lys Tyr Glu Val Lys Lys Phe Val Ala His Pro Asn Cys Gln
385                 390                 395                 400

Gln Gln Leu Leu Thr Ile Trp Tyr Glu Asn Leu Ser Gly Leu Arg Glu
                405                 410                 415

Gln Thr Ile Ala Ile Lys Cys Leu Val Val Leu Val Val Ala Leu Gly
            420                 425                 430

Leu Pro Phe Leu Ala Ile Gly Tyr Trp Ile Ala Pro Cys Ser Arg Leu
        435                 440                 445

Gly Lys Ile Leu Arg Ser Pro Phe Met Lys Phe Val Ala His Ala Ala
    450                 455                 460

Ser Phe Ile Ile Phe Leu Gly Leu Leu Val Phe Asn Ala Ser Asp Arg
465                 470                 475                 480

Phe Glu Gly Ile Thr Thr Leu Pro Asn Ile Thr Val Thr Asp Tyr Pro
                485                 490                 495

Lys Gln Ile Phe Arg Val Lys Thr Thr Gln Phe Thr Trp Thr Glu Met
            500                 505                 510

Leu Ile Met Val Trp Val Leu Gly Met Met Trp Ser Glu Cys Lys Glu
        515                 520                 525

Leu Trp Leu Glu Gly Pro Arg Glu Tyr Ile Leu Gln Leu Trp Asn Val
    530                 535                 540

Leu Asp Phe Gly Met Leu Ser Ile Phe Ile Ala Ala Phe Thr Ala Arg
545                 550                 555                 560

Phe Leu Ala Phe Leu Gln Ala Thr Lys Ala Gln Gln Tyr Val Asp Ser
                565                 570                 575

Tyr Val Gln Glu Ser Asp Leu Ser Glu Val Thr Leu Pro Pro Glu Ile
            580                 585                 590

Gln Tyr Phe Thr Tyr Ala Arg Asp Lys Trp Leu Pro Ser Asp Pro Gln
        595                 600                 605

Ile Ile Ser Glu Gly Leu Tyr Ala Ile Ala Val Val Leu Ser Phe Ser
```

-continued

```
    610                 615                 620

Arg Ile Ala Tyr Ile Leu Pro Ala Asn Glu Ser Phe Gly Pro Leu Gln
625                 630                 635                 640

Ile Ser Leu Gly Arg Thr Val Lys Asp Ile Phe Lys Phe Met Val Leu
                645                 650                 655

Phe Ile Met Val Phe Phe Ala Phe Met Ile Gly Met Phe Ile Leu Tyr
            660                 665                 670

Ser Tyr Tyr Leu Gly Ala Lys Val Asn Ala Ala Phe Thr Thr Val Glu
        675                 680                 685

Glu Ser Phe Lys Thr Leu Phe Trp Ser Ile Phe Gly Leu Ser Glu Val
    690                 695                 700

Thr Ser Val Val Leu Lys Tyr Asp His Lys Phe Ile Glu Asn Ile Gly
705                 710                 715                 720

Tyr Val Leu Tyr Gly Ile Tyr Asn Val Thr Met Val Val Val Leu Leu
                725                 730                 735

Asn Met Leu Ile Ala Met Ile Asn Ser Ser Tyr Gln Glu Ile Glu Asp
            740                 745                 750

Asp Ser Asp Val Glu Trp Lys Phe Ala Arg Ser Lys Leu Trp Leu Ser
        755                 760                 765

Tyr Phe Asp Asp Gly Lys Thr Leu Pro Pro Pro Phe Ser Leu Val Pro
    770                 775                 780

Ser Pro Lys Ser Phe Val Tyr Phe Ile Met Arg Ile Val Asn Phe Pro
785                 790                 795                 800

Lys Cys Arg Arg Arg Arg Leu Gln Lys Asp Ile Glu Met Gly Met Gly
                805                 810                 815

Asn Ser Lys Ser Arg Gln Ile Met Lys Arg Leu Ile Lys Arg Tyr Val
            820                 825                 830

Leu Lys Ala Gln Val Asp Lys Glu Asn Asp Glu Val Asn Glu Gly Glu
        835                 840                 845

Leu Lys Glu Ile Lys Gln Asp Ile Ser Ser Leu Arg Tyr Glu Leu Leu
    850                 855                 860

Glu Asp Lys Ser Gln Ala Thr Glu Glu Leu Ala Ile Leu Ile His Lys
865                 870                 875                 880

Leu Ser Glu Lys Leu Asn Pro Ser Met Leu Arg Cys Glu
                885                 890
```

```
<210> SEQ ID NO 4
<211> LENGTH: 3548
<212> TYPE: DNA
<213> ORGANISM: Homo sapiens

<400> SEQUENCE: 4

gggaagactg cactgccgcg aaggcggagg aggccggcag ccggcacccc cacactcgga      60

ccgcagccgg cgcgatgtcc accaaggtca ggaagtgcaa agaacaagca agggtgacct     120

tcccggcgcc ggaggaggag gaagacgagg gcgaggacga gggcgcggag ccgcagcgcc     180

gccgccgggg ctggaggggc gtcaacgggg ggctggagcc gcgctcggcg ccctcgcagc     240

gggagccgca cggctactgc ccgccgccct tctcccacgg gccggacctg tccatggagg     300

gaagcccatc cctgagacgc atgacagtga tgcgggagaa gggccggcgc caggctgtca     360

ggggcccggc cttcatgttc aatgaccgcg gcaccagcct caccgccgag gaggagcgct     420

tcctcgacgc cgccgagtac ggcaacatcc cagtggtgcg caagatgctg gaggagtcca     480

agacgctgaa cgtcaactgc gtggactaca tgggccagaa cgcgctgcag ctggctgtgg     540
```

-continued

```
gcaacgagca cctggaggtg accgagctgc tgctcaagaa ggagaacctg gcgcgcattg    600
gcgacgccct gctgctcgcc atcagcaagg gctacgtgcg catcgtagag gccatcctca    660
accaccctgg cttcgcggcc agcaagcgtc tcactctgag cccctgtgag caggagctgc    720
aggacgacga cttctacgct tacgacgagg acggcacgcg cttctcgccg gacatcaccc    780
ccatcatcct ggcggcgcac tgccagaaat acgaagtggt gcacatgctg ctgatgaagg    840
gtgccaggat cgagcggccg cacgactatt tctgcaagtg cggggactgc atggagaagc    900
agaggcacga ctccttcagc cactcacgct cgaggatcaa tgcctacaag gggctggcca    960
gcccggctta cctctcattg tccagcgagg acccggtgct tacggcccta gagctcagca   1020
acgagctggc caagctggcc aacatagaga aggagttcaa gaatgactat cggaagctct   1080
ccatgcaatg caaagacttt gtagtgggtg tgctggatct ctgccgagac tcagaagagg   1140
tagaagccat tctgaatgga gatctggaat cagcagagcc tctggaggta cacaggcaca   1200
aagcttcatt aagtcgtgtc aaacttgcca ttaagtatga agtcaaaaag tttgtggctc   1260
atcccaactg ccagcagcag ctcttgacga tctggtatga gaacctctca ggcctaaggg   1320
agcagaccat agctatcaag tgtctcgttg tgctggtcgt ggccctgggc cttccattcc   1380
tggccattgg ctactggatc gcaccttgca gcaggctggg gaaaattctg cgaagccctt   1440
ttatgaagtt tgtagcacat gcagcttctt tcatcatctt cctgggtctg cttgtgttca   1500
atgcctcaga caggttcgaa ggcatcacca cgctgcccaa tatcacagtt actgactatc   1560
ccaaacagat cttcagggtg aaaaccaccc agtttacatg gactgaaatg ctaattatgg   1620
tctgggttct tggaatgatg tggtctgaat gtaaagagct ctggctggaa ggacctaggg   1680
aatacatttt gcagttgtgg aatgtgcttg actttgggat gctgtccatc ttcattgctg   1740
ctttcacagc cagattccta gctttccttc aggcaacgaa ggcacaacag tatgtggaca   1800
gttacgtcca agagagtgac ctcagtgaag tgacactccc accagagata cagtatttca   1860
cttatgctag agataaatgg ctcccttctg accctcagat tatatctgaa ggcctttatg   1920
ccatagctgt tgtgctcagc ttctctcgga ttgcgtacat cctccctgca aatgagagct   1980
ttggcccct gcagatctct cttggaagga ctgtaaagga catattcaag ttcatggtcc    2040
tctttattat ggtgtttttt gcctttatga ttggcatgtt catactttat tcttactacc   2100
ttggggctaa agttaatgct gcttttacca ctgtagaaga aagtttcaag actttatttt   2160
ggtcaatatt tgggttgtct gaagtgactt ccgttgtgct caaatatgat cacaaattca   2220
tagaaaatat tggatacgtt ctttatggaa tatacaatgt aactatggtg gtcgttttac   2280
tcaacatgct aattgctatg attaatagct catatcaaga aattgaggat gacagtgatg   2340
tagaatggaa gtttgctcgt tcaaaacttt ggttatccta ttttgatgat ggaaaaacat   2400
tacctccacc tttcagtcta gttcctagtc caaaatcatt tgtttatttc atcatgcgaa   2460
ttgttaactt tcccaaatgc agaaggagaa ggcttcagaa ggatatagaa atgggaatgg   2520
gtaactcaaa gtccaggtta aacctcttca ctcagtctaa ctcaagagtt tttgaatcac   2580
acagttttaa cagcattctc aatcagccaa cacgttatca gcagataatg aaaagactta   2640
taaagcggta tgttttgaaa gcacaagtag acaaagaaaa tgatgaagtt aatgaaggtg   2700
aattaaaaga aatcaagcaa gatatctcca gccttcgtta tgaacttttg gaagacaaga   2760
gccaagcaac tgaggaatta gccattctaa ttcataaact tagtgagaaa ctgaatccca   2820
gcatgctgag atgtgaatga tgcagcaacc tggatttggc tttgactata gcacaaatgt   2880
gggcaataat atttctaagt atgaaatact tgaaaaacta tgatgtaaat tttagtatt    2940
```

aactaccttt atcatgtgaa cctttaaaag ttagctctta atggttttat tgttttatca 3000
catgaaaatg cattttattt gtctgctttg acattacagt ggcataccat tgtgttgaaa 3060
agcccaatat tactatatta ttgaaacttt tattcatttt agagtaaact ccacatcttt 3120
gcactacctg tttgcctcca agagactatc agttccttgg ggacagggac catgtcttat 3180
tcatctttgt gtctccagca tctagtacag tgcctggtat atagtaggtg ctcaataaat 3240
gttgaaacca actgaactgc caacaaaata aaaataaaaa gtcttcacta tgtagcatac 3300
cttcccttgt ccaagttctg aagaggtttt tttttttttt ttttaataga aactgaagac 3360
attttacaac cagctatgac ttggtaagac attcttagaa ttttaggtgt cactgataat 3420
cctagaacca ctgagcccca agtgaagaat ttaacaacaa aatgggttaa tgaaaaatat 3480
aattacattg tatatttaag tttcatagaa ttatttaaaa caacacatta aagatttttc 3540
taaaatat 3548

<210> SEQ ID NO 5
<211> LENGTH: 3330
<212> TYPE: DNA
<213> ORGANISM: Homo sapiens

<400> SEQUENCE: 5
gggccctgac atgtgaaagg aaggaatgtg ccctaatatt ctacagttgt tttatcgttg 60
ctactgatta ggtccatgga gggaagccca tccctgagac gcatgacagt gatgcgggag 120
aagggccggc gccaggctgt caggggcccg gccttcatgt tcaatgaccg cggcaccagc 180
ctcaccgccg aggaggagcg cttcctcgac gccgccgagt acggcaacat cccagtggtg 240
cgcaagatgc tggaggagtc caagacgctg aacgtcaact gcgtggacta catgggccag 300
aacgcgctgc agctggctgt gggcaacgag cacctggagg tgaccgagct gctgctcaag 360
aaggagaacc tggcgcgcat tggcgacgcc ctgctgctcg ccatcagcaa gggctacgtg 420
cgcatcgtag aggccatcct caaccaccct ggcttcgcgg ccagcaagcg tctcactctg 480
agcccctgtg agcaggagct gcaggacgac gacttctacg cttacgacga ggacggcacg 540
cgcttctcgc cggacatcac ccccatcatc ctggcggcgc actgccagaa atacgaagtg 600
gtgcacatgc tgctgatgaa gggtgccagg atcgagcggc cgcacgacta tttctgcaag 660
tgcggggact gcatggagaa gcagaggcac gactccttca gccactcacg ctcgaggatc 720
aatgcctaca aggggctggc cagcccggct tacctctcat tgtccagcga ggacccggtg 780
cttacggccc tagagctcag caacgagctg gccaagctgg ccaacataga gaaggagttc 840
aagaatgact atcggaagct ctccatgcaa tgcaaagact ttgtagtggg tgtgctggat 900
ctctgccgag actcagaaga ggtagaagcc attctgaatg gagatctgga atcagcagag 960
cctctggagg tacacaggca caaagcttca ttaagtcgtg tcaaacttgc cattaagtat 1020
gaagtcaaaa agtttgtggc tcatcccaac tgccagcagc agctcttgac gatctggtat 1080
gagaacctct caggcctaag ggagcagacc atagctatca agtgtctcgt tgtgctggtc 1140
gtggccctgg gccttccatt cctggccatt ggctactgga tcgcaccttg cagcaggctg 1200
gggaaaattc tgcgaagccc ttttatgaag tttgtagcac atgcagcttc tttcatcatc 1260
ttcctgggtc tgcttgtgtt caatgcctca gacaggttcg aaggcatcac cacgctgccc 1320
aatatcacag ttactgacta tcccaaacag atcttcaggg tgaaaaccac ccagtttaca 1380
tggactgaaa tgctaattat ggtctgggtt cttggaatga tgtggtctga atgtaaagag 1440

-continued

```
ctctggctgg aaggacctag ggaatacatt ttgcagttgt ggaatgtgct tgactttggg   1500
atgctgtcca tcttcattgc tgctttcaca gccagattcc tagctttcct tcaggcaacg   1560
aaggcacaac agtatgtgga cagttacgtc caagagagtg acctcagtga agtgacactc   1620
ccaccagaga tacagtattt cacttatgct agagataaat ggctcccttc tgaccctcag   1680
attatatctg aaggccttta tgccatagct gttgtgctca gcttctctcg gattgcgtac   1740
atcctccctg caaatgagag ctttggcccc ctgcagatct ctcttggaag gactgtaaag   1800
gacatattca agttcatggt cctctttatt atggtgtttt ttgcctttat gattggcatg   1860
ttcatacttt attcttacta ccttggggct aaagttaatg ctgcttttac cactgtagaa   1920
gaaagtttca agactttatt ttggtcaata tttgggttgt ctgaagtgac ttccgttgtg   1980
ctcaaatatg atcacaaatt catagaaaat attggatacg ttctttatgg aatatacaat   2040
gtaactatgg tggtcgtttt actcaacatg ctaattgcta tgattaatag ctcatatcaa   2100
gaaattgagg atgacagtga tgtagaatgg aagtttgctc gttcaaaact ttggttatcc   2160
tattttgatg atggaaaaac attacctcca cctttcagtc tagttcctag tccaaaatca   2220
tttgtttatt tcatcatgcg aattgttaac tttcccaaat gcagaaggag aaggcttcag   2280
aaggatatag aaatgggaat gggtaactca aagtccaggt taaacctctt cactcagtct   2340
aactcaagag tttttgaatc acacagtttt aacagcattc tcaatcagcc aacacgttat   2400
cagcagataa tgaaaagact tataaagcgg tatgttttga aagcacaagt agacaaagaa   2460
aatgatgaag ttaatgaagg tgaattaaaa gaaatcaagc aagatatctc cagccttcgt   2520
tatgaacttt tggaagacaa gagccaagca actgaggaat tagccattct aattcataaa   2580
cttagtgaga aactgaatcc cagcatgctg agatgtgaat gatgcagcaa cctggatttg   2640
gctttgacta tagcacaaat gtgggcaata atatttctaa gtatgaaata cttgaaaaac   2700
tatgatgtaa atttttagta ttaactacct ttatcatgtg aacctttaaa agttagctct   2760
taatggtttt attgttttat cacatgaaaa tgcattttat ttgtctgctt tgacattaca   2820
gtggcatacc attgtgttga aaagcccaat attactatat tattgaaact tttattcatt   2880
ttagagtaaa ctccacatct ttgcactacc tgtttgcctc caagagacta tcagttcctt   2940
ggggacaggg accatgtctt attcatcttt gtgtctccag catctagtac agtgcctggt   3000
atatagtagg tgctcaataa atgttgaaac caactgaact gccaacaaaa taaaaataaa   3060
aagtcttcac tatgtagcat accttccctt gtccaagttc tgaagaggtt tttttttttt   3120
ttttttaata gaaactgaag acattttaca accagctatg acttggtaag acattcttag   3180
aattttaggt gtcactgata atcctagaac cactgagccc caagtgaaga atttaacaac   3240
aaaatgggtt aatgaaaaat ataattacat tgtatattta agtttcatag aattatttaa   3300
aacaacacat taaagatttt tctaaaatat                                    3330
```

<210> SEQ ID NO 6
<211> LENGTH: 4708
<212> TYPE: DNA
<213> ORGANISM: Homo sapiens

<400> SEQUENCE: 6

```
gagtaacgat gctgtcctag caagtgatgc tgtcggagac aggagacggg cgccgaggag     60
gcatcgccgc cgccgcgggg ctggagagcc tctcccagca ccagagcccc gctcggcccc    120
gggcttcctc gtcgcagcca cggccgcggc agctgctccc acggtttgat ggtgggcggc    180
ggcagctcgg cttcggcgct agcctctaac tgctggatcg cgggccgcga cgctctccgc    240
```

-continued

```
tcctgccttc ccgccctggg ccgcccgggg ccccggaagc cgcgggaggt ggtgaagggg    300
cgccgcggga agactgcact gccgcgaagg cggaggaggc cggcagccgg cacccccaca    360
ctcggaccgc agccggcgcg atgtccacca aggtcaggaa gtgcaaagaa caagcaaggg    420
tgaccttccc ggcgccggag gaggaggaag acgagggcga ggacgagggc gcggagccgc    480
agcgccgccg ccggggctgg aggggcgtca acggggggct ggagccgcgc tcggcgccct    540
cgcagcggga gccgcacggc tactgcccgc cgcccttctc ccacgggccg gacctgtcca    600
tggagggaag cccatccctg agacgcatga cagtgatgcg ggagaagggc cggcgccagg    660
ctgtcagggg cccggccttc atgttcaatg accgcggcac cagcctcacc gccgaggagg    720
agcgcttcct cgacgccgcc gagtacggca acatcccagt ggtgcgcaag atgctggagg    780
agtccaagac gctgaacgtc aactgcgtgg actacatggg ccagaacgcg ctgcagctgg    840
ctgtgggcaa cgagcacctg gaggtgaccg agctgctgct caagaaggag aacctggcgc    900
gcattggcga cgccctgctg ctcgccatca gcaagggcta cgtgcgcatc gtagaggcca    960
tcctcaacca ccctggcttc gcggccagca agcgtctcac tctgagcccc tgtgagcagg   1020
agctgcagga cgacgacttc tacgcttacg acgaggacgg cacgcgcttc tcgccggaca   1080
tcacccccat catcctggcg gcgcactgcc agaaatacga agtggtgcac atgctgctga   1140
tgaagggtgc caggatcgag cggccgcacg actatttctg caagtgcggg gactgcatgg   1200
agaagcagag gcacgactcc ttcagccact cacgctcgag gatcaatgcc tacaaggggc   1260
tggccagccc ggcttacctc tcattgtcca gcgaggaccc ggtgcttacg gccctagagc   1320
tcagcaacga gctggccaag ctggccaaca tagagaagga gttcaagaat gactatcgga   1380
agctctccat gcaatgcaaa gactttgtag tgggtgtgct ggatctctgc cgagactcag   1440
aagaggtaga agccattctg aatggagatc tggaatcagc agagcctctg gaggtacaca   1500
ggcacaaagc ttcattaagt cgtgtcaaac ttgccattaa gtatgaagtc aaaaagtttg   1560
tggctcatcc caactgccag cagcagctct tgacgatctg gtatgagaac ctctcaggcc   1620
taagggagca gaccatagct atcaagtgtc tcgttgtgct ggtcgtggcc ctgggccttc   1680
cattcctggc cattggctac tggatcgcac cttgcagcag gctggggaaa attctgcgaa   1740
gcccttttat gaagtttgta gcacatgcag cttctttcat catcttcctg ggtctgcttg   1800
tgttcaatgc ctcagacagg ttcgaaggca tcaccacgct gcccaatatc acagttactg   1860
actatcccaa acagatcttc agggtgaaaa ccacccagtt tacatggact gaaatgctaa   1920
ttatggtctg ggttcttgga atgatgtggt ctgaatgtaa agagctctgg ctggaaggac   1980
ctagggaata cattttgcag ttgtggaatg tgcttgactt tgggatgctg tccatcttca   2040
ttgctgcttt cacagccaga ttcctagctt tccttcaggc aacgaaggca caacagtatg   2100
tggacagtta cgtccaagag agtgacctca gtgaagtgac actcccacca gagatacagt   2160
atttcactta tgctagagat aaatggctcc cttctgaccc tcagattata tctgaaggcc   2220
tttatgccat agctgttgtg ctcagcttct ctcggattgc gtacatcctc cctgcaaatg   2280
agagctttgg ccccctgcag atctctcttg gaaggactgt aaaggacata ttcaagttca   2340
tggtcctctt tattatggtg ttttttgcct ttatgattgg catgttcata ctttattctt   2400
actaccttgg ggctaaagtt aatgctgctt ttaccactgt agaagaaagt ttcaagactt   2460
tattttggtc aatatttggg ttgtctgaag tgacttccgt tgtgctcaaa tatgatcaca   2520
aattcataga aaatattgga tacgttcttt atggaatata caatgtaact atggtggtcg   2580
```

-continued

```
ttttactcaa catgctaatt gctatgatta atagctcata tcaagaaatt gaggatgaca   2640
gtgatgtaga atggaagttt gctcgttcaa aactttggtt atcctatttt gatgatggaa   2700
aaacattacc tccacctttc agtctagttc ctagtccaaa atcatttgtt tatttcatca   2760
tgcgaattgt taactttccc aaatgcagaa ggagaaggct tcagaaggat atagaaatgg   2820
gaatgggtaa ctcaaagtcc aggcagataa tgaaaagact tataaagcgg tatgttttga   2880
aagcacaagt agacaaagaa aatgatgaag ttaatgaagg tgaattaaaa gaaatcaagc   2940
aagatatctc cagccttcgt tatgaacttt tggaagacaa gagccaagca actgaggaat   3000
tagccattct aattcataaa cttagtgaga aactgaatcc cagcatgctg agatgtgaat   3060
gatgcagcaa cctggatttg gctttgacta tagcacaaat gtgggcaata atatttctaa   3120
gtatgaaata cttgaaaaac tatgatgtaa atttttagta ttaactacct ttatcatgtg   3180
aacctttaaa agttagctct taatggtttt attgttttat cacatgaaaa tgcattttat   3240
ttgtctgctt tgacattaca gtggcatacc attgtgttga aaagcccaat attactatat   3300
tattgaaact tttattcatt ttagagtaaa ctccacatct ttgcactacc tgtttgcctc   3360
caagagacta tcagttcctt ggggacaggg accatgtctt attcatcttt gtgtctccag   3420
catctagtac agtgcctggt atatagtagg tgctcaataa atgttgaaac caactgaact   3480
gccaacaaaa taaaaataaa aagtcttcac tatgtagcat accttccctt gtccaagttc   3540
tgaagaggtt tttttttttt ttttttaata gaaactgaag acattttaca accagctatg   3600
acttggtaag acattcttag aattttaggt gtcactgata atcctagaac cactgagccc   3660
caagtgaaga atttaacaac aaaatgggtt aatgaaaaat ataattacat tgtatattta   3720
agtttcatag aattatttaa aacaacacat taaagatttt tctaaaatat agactgcttg   3780
ctttctgtct tagacttacg tttgttgttt ttcagtaatg tgattttctt ttaagttggg   3840
ggttatgcag ggttgtcatt ttgttataac catctaattt ctgcctctgc tgctttaatg   3900
ctaaatgaga tatcaacagc tgacttcata tctcacctgt gagctccctg ctgagttttg   3960
gagggtctgc tcatgggaag aaataggaaa gagcagtgac tatgggcgta cttggaaaga   4020
catggccaag catccccagg tgtgtttcag ttccttttgg ggcatttatt gccatcgttg   4080
cttacaatga ttgacatctt tgtttcttat caaaggattc cagttccact ttctatataa   4140
aatatattgt gatatatcta catatgcctt attacataat tgtgctgaat gctggtaata   4200
tccgcaatgc ctcttgactt taatgggaaa aggcatgcag accagtaagt tccccagtca   4260
cttcagagac tataaaacac tcaaagcatt ttttaaccag ctaggtttaa atctctcata   4320
gagttatgtt taacatcctg agtctgcagt cagttgctgt caagtcgtat aggaatacga   4380
attgtgatca tagatcaaag attttcagag gtccttaaaa ccaactaaat acatgctact   4440
ttaaaatcat tgctatcatg cagaaaagct ctttagacat gaagacagaa ataagtgtta   4500
aatggaacta cataaagctc tttaaagatt atttcttaat ttctactttt tgggagttaa   4560
attaagaaag gaactttata aatgttttgc taccattgta gaacacttca ttaacttttg   4620
tgccatgcta agagtattcg tcttaaacat ttttcaaact ttatgtactt tatgttgtgt   4680
ctcagaactg aataaaatat tgaatttt                                      4708
```

<210> SEQ ID NO 7
<211> LENGTH: 60
<212> TYPE: PRT
<213> ORGANISM: Mus musculus

<400> SEQUENCE: 7

-continued

```
Arg Leu Gly Ala Asp Met Glu Asp Leu Arg Asn Arg Leu Gly Gln Tyr
1               5                   10                  15

Arg Asn Glu Val His Thr Met Leu Gly Gln Ser Thr Glu Glu Ile Arg
            20                  25                  30

Ala Arg Leu Ser Thr His Leu Arg Lys Met Arg Lys Arg Leu Met Arg
        35                  40                  45

Asp Ala Glu Asp Leu Gln Lys Arg Leu Ala Val Tyr
    50                  55                  60


<210> SEQ ID NO 8
<211> LENGTH: 60
<212> TYPE: PRT
<213> ORGANISM: Mus musculus

<400> SEQUENCE: 8

Arg Leu Gly Ala Asp Met Glu Asp Leu Arg Asn Arg Leu Gly Gln Tyr
1               5                   10                  15

Arg Asn Glu Val His Thr Met Leu Gly Gln Ser Thr Glu Glu Ile Arg
            20                  25                  30

Ala Arg Leu Ser Thr His Leu Arg Lys Met Arg Lys Arg Leu Met Arg
        35                  40                  45

Asp Ala Asp Asp Leu Gln Lys Arg Leu Ala Val Tyr
    50                  55                  60
```

TRPC3 AS A THERAPEUTIC TARGET FOR ALZHEIMER'S DISEASE

RELATED APPLICATION

This application claims the benefit under 35 U.S.C. § 119(e) of U.S. provisional application No. 62/770,095, filed Nov. 20, 2018, which is incorporated by reference herein in its entirety.

FEDERALLY SPONSORED RESEARCH

The invention was made with government support under Grant Nos. R01AG054180, R01AG057914, R01DK102918, F31AG050357, awarded by the National Institutes of Health. The government has certain rights in the invention.

BACKGROUND

Alzheimer's disease (AD) is a neurodegenerative disorder characterized by both dementia and the accumulation of neuropathological amyloid plaques and tau tangles. Mutations that drive overproduction of beta-amyloid (Aβ) have been shown to cause early onset familial AD (FAD), leading to a model in which production and accumulation of Aβ is thought to be an initiating event in a sequence leading to memory loss, neurodegeneration, gliosis, and synaptic dysfunction. Strategies to directly target amyloid for clearance have not translated into successful treatments, and the number of deaths attributable to AD as well as costs associated with the disease continue to rise. In addition, even among patients with FAD mutations, the age at first symptom onset is widely variable, with some patients exhibiting symptoms decades later than predicted based on mutation status, suggesting additional genetic factors exist that may provide protection from disease.

SUMMARY

Identifying genes that modify symptoms of Alzheimer's disease (AD) provides novel therapeutic strategies to prevent, treat, cure or delay the onset of AD. To discover genetic modifiers of AD, a mouse model of AD was combined with a genetically diverse reference panel to generate F1 mice harboring identical 'high-risk' human AD mutations but that differ across the remainder of their genome. The present disclosure validates the reference panel as an AD model by demonstrating its high degree of phenotypic, transcriptomic, and genetic overlap with human AD. As genetic variation has been shown to modify the impact of causal human AD mutations, the reference panel and resulting mouse model is an innovative resource for the study of AD. Viral-mediated knockdown was used to functionally validate Trpc3 as a modifier of AD.

Thus, some aspects of the present disclosure provide methods comprising delivering to a subject who has AD an agent that modulates (e.g., decreases) TRPC3 expression and/or activity. In some embodiments, the subject is a human subject.

Other aspects of the present disclosure provide methods comprising administering to an AD mouse model a candidate agent (e.g., that may modulate, e.g., decrease TRPC3 expression and/or activity), and assaying the mouse for an improvement in a symptom of AD and/or assaying the mouse for an adverse effect. In some embodiments, the AD mouse model is an AD-BXD mouse (see, e.g., Neuner S M et al. bio$R_x$iv *Systems genetics identifies modifiers of Alzheimer's disease risk and resilience* (doi.org/10.1101/225714), including Supplemental Materials, herein incorporated by reference in its entirely).

In some embodiments, the agent is delivered in an amount effective to alleviate one or more symptoms of AD. In some embodiments, the agent is delivered in an amount effective to slow or stop progression of AD. In some embodiments, the agent is delivered in an amount effective to improve working memory performance at least 10% compared to the subject's working memory performance prior to delivery of the agent. In some embodiments, the agent reduces the amount of beta-amyloid plaque by at least 40% compared the amount of beta-amyloid plaque prior to administration of the agent.

In some embodiments, the agent is selected from polynucleotides, polypeptides, and small molecule drugs.

Other aspects of the present disclosure provide methods that comprise delivering to a subject an agent that decreases expression of, or decrease activity of, a product encoded by a pathway gene upstream from or downstream from TRPC3, wherein the subject has AD.

Further aspects of the present disclosure provide methods comprising contacting a neuronal cell that expresses TRPC3 with an agent that decreases TRPC3 expression and/or activity.

Still further aspects of the present disclosure provide method for producing a panel of AD-BXD mice, the method comprising breeding female congenic C57BL/6J mice hemizygous for the dominant 5XFAD transgene with genetically diverse recombinant male mice from the BXD genetic reference panel, and producing F1 progeny, wherein the F1 progeny are isogenic recombinant inbred backcross mice, each harboring one maternally derived B allele and either a B or D paternally derived allele at any given genomic locus.

In some embodiments, the TRPC3 comprises an amino acid sequence of any one of SEQ ID NOS: 1-3. In some embodiments, the TRPC3 is encoded by a nucleic acid sequence of any one of SEQ ID NOS: 4-6.

Figure 2A:
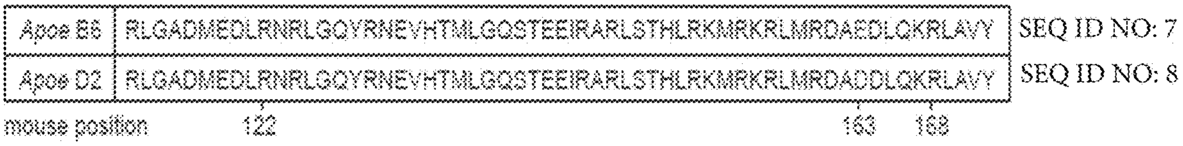
Figure 2B:
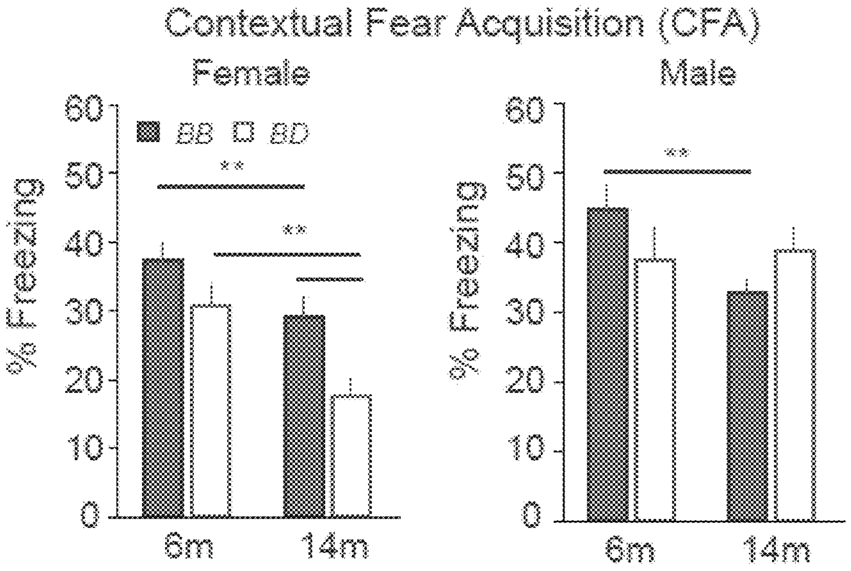
Figure 2C:
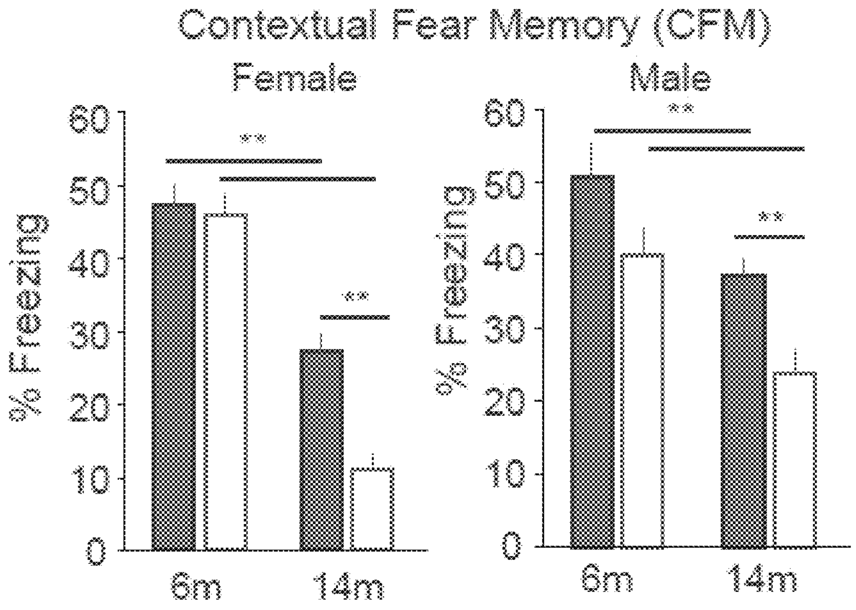

FIGS. 2A-2C: AD-BXD panel is sensitive to variation in known AD risk gene Apoe. (A) The D allele harbors only a single E>D missense SNP at mouse 163 (red). (B) Across AD-BXD mice, there was a significant effect of Apoe allele [F(1, 354)=4.7, p=0.03], age [F(1,354)=12.3, p=0.001], and sex [F(1,354)=17.9, p<0.001] on contextual fear acquisition (CFA). There was a trend toward Apoe having a more significant effect on CFA in females than in males [strain*sex interaction, F(1, 354)=3.2, p=0.08]. (C) Across AD-BXD mice, there was a significant effect of Apoe allele [F(1, 354)=20.9, p<0.001], age [F(1,354)=86.2, p<0.001], sex [F(1, 354)=4.9, p=0.03], and an age by sex interaction [F(1, 354)=7.6, p=0.006] on contextual fear memory (CFM), demonstrating that while strains carrying the D allele at Apoe do indeed perform more poorly on this task, all female AD mice are more susceptible to AD-related cognitive decline as measured by CFM.

FIGS. 3A-3H: Genetic risk score calculated from genotype at known AD risk genes predicts cognitive decline. (A) Strains were stratified into impaired (below population average) and unimpaired (above population average) based 6 m CFM performance. (9) Genetic risk scores (GRS) were calculated for each strain based on allelic composition of 21 genes known to confer risk for AD. The risk allele of each gene was defined as that which appeared more frequently in the impaired population pictured in (A). (C) GRS significantly predicts how a given AD-BXD strain will perform on CFA at 14 m. (D) No relationship between GRS and (TA in 14 m Ntg-BXD mice was observed. (E) No relationship between GRS and non-cognitive traits across ADBXDs including amyloid load at 14 m, (F) 14 m weight, (G) 14 m sensorimotor performance, (H) or anxiety as measured by percent open entries on the elevated plus maze was observed.

Figure 4A:
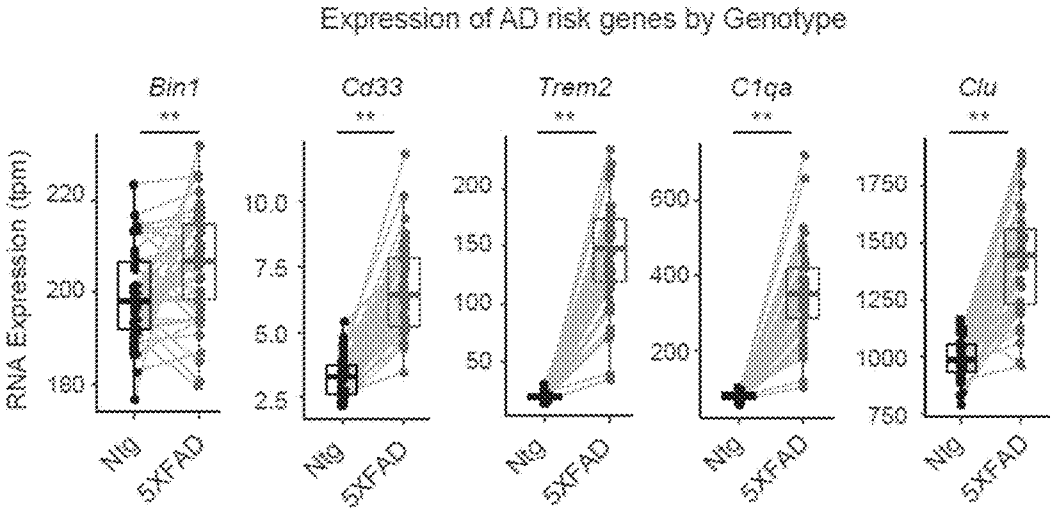
Figure 4B:
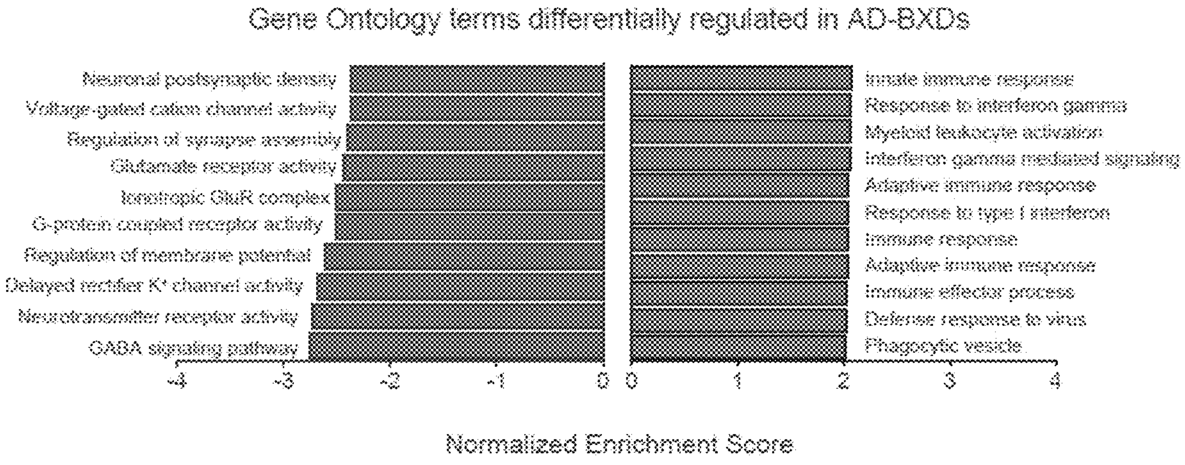

FIGS. 4A-4B: Genetic background modifies AD-associated transcriptome. (A) Genes known to be associated with AD are differentially expressed in our panel, n=132 mice (65 females/67 males across 15 strains). Each point represents a single genotype/strain/age/sex averaged sample, **p<0.05 two-tailed t-test. (B) List of top gene ontology (GO) functional categories enriched among genes (left) downregulated and (right) upregulated in all ADBXDs relative to all Ntg-BXDs.

Figure 5A:
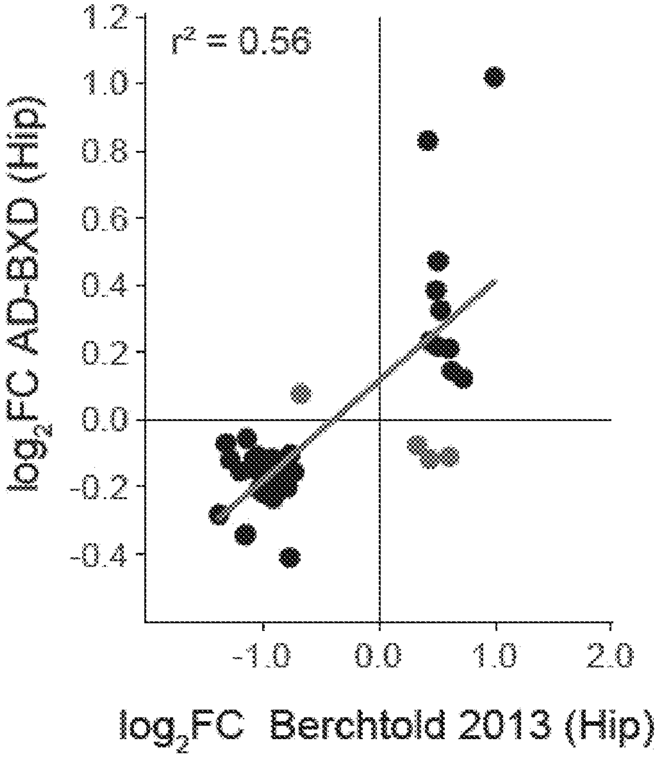
Figure 5B:
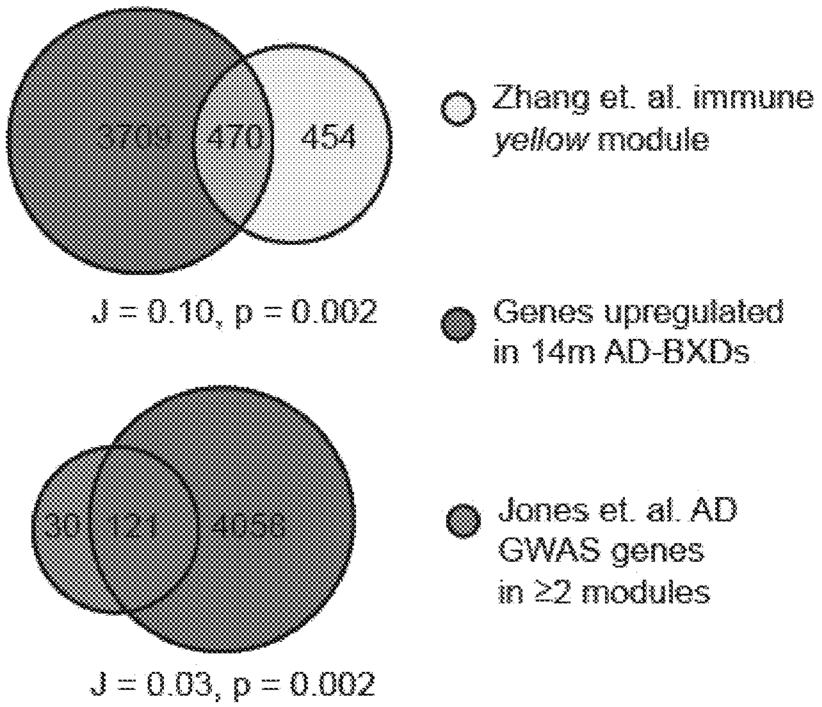
Figure 5C:
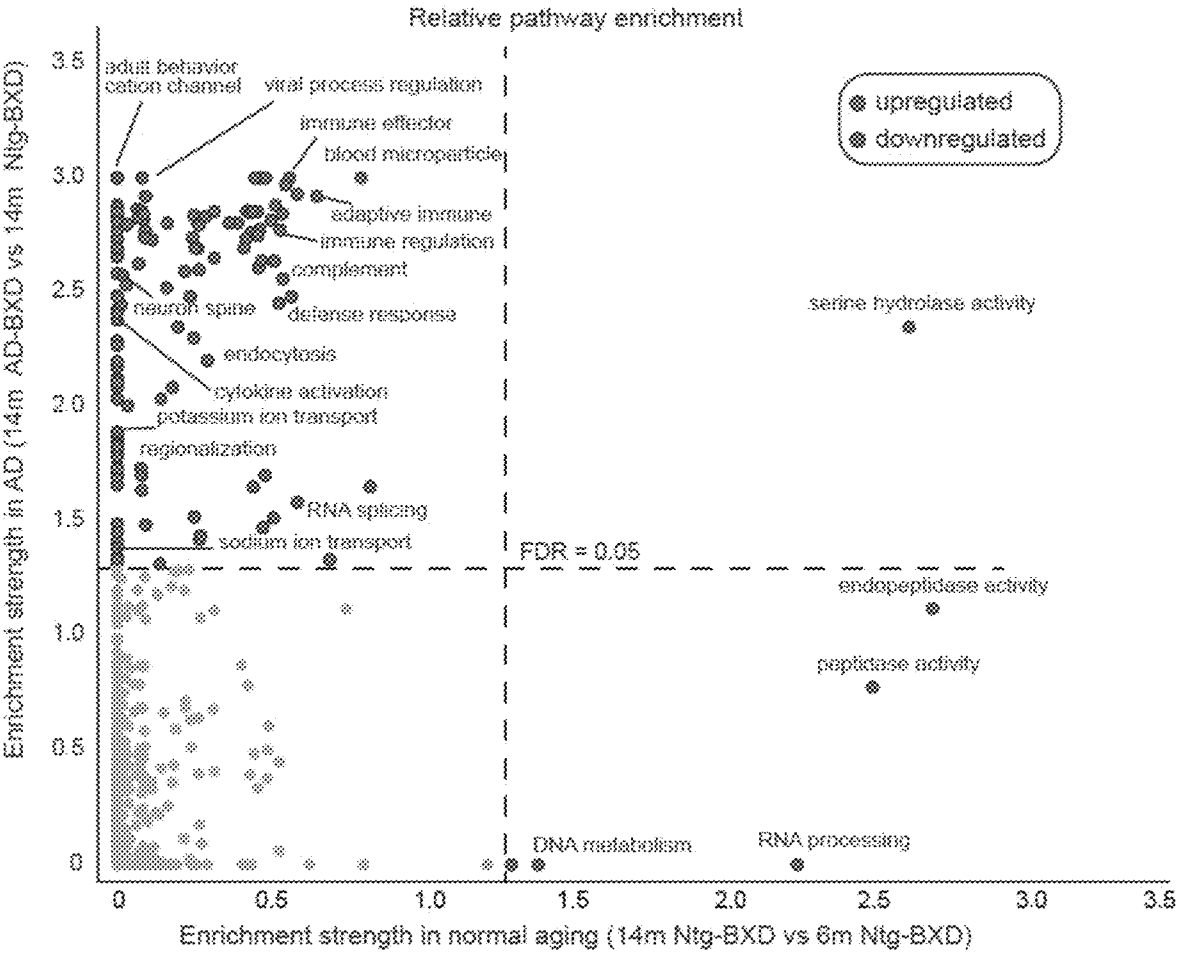

FIGS. 5A-5C: Aged AD-BXD transcriptome shows high concordance with late-onset human AD signature. (A) 39 out of 60 (65%) of AD signature genes identified by and Blalock (Hargis and Blalock, 2017) show concordant significant changes in expression across mouse and human transcriptomes. The log 2 fold change (FC) of significantly differentially expressed genes between 14 m AD- and Ntg-BXDs is plotted on the y-axis, while the log 2FC of gene expression between human AD patients and controls from study by a study by Berchtold and colleagues (Berchtold et al., 2013) is plotted on the x-axis. Each point represents a single gene; discordant genes with log 2 fold changes with opposite direction have been highlighted in red. (B) Genes upregulated in 14 m AD-BXDs relative to Ntg-BXDs were compared to genes associated with human AD by (top) Zhang and colleagues (Zhang et 2013) and (bottom) Jones and colleagues (International Genomics of Alzheimer's Disease, 2015). A significant overlap was identified in both cases. (C) Graph of enrichment strength of gene ontology (GO) categories across (y-axis) mouse AD or (xaxis) normal aging. Gene set enrichment analysis was performed on genes identified to be differentially expressed relative to 5XFAD carrier status or normal aging in Ntg-BXDs (data not shown). For GO terms that were identified in both scenarios, the FDR q-values were transformed to obtain a measure of enrichment strength and scores were plotted against each other to identify unique and/or common differentially regulated GO terms. As such, each axis can be thought of significance; the upper left quadrant highlights pathways that are uniquely significantly altered in AD-BXDs relative to Ntg-BXDs, while the bottom right quadrant highlights pathways that are uniquely significantly altered in normal aging (14 m Ntg-BXDs vs 6 m Ntg-BXDs). Data points are colored based on directionality of enrichment score calculated by GSEA: red=genes belonging to this category were significantly upregulated in given scenario, blue=genes belonging to this category were significantly downregulated in given scenario. Dotted lines represent, enrichment scores for FDR q-value=0.05.

FIGS. 6A-6G show that knockdown of candidate Trpc3 delays AD symptoms in a mouse model of AD. (A) TRPC3 protein is increased in the hippocampus of 5XFAD mice as measured by Western blot [n=4/grp, t(1,6)=3.74, p=0.01]. (B) AAV9 encoding either shRNA targeting Trpc3 (shRNA-Trpc3) or a scrambled control shRNA (shRNA-Ctrl) was delivered bilaterally into the hippocampus of presymptomatic 4 month-old 5XFAD mice. Working memory was assessed on the y-maze at 9 months while CFM was assessed at 10 months. (C) There was a significant effect of group on working memory [F(2, 28)=10.6, p<0.001], with 5XFAD shRNA-Ctrl mice exhibiting impairment relative to both Ntg shRNA-Ctrl mice [post-hoc t-test, t(1,18)=4.4, p<0.001] and 5XFAD shRNA-Trpc3 mice [01,18)=2.2, p=0.04]. (D) Left, all mice exhibited similar levels of freezing after the final training shock, indicating comparable acquisition across groups [F(2,26)=1.1, p>0.3]. Right, there was a significant effect of group on CFM [F(2,26)=3.4, p=0.05]. 5XFAD shRNA-Ctrl mice exhibited impairment relative to both Ntg shRNA-Ctrl mice [01,17)=2.3, p=0.03] and 5XFAD shRNA-Trpc3 mice [01,18)=2.1, p=0.047], who performed comparably (p>0.05). (E) Left, representative 2× images of coronal brain sections from 10 month 5XFAD mice. The levels function in Photoshop was used identically across all images to increase visibility. (F) There was a significant effect of group on number of Aβ42 immunoreactive plaques in the hippocampus and cortex [F(2,11)=5.5, p=0.03]. 5XFAD shRNA-Trpc3 mice showed a decrease in the number of plaques in the hippocampus and cortex compared to 5XFAD shRNA-Ctrl mice [one-tailed t-test, t(1,7)=2.0, p=0.04] and were not significantly different than Ntg mice [t(1,6)=1.8, p=0.12). (G) A significant association was observed between TRPC3 expression in the prefrontal cortex and a measure of brain-wide amyloid burden in neuritic plaque positive human AD cases (p=0.0005).

Figure 7A:
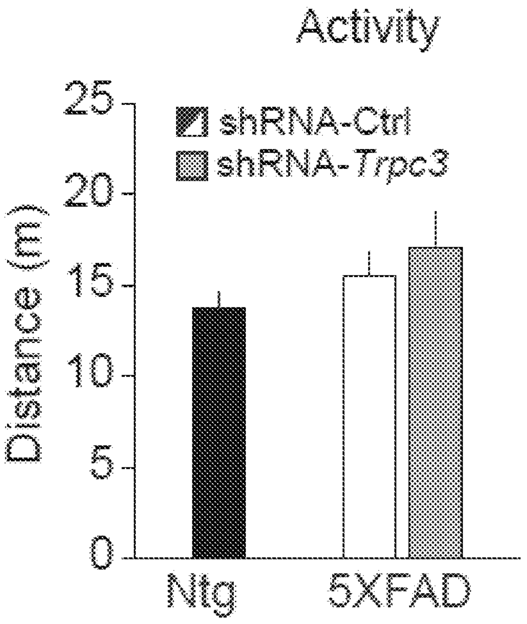
Figure 7B:
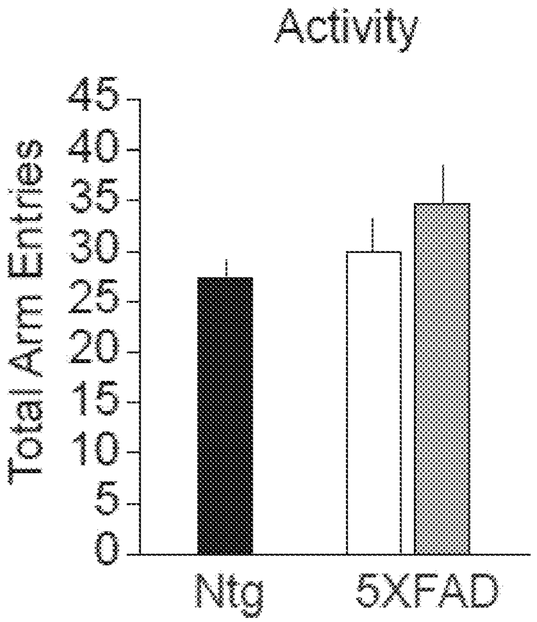
Figure 7C:
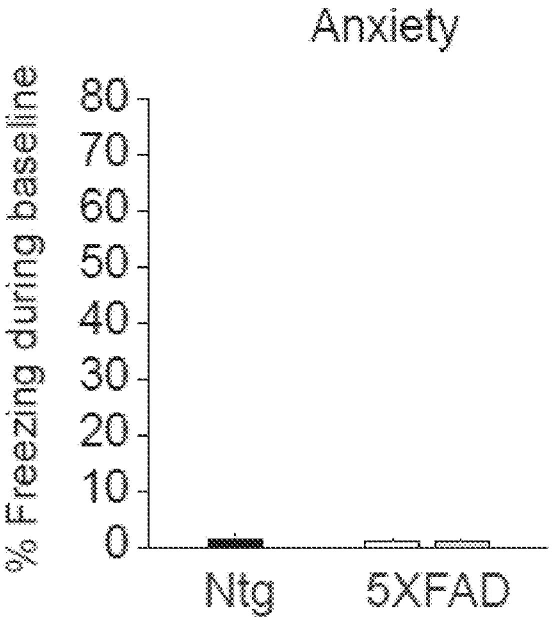

FIGS. 7A-7C show that knockdown of Trpc3 does not have non-specific effects on activity or anxiety. (A) There was no main effect of group on distance travelled in the Y-maze [F(2, 28)=0.74, p>0.40]. (B) There was also no main effect of group on total arms entered in the Y-maze [F(2, 28)=0.29, p>0.75]. (C) There was no main effect of group on baseline freezing prior to any foot shocks during contextual fear conditioning training [F(2, 26)=0.10, p>0.90].

Figure 8A:
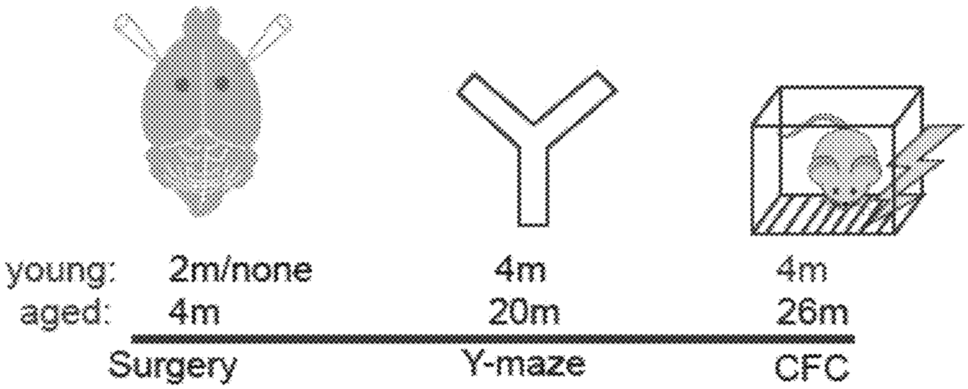
Figure 8B:
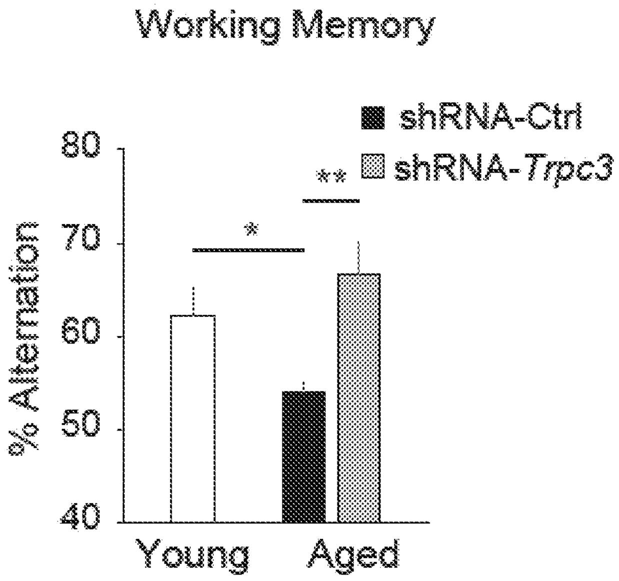
Figure 8C:
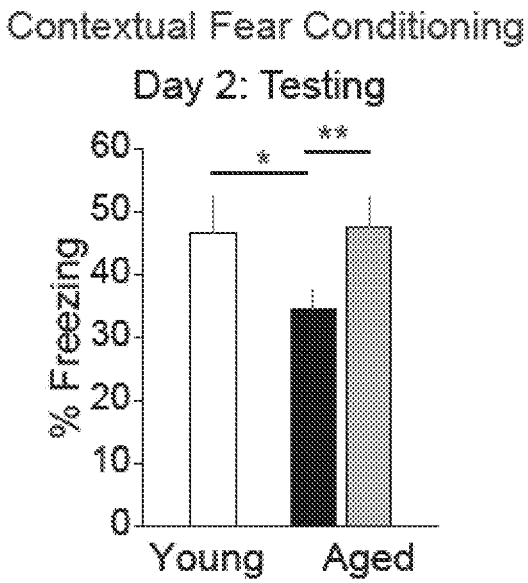

FIGS. 8A-8C show that knockdown of Trpc3 delays cognitive aging in non-transgenic mice. (A) Two cohorts of mice were used in this study. For the aged cohort, AAV9 encoding either shRNA targeting Trpc3 (shRNA-Trpc3) or a scrambled control shRNA (shRNA-Ctrl) was delivered bilaterally into the hippocampus of young 4 month-old Ntg-B6J mice. Working memory was assessed on the Y-maze at 20 months (20 m) while CFM was assessed at 26 m. The young cohort consisted of Ntg-B6J mice that received surgery at 2 months old (or no surgery controls) and was cognitively assessed at 4 months of age and fear-conditioned concurrently with the aged cohort. (B) Aged mice that received control injections exhibited significantly impaired working memory as compared to young controls [t(1,15)=3.2, p=0.005]. However, aged mice that received injections of shRNA-Trpc3 were not impaired [t(1,13)=0.8, p=0.4] relative to controls and performed significantly better than aged mice that received control injections [t(1, 20)=3.7, p=0.002]. (C) Aged mice that received control injections exhibited significantly impaired contextual fear memory relative to young controls [one-tailed t-test, t(1, 37)=1.9, p=0.03]. However, aged mice that received injections of shRNA-Trpc3 were not impaired [t(1, 31)=0.1, p=0.9] and performed significantly better than aged control mice [t(1, 38)=2.2, p=0.03].

DETAILED DESCRIPTION

Alzheimer's disease (AD) is a neurodegenerative disorder characterized by both dementia and the accumulation of neuropathological amyloid plaques and tau tangles. Mutations that drive overproduction of beta-amyloid (Aβ) have been shown to cause early onset familial AD (FAD), leading to a model in which production and accumulation of Aβ is thought to be an initiating event in a sequence leading to memory loss, neurodegeneration, gliosis, and synaptic dysfunction. However, strategies to directly target amyloid for clearance have failed to translate into successful treatments and the number of deaths attributable to AD and costs associated with the disease continue to rise.

A goal of mouse studies relating to AD is the eventual translation of identified candidates into viable human therapeutics or biomarkers of disease. Thus, mouse models harboring causal AD mutations are important tools that present many advantages including defined high-risk genotypes, early access to brain tissue, and precise environmental control. The AD-BXD panel, the first AD transgenic mouse reference panel, is a valuable resource that demonstrates high levels of overlap between the AD-BXD mice and human AD at the phenotypic, transcriptomic, and genetic level. This panel combines two well-established resources: (1) the 5XFAD transgenic line on an otherwise fully inbred C57BL/6J (B6) background that recapitulates various aspects of the human disease, including amyloid-β42 accumulation, cognitive deficits, and neuron loss (Oakley et al., *The Journal of Neuroscience,* 26: 10129-10140 (2006)), and (2) the BXD genetic reference panel, the largest and best-characterized series of recombinant inbred strains derived from the two common inbred strains B6 and DBA/2J (D2) (Peirce et al., *BMC genetics* 5: 7 (2004); Taylor et al., *Mamm Genome* 10: 335-348 (1999)). The BXD panel segregates for more than 4.8 million sequence variants, including many in genes known to confer risk for AD (Wang et al., *Nat Commun* 7: 10464 (2016)). The resulting panel of F1 hybrids represent a novel and fully isogenic resource to monitor phenotypic outcomes in individuals harboring identical high-risk FAD mutations in human APP and PSEN1 genes, raised in controlled environments, but whose allelic contributions differ across the remainder of the genome.

Trpc3 was identified as a candidate modifier of cognitive deficits and amyloid pathology, and viral-mediated knockdown was used to functionally validate Trpc3 as a modifier of AD. In addition to its utility as a potential biomarker, Trpc3 may be targeted mechanistically to treat disease. The translational relevance of this idea is supported by the association identified herein between levels of TRPC3 in human patients and a measure of brain-wide amyloid burden. The discovery of the differences in gene expression between human subjects with and without AD may provide new insight into the prevention and treatment of AD. Further, therapeutics, such as the agents described herein, may focus on Trpc3 or targets/cellular mechanisms that exist upstream and/or downstream of Trpc3 itself.

In some aspects, the present disclosure provide methods of contacting a neuronal cell (neuron) with an agent that decreases the expression of TRPC3 or the activity of TRPC3 (decreases TRPC3 expression and/or activity), a protein identified herein as present at different levels in the hippocampal region of an AD mouse model. Other aspects of the present disclosure provide methods of delivering to a subject having AD, suspected of having AD, or at risk of developing AD, an agent that decreases the expression of TRPC3 or the activity of TRPC3.

Contacting a neuronal cell with an agent includes exposing a neuronal cell (e.g., in vivo or in vitro) to an agent (e.g., a therapeutic agent) such that the neuronal cell comes into physical contact with the agent. For example, the step of contacting a neuronal cell with an agent may include delivering the agent to a composition that includes the neuronal cell, and/or delivering the neuronal cell to a composition that includes the agent. A neuronal cell may also be contacted by an agent when the agent is delivered to a subject in which the neuronal cell is present (e.g., brain).

Delivery of an agent to a subject may be by any route known in art. For example, delivery of the agent may be intravenous (e.g., viral vectors, exosomes), intranasal, intramuscular, intrathecal, or subcutaneous. Other delivery routes may be used.

An agent, in some embodiments, is a therapeutic agent and/or a prophylactic agent. An agent may be a biomolecule or a chemical agent. In some embodiments, an agent is a polynucleotide (e.g., double-stranded or single-stranded DNA or RNA, such as a guide RNA (gRNA) (e.g., in combination with Cas9), messenger RNA (mRNA), or an RNA interference (RNAi) molecule, such as antisense RNA, small interfering RNAs (siRNAs), short hairpin RNAs (shRNAs), and/or microRNAs (miRNAs)). In some embodiments, an agent is a polypeptide (e.g., protein and/or peptide). Non-limiting examples of polypeptides include antibodies (e.g., monoclonal antibodies and/or antibody fragments, such as single change variable fragments (scFvs)). An agent, in some embodiments, is a cellular agent, such as a stem cell (e.g., pluripotent stem cell, such as an induced pluripotent stem cell). In some embodiments, an agent is small molecule drug (e.g., chemical compound).

An agent is considered to decrease expression of a gene (e.g., TRPC3) if expression of the gene is decreased following exposure of the agent to a neuronal cell comprising the gene. In some embodiments, the change in gene expression is relative to a control, such as gene expression from a neuronal cell not exposed to the agent. In some embodiments, an agent decreases expression of a gene by at least 10%, at least 20%, at least 30%, at least 40%, at least 50%, at least 60%, at least 70%, at least 80%, at least 90%, or at least 100% (e.g., by 10%-100%), relative to a control.

Likewise, an agent is considered to decrease activity of a product (e.g., protein, such as TRPC3 protein) encoded by a gene if activity of the product is decreased following exposure of the agent to a neuronal cell comprising the gene encoding the protein. In some embodiments, the change in activity is relative to a control, such as activity in a neuronal cell not exposed to the agent. In some embodiments, an agent decreases activity of a product by at least 10%, at least 20%, at least 30%, at least 40%, at least 50%, at least 60%, at least 70%, at least 80%, at least 90%, or at least 100% (e.g., by 10%-100%), relative to a control.

In some embodiments, an agent decreases expression of a gene (e.g., TRPC3) by at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold (e.g., 1.5 fold-20-fold).

Neuronal cells (e.g., human neuronal cells or rodent neuronal cells) include neurons. Other brain cell types are encompassed by the present disclosure, including, for example, neuroglia (e.g., oligodendrocytes, microglia, and astrocytes). Examples of neuronal cells include Purkinje cells, granule cells, motor neurons, tripolar neurons, pyramidal cells, chandelier cells, spindle neurons, and stellate cells. In some embodiments, a neuronal cell (neuron) is present in the hippocampus (e.g., hippocampal long spines), cortex, or cerebellum. Neurons of the present disclosure, in some embodiments, are used to test the function of an agent (e.g., in vitro), for example, the extent to which (if any) and agent modifies (e.g., decreases) expression of a gene or activity of a product encoded by a gene as provide herein. Thus, in some embodiments, neurons (e.g., in vitro or in an in vivo mouse model) may be modified (e.g., genomically modified) to express or under-express (e.g., knock out or knockdown) expression of TRPC3 (or upstream or downstream genes) as provided herein.

A subject may be a human subject or a rodent (e.g., a mouse model). In some embodiments, the subject is a transgenic mouse that expresses or under-expresses (e.g., knocks out or knocks down) expression of TRPC3 (or upstream or downstream genes) as provided herein. In some embodiments, the subject is a human subject, for example, a subject having or suspected of having (e.g., diagnosed with and/or exhibits symptoms of) or at risk of developing (e.g., has one or more risk factors) Alzheimer's disease.

Alzheimer's Disease

In some aspects, the present disclosure provides a method of delivering to a subject having Alzheimer's disease (AD), an agent that modifies the expression of TRPC3. AD is a disorder of the brain. Manifestations of AD include abnormal structure(s), function(s), or other process(es) in the brain. AD is the most common form of dementia, a term that encompasses memory loss and other intellectual abilities series enough to interfere with the activities of daily life.

Management of AD includes maintaining quality of life, maximizing function in daily activities, enhancing cognition/mood/behavior, fostering a safe environment, and promoting social engagement. While there is no cure for AD, medications and various management strategies are used to temporarily improve symptoms and to slow the progression of the disease. Medications that may be used are directed to cognitive enhancement (e.g., improving mental function, lowering blood pressure, and balancing mood), and include Donepezil, Galantamine, Memantine, and Rivastigmine. Any of the foregoing medications may be used in combination with agents that increase TRPC3 expression and/or activity.

AD results from changing brain chemistry, for example changes in neurons. As the disease progresses, neurons throughout the brain decrease in size and number of synaptic connections, and the resulting reduction in synaptic density is particularly detrimental to cognitive function. The population of neurons also decreases. AD is further characterized by a loss of synapses and neurons in the cerebral cortex and other areas of the brain, as well as the accumulation of extracellular protein-containing deposits (amyloid plaques) and neurofibrillary tangles (tau tangles). Plaques are dense deposits of beta-amyloid peptide and cellular material located outside and around neurons. Tangles comprise aggregates of microtubule-associated tau protein. The tau protein becomes hyperphosphorylated and accumulates within the neurons themselves. The neurons impacted by the plaques and tangles then lose their respective synaptic connections with other neurons, and may die. Thus, in some embodiments, neurons of the cerebral cortex are contacted with an agent that decreases TRPC3 expression and/or activity, for example, in an amount that reduces accumulation of beta-amyloid peptide and/or tau protein.

Symptoms of AD include decreases in cognitive function, such as decreases in processing speed (e.g., speed at which cognitive activities are performed, speed of motor responses), attention (e.g., ability to concentrate and focus on specific stimuli), memory (e.g., episodic memory, semantic memory), visuospatial constructions, and executive functioning (e.g., the ability to engage in independent, appropriate, purposive behavior). Other symptoms of AD include behavioral changes (e.g., aggression, agitation, difficulty with self-care, irritability, personality changes, restlessness, lack of restrain, wandering, becoming lost), mood changes (e.g., anger, apathy, general discontent, loneliness, mood swings), psychological changes (e.g., depression, hallucinations, paranoia), as well as several miscellaneous symptoms, including the inability to combine muscle movements, jumbled speech, and loss of appetite. Risk factors for AD, in addition to age and heritability factors, may include diabetes, mid-life obesity, mid-life hypertension, hyperlipidemia, smoking status, diet, physical activity, alcohol consumption, cognitive training, social engagement, traumatic brain injury, depression, and lack of sleep.

In some embodiments, a subject of the present disclosure exhibits one or more symptoms and/or risk factors of AD.

Treatment of AD includes, in some embodiments, alleviating one or more symptoms of AD. Alleviation of AD refers to the process of making the symptoms of AD less intense and/or more bearable. Treatment of AD includes, in some embodiments, alleviating symptoms of cognitive decline. In some embodiments, an agent is delivered in an amount effective to alleviate one or more symptoms of AD. In some embodiments, an agent is delivered in an amount effective to slow or stop progression of AD.

Working memory, the capacity to simultaneously manipulate information while maintaining other information, is impaired in subjects with AD. A number of different working memory tests are available and known in the art, for example, the complex span paradigm (Daneman, 1980) and its numerous variations. In some embodiments, an agent is delivered an amount effective to improve working memory performance by at least 10% compared to the subject's working memory performance prior to delivery of the agent (e.g., within 1 week to 3 months prior). In some embodiments, an agent improves working memory performance by at least 5%, at least 10%, at least 20%, at least 30%, at least 40%, at least 50%, at least 60%, at least 70%, at least 80%, at least 90%, or at least 100% (e.g., by 10%-100%), subject's working memory performance prior to delivery of the agent.

In some embodiments, an agent improves working memory performance by at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold (e.g., 1.5 fold-20-fold), relative to the subject's working memory performance prior to delivery of the agent.

In some embodiments, an agent is delivered in an amount effective to reduce the amount of beta-amyloid plaque by at least 40% compared to the amount of beta-amyloid plaque prior to administration of the agent. In some embodiments, an agent reduces the amount of beta-amyloid plaque by at least 20%, at least 30%, at least 40%, at least 50%, at least 60%, at least 70%, at least 80%, at least 90%, or at least 100% (e.g., by 20%-100%), relative to the amount beta-amyloid plaque prior to administration of the agent.

In some embodiments, an agent reduces the amount of beta-amyloid plaque in a subject by at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold (e.g., 1.5 fold-20-fold), relative to the amount beta-amyloid plaque prior to administration of the agent. For an example blood test to detect plaques in the brain, see, e.g., newscientist.com/article/2141198-blood-test-detects-alzheimers-plaques-building-up-in-brain). Magnetic resonance imaging (MRI) may also be used.

In some aspects, neurons of a subject having AD exhibit aberrant expression (e.g., increased expression) of TRPC3 compared to a subject not having AD (e.g., an age-matched naïve subject).

TRPC3

In some aspects, the present disclosure provides methods of delivering to a neuronal cell (neuron) or to a subject (e.g., having AD or at risk of AD) an agent that modifies the expression of TRPC3 or the activity of a product (e.g., TRPC3 protein) encoded by TRPC3 differentially expressed by neurons, as provided herein. The transient receptor potential cation channel subfamily C member 3 (TRPC3) (Gene ID: 7222) encodes the TRPC3 protein. The TRPC3 protein is a membrane protein that can form a non-selective channel permeable to cations, such as calcium. The protein may be induced to form channels in conditions of low intracellular calcium stores and/or by a receptor tyrosine kinase-activated phosphatidylinositol second messenger system or G-protein coupled receptors. Together with TRPC6 and TRPC7, TRPC3 is implicated in the regulation of vascular tone, cell growth, proliferation, and pathological hypertrophy. As described herein, increases in TRPC3 are associated with amyloid load and AD-related cognitive symptoms in a mouse model of AD. Thus, increased levels of TRPC3 expression and/or activity may be indicative of AD.

In some embodiments, the TRPC3 is a human TRPC3 (hTRPC3). Non-limiting examples of hTRPC3 proteins of the present disclosure include an hTRPC3 protein comprising an amino acid sequence of SEQ ID NO: 1 and/or encoded by a nucleic acid sequence of SEQ ID NO: 4 (e.g., UniProt Q13507-2; GenBank NP_001124170.1/NM_001130698.1), an hTRPC3 protein comprising an amino acid sequence of SEQ ID NO: 2 and/or encoded by a nucleic acid sequence of SEQ ID NO: 5 (e.g., UniProt Q13507-3; NP_003296.1/NM_003305.2), and an hTRPC3 protein comprising an amino acid sequence of SEQ ID NO: 3 and/or encoded by a nucleic acid sequence of SEQ ID NO: 6 (NP_001353408.1/NM_001366479.1). In some embodiments, an agent modifies an hTRPC3 that comprises an amino acid sequence of SEQ ID NO: 1 and/or is encoded by a nucleic acid sequence of SEQ ID NO: 4. In some embodiments, an agent modifies an hTRPC3 that comprises an amino acid sequence of SEQ ID NO: 2 and/or is encoded by a nucleic acid sequence of SEQ ID NO: 5. In some embodiments, an agent modifies an hTRPC3 that comprises the amino acid sequence of SEQ ID NO: 3 and/or is encoded by a nucleic acid sequence of SEQ ID NO: 6.

Thus, in some embodiments, provided herein are methods of delivering to a neuronal cell (neuron) or to a subject (e.g., having AD or at risk of AD) an agent that modifies the expression of TRPC3 or the activity of a product (e.g., TRPC3 protein) encoded by TRPC3, wherein the TRPC3 comprises a nucleic acid sequence of any one of SEQ ID NOS: 4-6 or encodes a TRPC3 protein comprising an amino acid sequence of any one of SEQ ID NOS: 1-3.

GenBank NP_001124170.1 (TRPC3 long form; 921 amino acids)

(SEQ ID NO: 1)

MSTKVRKCKEQARVTFPAPEEEEDEGEDEGAEPQRRRRGWRGVNGGLEPRSAPSQREPHGYCPPPFSHGPDLSMEGSPSLRR

MTVMREKGRRQAVRGPAFMFNDRGTSLTAEEERFLDAAEYGNIPVVRKMLEESKTLNVNCVDYMGQNALQLAVGNEHLEVTE

LLLKKENLARIGDALLLAISKGYVRIVEAILNHPGFAASKRLTLSPCEQELQDDDFYAYDEDGTRFSPDITPIILAAHCQKY

EVVHMLLMKGARIERPHDYFCKCGDCMEKQRHDSFSHSRSRINAYKGLASPAYLSLSSEDPVLTALELSNELAKLANIEKEF

-continued

KNDYRKLSMQCKDFVVGVLDLCRDSEEVEAILNGDLESAEPLEVHRHKASLSRVKLAIKYEVKKFVAHPNCQQQLLTIWYEN

LSGLREQTIAIKCLVVLVVALGLPFLAIGYWIAPCSRLGKILRSPFMKFVAHAASFIIFLGLLVFNASDRFEGITTLPNITV

TDYPKQIFRVKTTQFTWTEMLIMVWVLGMMWSECKELWLEGPREYILQLWNVLDFGMLSIFIAAFTARFLAFLQATKAQQYV

DSYVQESDLSEVTLPPEIQYFTYARDKWLPSDPQIISEGLYAIAVVLSFSRIAYILPANESFGPLQISLGRTVKDIFKFMVL

FIMVFFAFMIGMFILYSYYLGAKVNAAFTTVEESFKTLFWSIFGLSEVTSVVLKYDHKFIENIGYVLYGIYNVTMVVVLLNM

LIAMINSSYQEIEDDSDVEWKFARSKLWLSYFDDGKTLPPPFSLVPSPKSFVYFIMRIVNFPKCRRRRLQKDIEMGMGNSKS

RLNLFTQSNSRVFESSFNSILNQPTRYQQIMKRLIKRYVLKAQVDKENDEVNEGELKEIKQDISSLRYELLEDKSQATEELA

ILIHKLSEKLNPSMLRCE

GenBank NP_003296.1 (TRPC3 short form; 848 amino acids)

(SEQ ID NO: 2)

MEGSPSLRRMTVMREKGRRQAVRGPAFMFNDRGTSLTAEEERFLDAAEYGNIPVVRKMLEESKTLNVNCVDYMGQNALQLAV

GNEHLEVTELLLKKENLARIGDALLLAISKGYVRIVEAILNHPGFAASKRLTLSPCEQELQDDDFYAYDEDGTRFSPDITPI

ILAAHCQKYEVVHMLLMKGARIERPHDYFCKCGDCMEKQRHDSFSHSRSRINAYKGLASPAYLSLSSEDPVLTALELSNELA

KLANIEKEFKNDYRKLSMQCKDFVVGVLDLCRDSEEVEAILNGDLESAEPLEVHRHKASLSRVKLAIKYEVKKFVAHPNCQQ

QLLTIWYENLSGLREQTIAIKCLVVLVVALGLPFLAIGYWIAPCSRLGKILRSPFMKFVAHAASFIIFLGLLVFNASDRFEG

ITTLPNITVTDYPKQIFRVKTTQFTWTEMLIMVWVLGMMWSECKELWLEGPREYILQLWNVLDFGMLSIFIAAFTARFLAFL

QATKAQQYVDSYVQESDLSEVTLPPEIQYFTYARDKWLPSDPQIISEGLYAIAVVLSFSRIAYILPANESFGPLQISLGRTV

KDIFKFMVLFIMVFFAFMIGMFILYSYLGAKVNAAFTTVEESFKTLFWSIFGLSEVTSVVLKYDHKFIENIGYVLYGIYNVT

MVVVLLNMLIAMINSSYQEIEDDSDVEWKFARSKLWLSYFDDGKTLPPPFSLVPSPKSFVYFIMRIVNFPKCRRRRLQKDIE

MGMGNSKSRLNLFTQSNSRVFESHSFNSILNQPTRYQQIMKRLIKRYVLKAQVDKENDEVNEGELKEIKQDISSLRYELLED

KSQATEELAILIHKLSEKLNPSMLRCE

GenBank NP_001353408.1 (TRPC3 C-terminal split; 893 amino acids)

(SEQ ID NO: 3)

MSTKVRKCKEQARVTFPAPEEEEDEGEDEGAEPQRRRRGWRGVNGGLEPRSAPSQREPHGYCPPPFSHGPDLSMEGSPSLRR

MTVMREKGRRQAVRGPAFMFNDRGTSLTAEEERFLDAAEYGNIPVVRKMLEESKTLNVNCVDYMGQNALQLAVGNEHLEVTE

LLLKKENLARIGDALLLAISKGYVRIVEAILNHPGFAASKRLTLSPCEQELQDDDFYAYDEDGTRFSPDITPIILAAHCQKY

EVVHMLLMKGARIERPHDYFCKCGDCMEKQRHDSFSHSRSRINAYKGLASPAYLSLSSEDPVLTALELSNELAKLANIEKEF

KNDYRKLSMQCKDFVVGVLDLCRDSEEVEAILNGDLESAEPLEVHRHKASLSRVKLAIKYEVKKFVAHPNCQQQLLTIWYEN

LSGLREQTIAIKCLVVLVVALGLPFLAIGYWIAPCSRLGKILRSPFMKFVAHAASFIIFLGLLVFNASDRFEGITTLPNITV

TDYPKQIFRVKTTQFTWTEMLIMVWVLGMMWSECKELWLEGPREYILQLWNVLDFGMLSIFIAAFTARFLAFLQATKAQQYV

DSYVQESDLSEVTLPPEIQYFTYARDKWLPSDPQIISEGLYAIAVVLSFSRIAYILPANESFGPLQISLGRTVKDIFKFMVL

FIMVFFAFMIGMFILYSYYLGAKVNAAFTTVEESFKTLFWSIFGLSEVTSVVLKYDHKFIENIGYVLYGIYNVTMVVVLLNM

LIAMINSSYQEIEDDSDVEWKFARSKLWLSYFDDGKTLPPPFSLVPSPKSFVYFIMRIVNFPKCRRRRLQKDIEMGMGNSKS

RQIMKRLIKRYVLKAQVDKENDEVNEGELKEIKQDISSLRYELLEDKSQATEELAILIHKLSEKLNPSMLRCE

GenBank NM_001130698.1 (TRPC3 long form; 3548 nucleotide base pairs)

(SEQ ID NO: 4)

gggaagactg cactgccgcg aaggcggagg aggccggcag ccggcacccc cacactcgga ccgcagccgg cgcgatgtcc accaaggtca ggaagtgcaa agaacaagca agggtgacct tcccggcgcc ggaggaggag gaagacgagg gcgaggacga gggcgcggag ccgcagcgcc gccgccgggg ctggaggggc gtcaacgggg ggctggagcc gcgctcggcg ccctcgcagc gggagccgca cggctactgc ccgccgccct tctcccacgg gccggacctg tccatggagg gaagcccatc cctgagacgc atgacagtga tgcgggagaa gggccggcgc caggctgtca ggggcccggc cttcatgttc aatgaccgcg gcaccagcct caccgccgag gaggagcgct tcctcgacgc cgccgagtac ggcaacatcc cagtggtgcg caagatgctg gaggagtcca agacgctgaa cgtcaactgc gtggactaca tgggccagaa cgcgctgcag ctggctgtgg gcaacgagca cctggaggtg -continued accgagctgc tgctcaagaa ggagaacctg gcgcgcattg gcgacgccct gctgctcgcc atcagcaagg gctacgtgcg
catcgtagag gccatcctca accaccctgg cttcgcggcc agcaagcgtc tcactctgag cccctgtgag caggagctgc
aggacgacga cttctacgct tacgacgagg acggcacgcg cttctcgccg gacatcaccc ccatcatcct ggcggcgcac
tgccagaaat acgaagtggt gcacatgctg ctgatgaagg gtgccaggat cgagcggccg cacgactatt tctgcaagtg
cggggactgc atggagaagc agaggcacga ctccttcagc cactcacgct cgaggatcaa tgcctacaag gggctggcca
gcccggctta cctctcattg tccagcgagg acccggtgct tacggcccta gagctcagca acgagctggc caagctggcc
aacatagaga aggagttcaa gaatgactat cggaagctct ccatgcaatg caaagacttt gtagtgggtg tgctggatct
ctgccgagac tcagaagagg tagaagccat tctgaatgga gatctggaat cagcagagcc tctggaggta cacaggcaca
aagcttcatt aagtcgtgtc aaacttgcca ttaagtatga agtcaaaaag tttgtggctc atcccaactg ccagcagcag
ctcttgacga tctggtatga gaacctctca ggcctaaggg agcagaccat agctatcaag tgtctcgttg tgctggtcgt
ggccctgggc cttccattcc tggccattgg ctactggatc gcaccttgca gcaggctggg gaaaattctg cgaagccctt
ttatgaagtt tgtagcacat gcagcttctt tcatcatctt cctgggtctg cttgtgttca atgcctcaga caggttcgaa
ggcatcacca cgctgcccaa tatcacagtt actgactatc ccaaacagat cttcagggtg aaaaccaccc agtttacatg
gactgaaatg ctaattatgg tctgggttct tggaatgatg tggtctgaat gtaaagagct ctggctggaa ggacctaggg
aatacatttt gcagttgtgg aatgtgcttg actttgggat gctgtccatc ttcattgctg ctttcacagc cagattccta
gctttccttc aggcaacgaa ggcacaacag tatgtggaca gttacgtcca agagagtgac ctcagtgaag tgacactccc
accagagata cagtatttca cttatgctag agataaatgg ctcccttctg accctcagat tatatctgaa ggcctttatg
ccatagctgt tgtgctcagc ttctctcgga ttgcgtacat cctccctgca aatgagagct ttggccccct gcagatctct
cttggaagga ctgtaaagga catattcaag ttcatggtcc tctttattat ggtgtttttt gcctttatga ttggcatgtt
catactttat tcttactacc ttggggctaa agttaatgct gcttttacca ctgtagaaga aagtttcaag actttatttt
ggtcaatatt tgggttgtct gaagtgactt ccgttgtgct caaatatgat cacaaattca tagaaaatat tggatacgtt
ctttatggaa tatacaatgt aactatggtg gtcgttttac tcaacatgct aattgctatg attaatagct catatcaaga
aattgaggat gacagtgatg tagaatggaa gtttgctcgt tcaaaacttt ggttatccta ttttgatgat ggaaaaacat
tacctccacc tttcagtcta gttcctagtc caaaatcatt tgtttatttc atcatgcgaa ttgttaactt tcccaaatgc
agaaggagaa ggcttcagaa ggatatagaa atgggaatgg gtaactcaaa gtccaggtta aacctcttca ctcagtctaa
ctcaagagtt tttgaatcac acagttttaa cagcattctc aatcagccaa cacgttatca gcagataatg aaaagactta
taaagcggta tgttttgaaa gcacaagtag acaaagaaaa tgatgaagtt aatgaaggtg aattaaaaga aatcaagcaa
gatatctcca gccttcgtta tgaacttttg gaagacaaga gccaagcaac tgaggaatta gccattctaa ttcataaact
tagtgagaaa ctgaatccca gcatgctgag atgtgaatga tgcagcaacc tggatttggc tttgactata gcacaaatgt
gggcaataat atttctaagt atgaaatact tgaaaaacta tgatgtaaat ttttagtatt aactaccttt atcatgtgaa
cctttaaaag ttagctctta atggttttat tgttttatca catgaaaatg cattttattt gtctgctttg acattacagt
ggcataccat tgtgttgaaa agcccaatat tactatatta ttgaaacttt tattcatttt agagtaaact ccacatcttt
gcactacctg tttgcctcca agagactatc agttccttgg ggacagggac catgtcttat tcatctttgt gtctccagca
tctagtacag tgcctggtat atagtaggtg ctcaataaat gttgaaacca actgaactgc caacaaaata aaaataaaaa
gtcttcacta tgtagcatac cttcccttgt ccaagttctg aagaggtttt tttttttttt ttttaataga aactgaagac
attttacaac cagctatgac ttggtaagac attcttagaa ttttaggtgt cactgataat cctagaacca ctgagcccca
agtgaagaat ttaacaacaa aatgggttaa tgaaaaatat aattacattg tatatttaag tttcatagaa ttatttaaaa
caacacatta aagatttttc taaaatat GenBank NM_003305.2 (TRPC3 short form; 3330 nucleotide base pairs)

(SEQ ID NO: 5)

gggccctgac atgtgaaagg aaggaatgtg ccctaatatt ctacagttgt tttatcgttg ctactgatta ggtccatgga
gggaagccca tccctgagac gcatgacagt gatgcgggag aagggccggc gccaggctgt caggggcccg gccttcatgt -continued

```
tcaatgaccg cggcaccagc ctcaccgccg aggaggagcg cttcctcgac gccgccgagt acggcaacat cccagtggtg
cgcaagatgc tggaggagtc caagacgctg aacgtcaact gcgtggacta catgggccag aacgcgctgc agctggctgt
gggcaacgag cacctggagg tgaccgagct gctgctcaag aaggagaacc tggcgcgcat tggcgacgcc ctgctgctcg
ccatcagcaa gggctacgtg cgcatcgtag aggccatcct caaccaccct ggcttcgcgg ccagcaagcg tctcactctg
agcccctgtg agcaggagct gcaggacgac gacttctacg cttacgacga ggacggcacg cgcttctcgc cggacatcac
ccccatcatc ctggcggcgc actgccagaa atacgaagtg gtgcacatgc tgctgatgaa gggtgccagg atcgagcggc
cgcacgacta tttctgcaag tgcggggact gcatggagaa gcagaggcac gactccttca gccactcacg ctcgaggatc
aatgcctaca aggggctggc cagcccggct tacctctcat tgtccagcga ggacccggtg cttacggccc tagagctcag
caacgagctg gccaagctgg ccaacataga gaaggagttc aagaatgact atcggaagct ctccatgcaa tgcaaagact
ttgtagtggg tgtgctggat ctctgccgag actcagaaga ggtagaagcc attctgaatg gagatctgga atcagcagag
cctctggagg tacacaggca caaagcttca ttaagtcgtg tcaaacttgc cattaagtat gaagtcaaaa agtttgtggc
tcatcccaac tgccagcagc agctcttgac gatctggtat gagaacctct caggcctaag ggagcagacc atagctatca
agtgtctcgt tgtgctggtc gtggccctgg gccttccatt cctggccatt ggctactgga tcgcaccttg cagcaggctg
gggaaaattc tgcgaagccc ttttatgaag tttgtagcac atgcagcttc tttcatcatc ttcctgggtc tgcttgtgtt
caatgcctca gacaggttcg aaggcatcac cacgctgccc aatatcacag ttactgacta tcccaaacag atcttcaggg
tgaaaaccac ccagtttaca tggactgaaa tgctaattat ggtctgggtt cttggaatga tgtggtctga atgtaaagag
ctctggctgg aaggacctag ggaatacatt ttgcagttgt ggaatgtgct tgactttggg atgctgtcca tcttcattgc
tgctttcaca gccagattcc tagctttcct tcaggcaacg aaggcacaac agtatgtgga cagttacgtc caagagagtg
acctcagtga agtgacactc ccaccagaga tacagtattt cacttatgct agagataaat ggctcccttc tgaccctcag
attatatctg aaggccttta tgccatagct gttgtgctca gcttctctcg gattgcgtac atcctccctg caaatgagag
ctttggcccc ctgcagatct ctcttggaag gactgtaaag gacatattca agttcatggt cctctttatt atggtgtttt
ttgcctttat gattggcatg ttcatacttt attcttacta ccttggggct aaagttaatg ctgcttttac cactgtagaa
gaaagtttca agactttatt ttggtcaata tttgggttgt ctgaagtgac ttccgttgtg ctcaaatatg atcacaaatt
catagaaaat attggatacg ttctttatgg aatatacaat gtaactatgg tggtcgtttt actcaacatg ctaattgcta
tgattaatag ctcatatcaa gaaattgagg atgacagtga tgtagaatgg aagtttgctc gttcaaaact ttggttatcc
tattttgatg atggaaaaac attacctcca cctttcagtc tagttcctag tccaaaatca tttgtttatt tcatcatgcg
aattgttaac tttcccaaat gcagaaggag aaggcttcag aaggatatag aaatgggaat gggtaactca aagtccaggt
taaacctctt cactcagtct aactcaagag tttttgaatc acacagtttt aacagcattc tcaatcagcc aacacgttat
cagcagataa tgaaaagact tataaagcgg tatgttttga aagcacaagt agacaaagaa aatgatgaag ttaatgaagg
tgaattaaaa gaaatcaagc aagatatctc cagccttcgt tatgaacttt tggaagacaa gagccaagca actgaggaat
tagccattct aattcataaa cttagtgaga aactgaatcc cagcatgctg agatgtgaat gatgcagcaa cctggatttg
gctttgacta tagcacaaat gtgggcaata atatttctaa gtatgaaata cttgaaaaac tatgatgtaa atttttagta
ttaactacct ttatcatgtg aacctttaaa agttagctct taatggtttt attgttttat cacatgaaaa tgcattttat
ttgtctgctt tgacattaca gtggcatacc attgtgttga aaagcccaat attactatat tattgaaact tttattcatt
ttagagtaaa ctccacatct ttgcactacc tgtttgcctc caagagacta tcagttcctt ggggacaggg accatgtctt
attcatcttt gtgtctccag catctagtac agtgcctggt atatagtagg tgctcaataa atgttgaaac caactgaact
gccaacaaaa taaaaataaa aagtcttcac tatgtagcat accttccctt gtccaagttc tgaagaggtt ttttttttt
```

-continued tttttaata gaaactgaag acattttaca accagctatg acttggtaag acattcttag aattttaggt gtcactgata
atcctagaac cactgagccc caagtgaaga atttaacaac aaaatgggtt aatgaaaaat ataattacat tgtatattta
agtttcatag aattatttaa aacaacacat taaagatttt tctaaaatat GenBank NM_001366479.1 (TRPC3 C-terminal split; 4708 nucleotide base pairs)
(SEQ ID NO: 6)

gagtaacgat gctgtcctag caagtgatgc tgtcggagac aggagacggg cgccgaggag gcatcgccgc cgccgcgggg
ctggagagcc tctcccagca ccagagcccc gctcggcccc gggcttcctc gtcgcagcca cggccgcggc agctgctccc
acggtttgat ggtgggcggc ggcagctcgg cttcggcgct agcctctaac tgctggatcg cgggccgcga cgctctccgc
tcctgccttc ccgccctggg ccgcccgggg ccccggaagc cgcgggaggt ggtgaagggg cgccgcggga agactgcact
gccgcgaagg cggaggaggc cggcagccgg caccccccaca ctcggaccgc agccggcgcg atgtccacca aggtcaggaa
gtgcaaagaa caagcaaggg tgaccttccc ggcgccggag gaggaggaag acgagggcga ggacgagggc gcggagccgc
agcgccgccg ccggggctgg aggggcgtca acgggggggct ggagccgcgc tcggcgccct cgcagcggga gccgcacggc
tactgcccgc cgcccttctc ccacgggccg gacctgtcca tggagggaag cccatccctg agacgcatga cagtgatgcg
ggagaagggc cggcgccagg ctgtcagggg cccggccttc atgttcaatg accgcggcac cagcctcacc gccgaggagg
agcgcttcct cgacgccgcc gagtacggca acatcccagt ggtgcgcaag atgctggagg agtccaagac gctgaacgtc
aactgcgtgg actacatggg ccagaacgcg ctgcagctgg ctgtgggcaa cgagcacctg gaggtgaccg agctgctgct
caagaaggag aacctggcgc gcattggcga cgccctgctg ctcgccatca gcaagggcta cgtgcgcatc gtagaggcca
tcctcaacca ccctggcttc gcggccagca agcgtctcac tctgagcccc tgtgagcagg agctgcagga cgacgacttc
tacgcttacg acgaggacgg cacgcgcttc tcgccggaca tcacccccat catcctggcg gcgcactgcc agaaatacga
agtggtgcac atgctgctga tgaagggtgc caggatcgag cggccgcacg actatttctg caagtgcggg gactgcatgg
agaagcagag gcacgactcc ttcagccact cacgctcgag gatcaatgcc tacaaggggc tggccagccc ggcttacctc
tcattgtcca gcgaggaccc ggtgcttacg gccctagagc tcagcaacga gctggccaag ctggccaaca tagagaagga
gttcaagaat gactatcgga agctctccat gcaatgcaaa gactttgtag tgggtgtgct ggatctctgc cgagactcag
aagaggtaga agccattctg aatggagatc tggaatcagc agagcctctg gaggtacaca ggcacaaagc ttcattaagt
cgtgtcaaac ttgccattaa gtatgaagtc aaaaagtttg tggctcatcc caactgccag cagcagctct tgacgatctg
gtatgagaac ctctcaggcc taagggagca gaccatagct atcaagtgtc tcgttgtgct ggtcgtggcc ctgggccttc
cattcctggc cattggctac tggatcgcac cttgcagcag gctggggaaa attctgcgaa gcccttttat gaagtttgta
gcacatgcag cttctttcat catcttcctg ggtctgcttg tgttcaatgc ctcagacagg ttcgaaggca tcaccacgct
gcccaatatc acagttactg actatcccaa acagatcttc agggtgaaaa ccacccagtt tacatggact gaaatgctaa
ttatggtctg ggttcttgga atgatgtggt ctgaatgtaa agagctctgg ctggaaggac ctagggaata cattttgcag
ttgtggaatg tgcttgactt tgggatgctg tccatcttca ttgctgcttt cacagccaga ttcctagctt tccttcaggc
aacgaaggca caacagtatg tggacagtta cgtccaagag agtgacctca gtgaagtgac actcccacca gagatacagt
atttcactta tgctagagat aaatggctcc cttctgaccc tcagattata tctgaaggcc tttatgccat agctgttgtg
ctcagcttct ctcggattgc gtacatcctc cctgcaaatg agagctttgg ccccctgcag atctctcttg gaaggactgt
aaaggacata ttcaagttca tggtcctctt tattatggtg ttttttgcct ttatgattgg catgttcata ctttattctt
actaccttgg ggctaaagtt aatgctgctt ttaccactgt agaagaaagt ttcaagactt tattttggtc aatatttggg
ttgtctgaag tgacttccgt tgtgctcaaa tatgatcaca aattcataga aaatattgga tacgttcttt atggaatata
caatgtaact atggtggtcg ttttactcaa catgctaatt gctatgatta atagctcata tcaagaaatt gaggatgaca
gtgatgtaga atggaagttt gctcgttcaa aactttggtt atcctatttt gatgatggaa aaacattacc tccacctttc
agtctagttc ctagtccaaa atcatttgtt tatttcatca tgcgaattgt taactttccc aaatgcagaa ggagaaggct
tcagaaggat atagaaatgg gaatgggtaa ctcaaagtcc aggcagataa tgaaaagact tataaagcgg tatgttttga -continued

```
aagcacaagt agacaaagaa aatgatgaag ttaatgaagg tgaattaaaa gaaatcaagc aagatatctc cagccttcgt

tatgaacttt tggaagacaa gagccaagca actgaggaat tagccattct aattcataaa cttagtgaga aactgaatcc

cagcatgctg agatgtgaat gatgcagcaa cctggatttg gctttgacta tagcacaaat gtgggcaata atatttctaa

gtatgaaata cttgaaaaac tatgatgtaa atttttagta ttaactacct ttatcatgtg aacctttaaa agttagctct

taatggtttt attgttttat cacatgaaaa tgcattttat ttgtctgctt tgacattaca gtggcatacc attgtgttga

aaagcccaat attactatat tattgaaact tttattcatt ttagagtaaa ctccacatct ttgcactacc tgtttgcctc

caagagacta tcagttcctt ggggacaggg accatgtctt attcatcttt gtgtctccag catctagtac agtgcctggt

atatagtagg tgctcaataa atgttgaaac caactgaact gccaacaaaa taaaaataaa aagtcttcac tatgtagcat

accttccctt gtccaagttc tgaagaggtt tttttttttt tttttaata gaaactgaag acattttaca accagctatg

acttggtaag acattcttag aattttaggt gtcactgata atcctagaac cactgagccc caagtgaaga atttaacaac

aaaatgggtt aatgaaaaat ataattacat tgtatattta agtttcatag aattatttaa aacaacacat taaagatttt

tctaaaatat agactgcttg ctttctgtct tagacttacg tttgttgttt ttcagtaatg tgattttctt ttaagttggg

ggttatgcag ggttgtcatt ttgttataac catctaattt ctgcctctgc tgctttaatg ctaaatgaga tatcaacagc

tgacttcata tctcacctgt gagctccctg ctgagttttg gagggtctgc tcatgggaag aaataggaaa gagcagtgac

tatgggcgta cttggaaaga catggccaag catccccagg tgtgtttcag ttcctttttgg ggcatttatt gccatcgttg

cttacaatga ttgacatctt tgtttcttat caaaggattc cagttccact ttctatataa aatatattgt gatatatcta

catatgcctt attacataat tgtgctgaat gctggtaata tccgcaatgc ctcttgactt taatgggaaa aggcatgcag

accagtaagt tccccagtca cttcagagac tataaaacac tcaaagcatt ttttaaccag ctaggtttaa atctctcata

gagttatgtt taacatcctg agtctgcagt cagttgctgt caagtcgtat aggaatacga attgtgatca tagatcaaag

attttcagag gtccttaaaa ccaactaaat acatgctact ttaaaatcat tgctatcatg cagaaaagct ctttagacat

gaagacagaa ataagtgtta aatggaacta cataaagctc tttaaagatt atttcttaat ttctactttt tgggagttaa

attaagaaag gaactttata aatgttttgc taccattgta gaacacttca ttaacttttg tgccatgcta agagtattcg

tcttaaacat ttttcaaact ttatgtactt tatgttgtgt ctcagaactg aataaaatat tgaatttt
```

Pathway Genes

In some aspects, the present disclosure provides methods comprising contacting a neuronal cell with an agent that modifies expression of or modifies activity of a product encoded by a pathway gene upstream from TRPC3.

In some aspects, the present disclosure provides methods comprising contacting a neuronal cell with an agent that modifies expression of or modifies activity of a product encoded by a pathway gene downstream from TRPC3.

A pathway gene is an upstream gene or a downstream gene of a biological pathway in which a gene of interest functions. A pathway gene is considered upstream from a gene of interest when the pathway gene has an effect (direct or indirect) on the gene of interest (e.g., TRPC3). A pathway gene is considered downstream from a gene of interest when the gene of interest has an effect (direct or indirect) on the pathway gene (e.g., TRPC3).

TRPC3 protein is involved of a number of different pathways, including neuronal excitability, cholesterol metabolism, and amyloid production and/or clearance. In some embodiments, the gene encodes a protein in a neuronal excitability pathway. In some examples, the gene encodes a protein in a cholesterol metabolism pathway. In some embodiments, the gene encodes a protein in an amyloid production and/or clearance pathway. Non-limiting examples of genes encoding proteins in these pathways include NAPA, SPTBN5, SPTBN2, VAMP2, SPTBN1, ACTN1, ACTN2, ACTN4, TRPC1, TRPC4, TRPC5, TRPC6, TRPC7, BMPR1B, BMPR2, MX1, FKBP1A, GNA11, PLCG1, PRKCA, PRKG1, ITPR1, ITPR3, CALM1, and SLC8A1. Thus, in some embodiments, an agent of the present disclosure modifies (e.g., increases or decreases) expression of or modifies (e.g., increases or decreases) activity of a product encoded by one or more genes selected from NAPA, SPTBN5, SPTBN2, VAMP2, SPTBN1, ACTN1, ACTN2, ACTN4, TRPC1, TRPC4, TRPC5, TRPC6, TRPC7, BMPR1B, BMPR2, MX1, FKBP1A, GNA11, PLCG1, PRKCA, PRKG1, ITPR1, ITPR3, CALM1, and SLC8A1.

EXAMPLES

The present disclosure is further illustrated by the following Examples. These Examples are provided to aid in the understanding of the disclosure, and should not be construed as a limitation thereof.

Genetic Background Modifies Expressivity of FAD Mutations

Figure 1A:
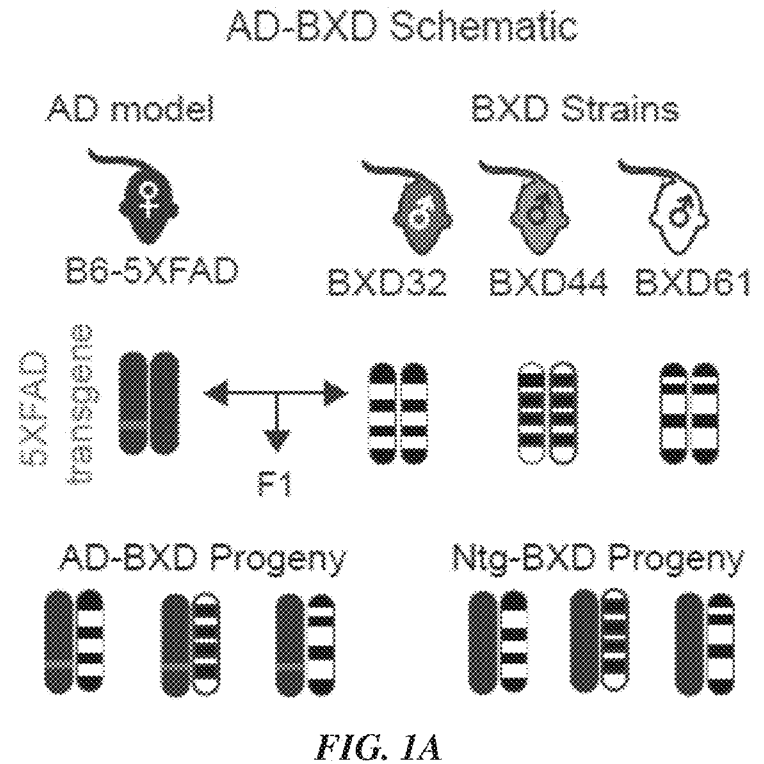
FIGS. 1A-1I: Genetic background modifies AD symptoms in a novel transgenic reference panel. (A) Female B6 mice heterozygous for the dominant 5XFAD transgene were bred to males from 27 BXD strains to generate genetically diverse but isogenic F1 offspring. (B) Body weight and working memory on the y-maze were measured bi-monthly, and at 6 and 14 months more detailed phenotyping was performed. (C) As expected, onset of working memory deficits was significantly earlier in ADBXDs compared to Ntg-BXDs [AD-BXDs: n=223 (123 females/100 males) across 28 strains vs Ntg-BXDs, n=168 mice (107 female/61 male) across 25 strains, one-tailed $t(1,51)=2.1$, $p=0.02$]. (D) AD-BXD mice exhibited contextual fear acquisition (CFA) comparable to Ntg-BXD mice at 6 m [left, one-tailed $t(1, 48)=1.4$, $p=0.08$] but are impaired by 14 m [right, one-tailed $t(1, 49)=2.0$, $p=0.03$] months. Within AD-BXD mice, background strain significantly modified the impact of the transgene on CFA [effect of strain $F(26, 354)=3.3$, $p<0.001$]. (E) AD-BXD mice exhibit recall comparable to Ntg-BXDs during the contextual fear memory (CFM) task at 6 months [left, one-tailed $t(1,48)=1.4$, $p=0.08$] but are impaired by 14 months [right, one-tailed $t(1, 49)=1.9$, $p=0.03$]. Within AD-BXD mice, background strain significantly modified the impact of the transgene on CFM [effect of strain $F(26, 354)=3.5$, $p<0.001$]. For D and E, 146 6 m AD-BXD (102 females/44 males) and 209 14 m AD-BXD (111 females/98 males) across 26 strains were used, along with 114 6 m Ntg-BXD (83 females/31 males) across 24 strains and 167 14 m Ntg-BXD mice (106 females/61 males) across 27 strains. (F) and (G) Aβ42, as measured by ELISA, increased drastically from 6 to 14 m [effect of age F(1,153)=128.0, p<0.001] but varied significantly across genetic backgrounds [effect of strain F(22,153)=2.0, p=0.01]. n=154 mice (89 female/65 male) across 23 strains. ND=no data. Strain B6SJL represents the original background strain described in Oakley et al. 2006 for comparison. (H, left) Transgene expression was assessed in subset of AD and Ntg-BXD lines [n=293 (177 females/116 males across 28 strains)]. RNA sequencing reads from the hippocampus were aligned to the human mutant sequence of APP, quantified by number of transcripts per million reads (TPM), and log transformed. AD-BXD mice exhibited significantly greater hAPP expression [t(1, 291)=92.3, p<0.001]. Across the AD-BXDs, there was no significant effects of age, sex, or (H, right) background strain. Only strains with Aβ42 data are shown here for comparison to F and G. (I, left) Same analysis was done for reads aligned to the mouse endogenous App. Across the panel, 5XFAD mice exhibited slight but significant reduction in App [t(1,291)=2.6, p=0.01]. However, within AD-BXD mice there was no effect of age, sex, or (I, right) background strain. For plots C-E, each point represents a strain average. All t-tests in C-E were one-tailed tests based on prior data assessing effects of the 5XFAD transgene on cognitive function (Kaczorowski et al., 2011; Oakley et al., 2006; Ohno, 2009); *p<0.05.
Figure 1B:
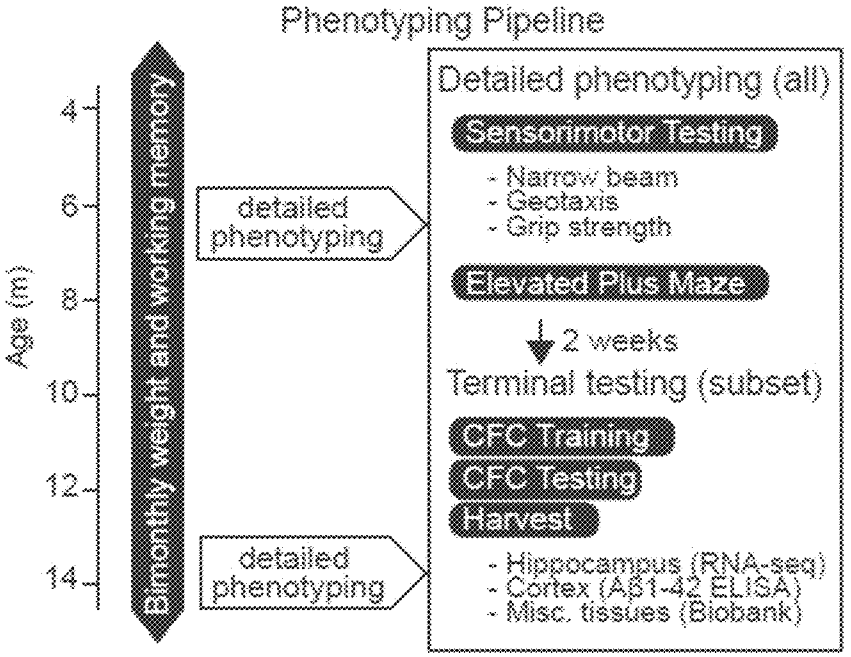

In order to evaluate the influence of genetic background on the impact of causal FAD mutations on behavioral and molecular phenotypes, we generated a panel of 28 genetically diverse F1 mouse strains with and without FAD mutations. Female B6 mice heterozygous for the autosomal dominant 5XFAD transgene (Oakley et al., 2006) were crossed to males from the BXD genetic reference panel (Peirce et al., 2004) to generate F1 progeny carrying the 5XFAD transgene (AD-BXDs) or non-transgenic littermates (Ntg-BXDs; FIG. 1A). Working memory and body weight were monitored bi-monthly and more in-depth phenotyping that included tests of motor function and anxiety was performed at both 6 and 14 months of age (FIG. 1B). A subset of mice was subsequently tested for long-term spatial learning and memory function using a contextual fear conditioning (CFC) paradigm (Fanselow, 2000; Neuner et al., 2016). This subset was immediately harvested following CFC testing and tissue was collected for biobanking and later use, including RNA-sequencing and enzyme-linked immunosorbent assays (ELISAs) as described below. This time point (immediately following testing) was chosen in order to capture molecular changes corresponding to differences in learning-related intrinsic neuronal excitability reported previously (Kaczorowski and Disterhoft, 2009; Kaczorowski et al., 2011).

Figure 1C:
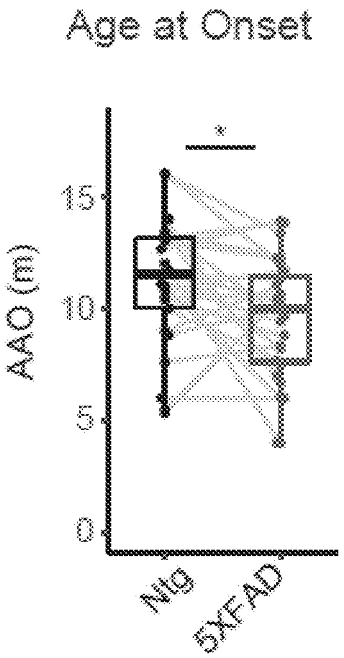
Figure 1D:
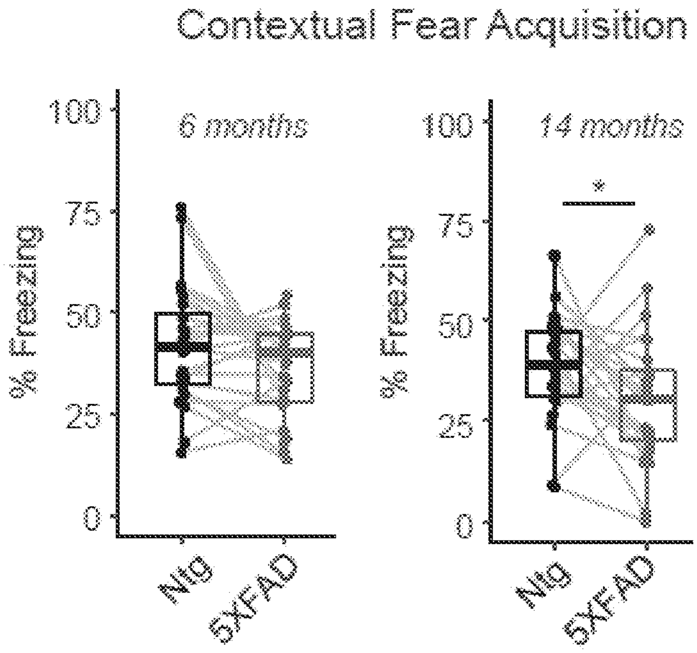
Figure 1E:
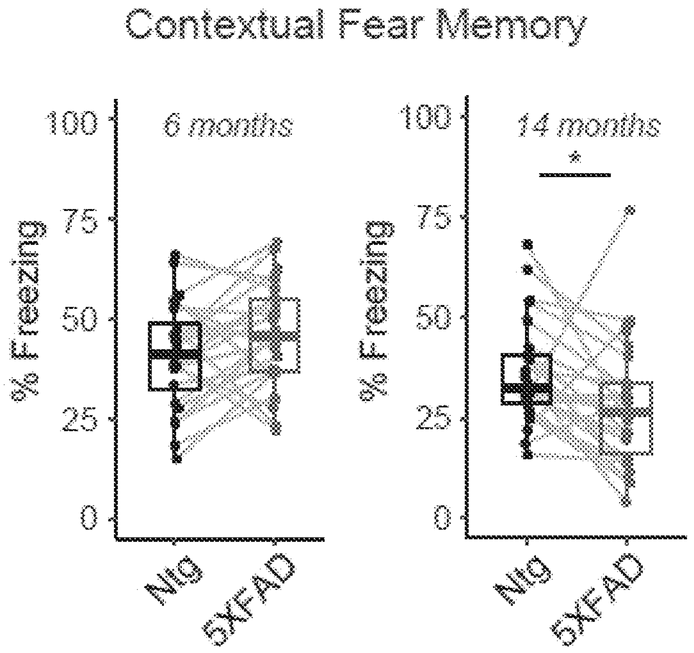

As expected (Kaczorowski et al., 2011; Oakley et al., 2006; Ohno, 2009), the 5XFAD transgene accelerated the age at onset (AAO) of working memory deficits in AD-BXD mice relative to Ntg-BXD mice (FIG. 1C) and exacerbated contextual fear acquisition (CFA) and contextual fear memory (CFM) deficits, particularly by 14 months of age (FIG. 1D-E). However, the impact of causal FAD mutations on cognitive performance varied widely depending on the specific background strain evaluated. Notably, this variation in cognitive function parallels the variation observed in human patients harboring FAD mutations (Ryman et al., 2014) and was not correlated with strain-specific variation in activity, pain sensitivity, sensorimotor abilities, or anxiety (data not shown). These results suggest the observed variation in cognitive function is regulated, in part, by genetic variants that segregate across the AD-BXD panel. In support, heritability ($h^2_{RI\bar{x}}$) estimates comparing between-strain variance (due to genetic diversity) to total sample variance (due to both genetic and environmental factors), given the average number of biological replicates per strain (Belknap, 1998), demonstrate there is a significant genetic component underlying observed variation (Table 1).

TABLE 1

Heritability estimates for phenotypic traits in AD- and Ntg-BXDs. Heritability ($h^2_{RI\bar{x}}$) was determined by calculating the ratio of between-strain variance (i.e. genetic variance) to total sample variance (within-strain variance due to technical/environmental factors plus between-strain variance), given the average number of biological replicates per strain according to established methods (Belknap, 1998).

| Trait | Between strain variance | Av. within strain variance | Av. n/strain | Heritability ($h^2_{RI\bar{x}}$) |
|---|---|---|---|---|
| Non-transgenic (Ntg)-BXDs | | | | |
| Age at onset | 7.7 | 15.7 | 7.5 | 0.8 |
| 6 m CFA | 181.2 | 433.1 | 5.1 | 0.7 |
| 6 m CFM | 196.6 | 340.5 | 5.1 | 0.7 |
| 14 m CFA | 146.6 | 520.7 | 7.2 | 0.7 |
| 14 m CFM | 168.0 | 321.9 | 7.2 | 0.8 |
| 6 m Sensorimotor composite | 0.3 | 2.1 | 8.7 | 0.6 |
| 14 m Sensorimotor composite | 1.7 | 6.8 | 7.4 | 0.6 |
| 6 m EPM % Time in Open Arms | 7.2 | 62.7 | 8.7 | 0.5 |
| 14 m EPM % Time in Open Arms | 29.2 | 149.6 | 7.4 | 0.6 |
| AD-BXDs | | | | |
| Age at onset | 5.7 | 15.7 | 8.8 | 0.8 |
| 6 m CFA | 142.9 | 293.7 | 5.6 | 0.7 |
| 6 m CFM | 163.3 | 376.8 | 5.6 | 0.7 |
| 14 m CFA | 172.0 | 360.4 | 9.0 | 0.8 |
| 14 m CFM | 141.5 | 299.8 | 9.0 | 0.8 |
| 6 m Sensorimotor composite | 1.2 | 3.8 | 10.8 | 0.7 |
| 14 m Sensorimotor composite | 2.4 | 9.3 | 9.2 | 0.7 |
| 6 m EPM % Time in Open Arms | 38.8 | 322.7 | 10.7 | 0.6 |
| 14 m EPM % Time in Open Arms | 266.6 | 625.6 | 8.8 | 0.8 |
| 6 m Amyloid (ELISA) | 2570.6 | 2050.5 | 3.3 | 0.8 |
| 14 m Amyloid (ELISA) | 36141.9 | 64897.9 | 3.9 | 0.7 |

Figure 1F:
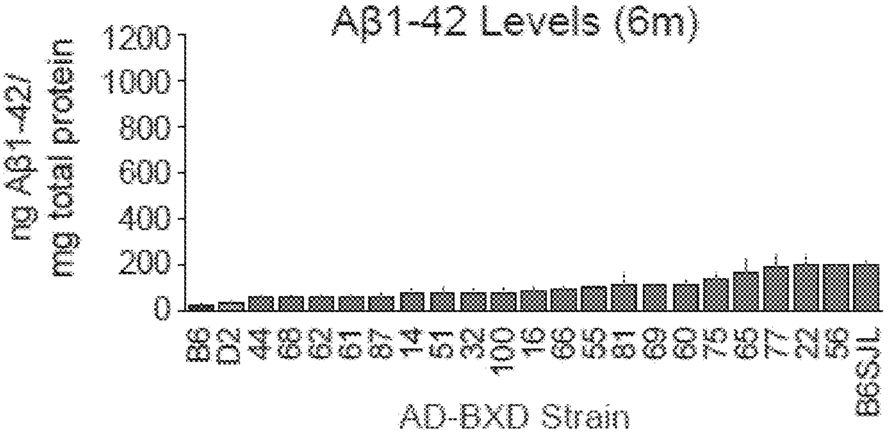
Figure 1G:
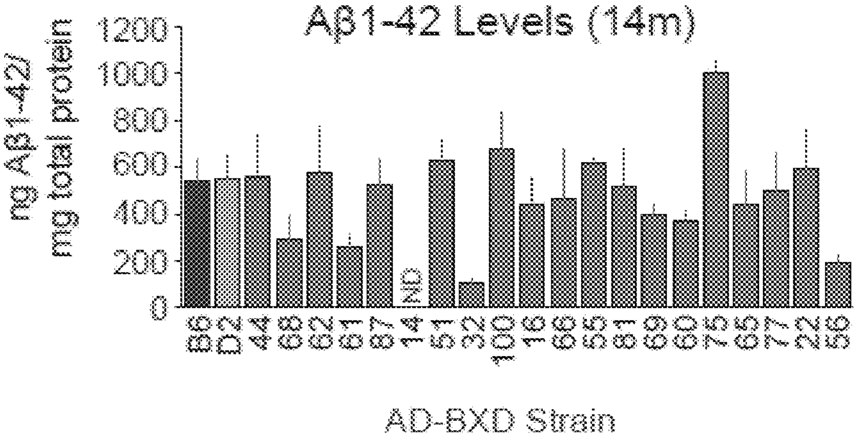

Human FAD mutations in APP and PSEN1 included in the 5XFAD transgene increase production of the toxic 42 amino-acid length amyloid beta species (Aβ1-42), thought to be an initiating factor in a cascade of symptoms eventually leading to neuron loss and dementia (Hardy and Higgins, 1992). To assess the impact of genetic background on the levels of Aβ1-42 across the panel, brain extracts from 23 AD-BXD strains were assayed in duplicate on human Aβ1-42-specific sandwich ELISAs (Oakley et al., 2006). Variation in human Aβ1-42 levels was heritable (Table 1), and overall levels increased with age [effect of age $F(1,153)=128.0$, $p<0.001$] (FIG. 1F-G). A significant main effect of strain was observed [$F(22,153)=2.0$, $p=0.01$], indicating that genetic background significantly modified human Aβ1-42 levels across the panel. In order to test whether elevated amyloid levels corresponded to an increase in plaque density, we performed immunohistochemistry (IHC) analysis on a subset of fixed hemibrains and observed robust plaque deposition in both the hippocampus and cortex of AD-BXD strains, each of which significantly correlated with amyloid levels as measured by ELISA (data not shown). As expected, human Aβ1-42 was not reliably detected in 8 Ntg-BXD brains by ELISA, or in 3 Ntg-BXD brains by IHC (data not shown), suggesting that at least by 6 months of age, Ntg-BXDs do not develop deposition of human Aβ42 compared to their 5XFAD isogenic counterparts. Similar to what is observed in human populations, no significant correlation was observed between amyloid levels and cognitive function (data not shown), suggesting partially independent mechanisms work to regulate the extent of cognitive decline and amyloid accumulation.

Figure 1H:
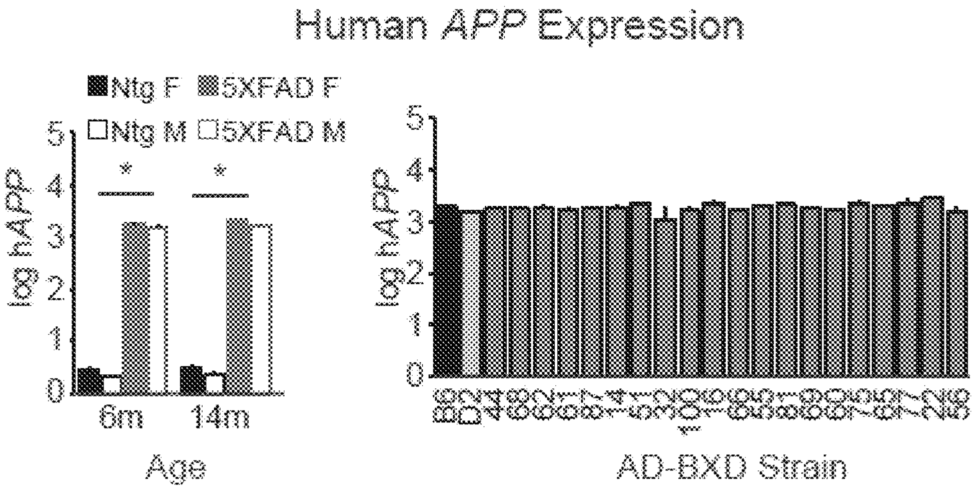
Figure 1I:
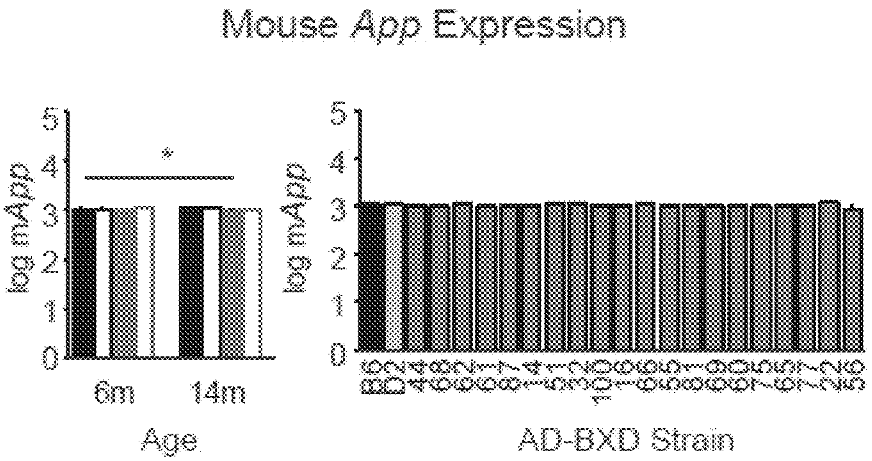

Differences in cognitive function and Aβ1-42 pathology were not explained by an effect of age, sex, or background strain on the transcription of the 5XFAD transgene itself, as measured by alignment of RNA-sequencing reads from the hippocampus to the mutated human APP (FIG. 1H) or PSEN1 (data not shown) sequences that make up the 5XFAD transgene (Oakley et al., 2006). The lack of a sex difference on either transgene expression or amyloid levels is in contrast to a previous report using a single genetic background demonstrating the 5XFAD transgene is differentially expressed based on sex (Sadleir et al., 2015), suggesting that sex-specific effects may vary across genetic backgrounds. In addition, across the AD-BXD panel, there was no effect of genetic background, age, or sex on expression of endogenous App (FIG. 1I) or Psen1 (data not shown). Overall, these results suggest that naturally occurring variants segregating across the AD-BXD panel, rather than artificial differences due to transgene expression, play a significant role in determining susceptibility and/or resilience to changes in cognitive function and amyloid deposition caused by high-risk FAD mutations.

Cognitive Function in the AD-BXDs is Sensitive to Known AD Risk Variants

To test the hypothesis that the inclusion of genetic diversity would better model human AD, we first evaluated whether the AD-BXD panel is sensitive to variation in genes known to confer risk for LOAD. Because the apolipoprotein E gene (APOE) is the best characterized risk gene for LOAD in human patients and is relatively well conserved in the mouse (Liao et al., 2015), we queried variants in mouse Apoe. One single nucleotide polymorphism (SNP) in Apoe segregates across the BXD panel (FIG. 2A), occurring near the receptor-binding region (Mahley et al., 2009). Based on sequence alignment, this SNP causes a switch from glutamate to aspartate at mouse position 163 that renders the D allele of Apoe to more closely match the sequence of ε4 human risk allele than the B allele (Zerbino et al., 2018). While the exact functional consequences of this SNP are unknown, and likely depend on the context of surrounding amino acids, we predicted the D allele of Apoe would represent a susceptibility allele across the AD-BXDs based on sequence homology.

To test this hypothesis, we first identified genotyping markers flanking Apoe across the AD-BXDs and then determined the allelic composition of Apoe in each strain. A significant effect of Apoe allele was observed on CFA [F(1,354)=4.7, p=0.03], indicating that strains carrying one copy of the D allele of Apoe performed worse on this task (FIG. 2B). We also observed a significant effect of age [F(1,354)=12.3, p=0.001] and sex [F(1, 354)=17.9, p<0.001] on CFA, as well as a trend toward an interaction between sex and Apoe genotype [F(1, 354)=3.2, p=0.08]. Together, these results indicate that while most mice exhibited age-related decline in acquisition, female mice generally performed worse on the task and were also particularly susceptible to the effects of the D allele of Apoe. The Apoe effect was even more pronounced when we considered CFM; a significant main effect of Apoe allele was again detected [F(1,355)=20.9, p<0.001], along with significant effects of sex [F(1,355)=4.9, p=0.03], age [F(1,355)=86.2, p<0.001], and a sex by age interaction [F(1,355)=7.6, p=0.006] (FIG. 2C). These results indicate first that mice harboring a single copy of the D allele of Apoe exhibited poorer CFM, and second that female mice are more susceptible to AD-related cognitive decline with age. No effect of Apoe genotype was observed on working memory traits. Across Ntg-BXDs, Apoe genotype exhibited either a less robust effect, or no effect, on cognitive performance on CFA and CFM tasks, respectively (data not shown).

Figure 3A:
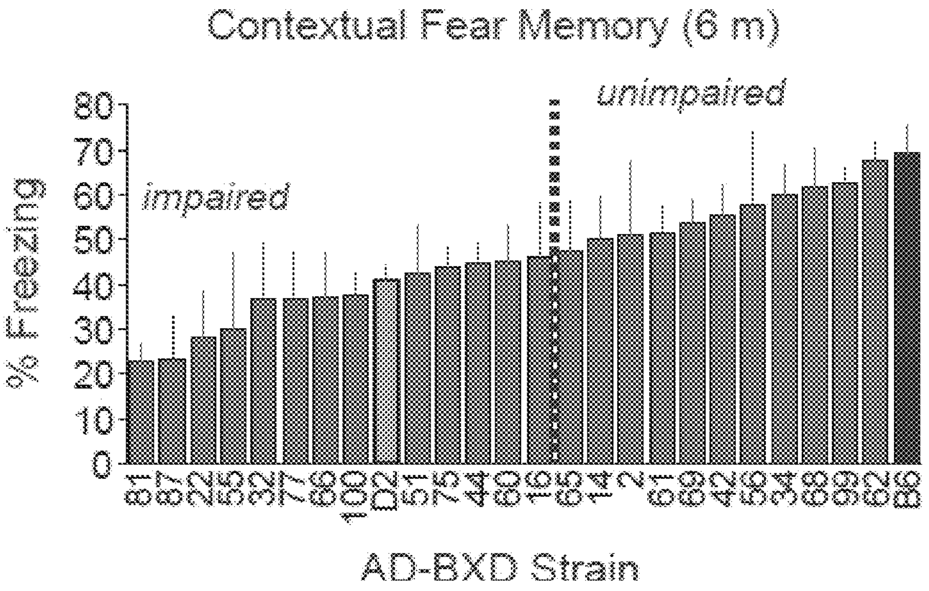
Figure 3B:
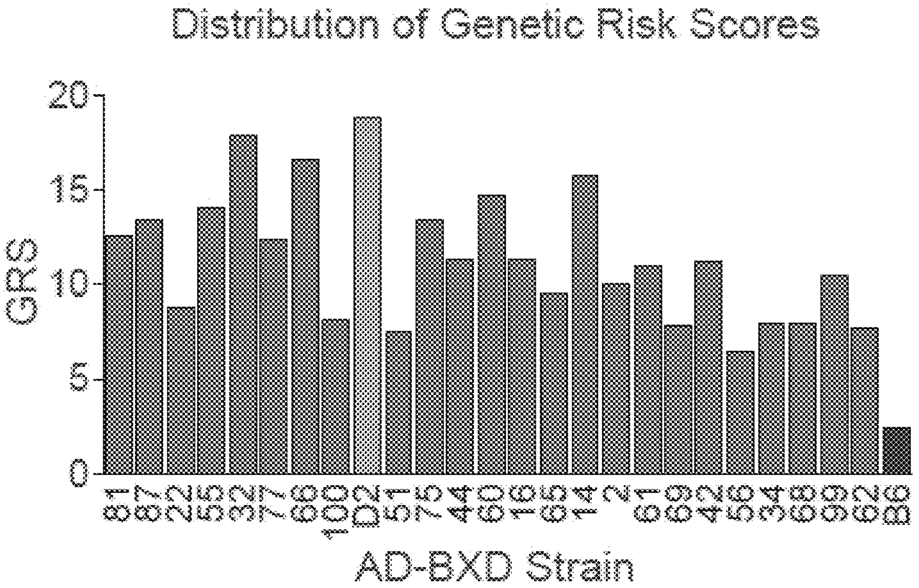

Overall, the above data demonstrates that variation at the Apoe locus in mice, particularly those harboring the 5XFAD transgene, is associated with cognitive outcomes. In humans, additional genes have been identified that play small, although significant, roles in regulating susceptibility to AD (Lambert et al., 2013). Recent studies suggest that information about genetic variation at these additional loci, in the form of a genetic risk score (GRS), can better predict an individual's risk of developing AD (Chouraki et al., 2016). In order to evaluate whether naturally occurring variants in genes associated with LOAD risk in humans are associated with cognitive outcomes in the AD-BXD panel, we computed a GRS for each of our strains similar to the method described by Chouraki and colleagues in 2016 (Chouraki et al., 2016). First, we stratified strains into impaired and unimpaired groups based on 6 month-old CFM (FIG. 3A). We then identified the genotype of each strain at 21 LOAD risk genes (across 19 genetic markers, Table 2) and classified the risk allele of each gene as that allele which appeared more frequently in the impaired group. Odds ratios were calculated and transformed based on risk allele dosage to obtain a final GRS for each strain, which was normally distributed across the panel (Shapiro-Wilk test for normality p=0.7, FIG. 3B).

TABLE 2

Genes known to confer risk of Alzheimer's disease in humans vary across the AD-BXD panel and confer various degrees of risk in our mouse population; this information was used to create a genetic risk score for each strain.

| Gene | Mouse Chr. | SNP Density (SNP/Kb) | High-impact changes | 6 m CFM AD Risk allele | Odds ratio | 95% CI | Z stat | Pval |
|---|---|---|---|---|---|---|---|---|
| Inpp5d | 1 | 1.24 | NMD SNP + indel | B | 1.30 | 0.28-6.3 | 0.36 | 0.72 |
| Cr1l | 1 | 0.06 | — | D | 2.00 | 0.41-9.8 | 0.85 | 0.39 |
| Celf1 | 2 | 0.70 | — | D | 1.50 | 0.30-7.4 | 0.50 | 0.62 |
| Cass4 | 2 | 0.08 | — | D | 1.50 | 0.30-7.4 | 0.50 | 0.62 |
| Zcwpw1 | 5 | 0.11 | — | D | 1.63 | 0.34-8.0 | 0.61 | 0.54 |
| Epha1 | 6 | 0.00 (indel) | — | D | 1.60 | 0.33-7.8 | 0.58 | 0.56 |
| Cd33 | 7 | 3.17 | MS, Stop gained | D | 1.67 | 0.30-9.2 | 0.59 | 0.56 |
| Picalm | 7 | 1.75 | — | D | 3.60 | 0.71-18.3 | 1.55 | 0.12 |

TABLE 2-continued

Genes known to confer risk of Alzheimer's disease in humans vary across the AD-BXD panel and confer various degrees of risk in our mouse population; this information was used to create a genetic risk score for each strain.

| Gene | Mouse Chr. | SNP Density (SNP/Kb) | High-impact changes | 6 m CFM AD Risk allele | Odds ratio | 95% CI | Z stat | Pval |
|---|---|---|---|---|---|---|---|---|
| Sorl1 | 9 | 12.49 | MS, SRV, SAV | D | 2.50 | 0.50-12.6 | 1.11 | 0.27 |
| Abca7 | 10 | 0.05 | — | D | 1.17 | 0.24-5.6 | 0.19 | 0.85 |
| Slc24a4 | 12 | 4.07 | SRV | D | 3.60 | 0.71-18.3 | 1.55 | 0.12 |
| Rin3 | 12 | 4.95 | MS | Located within same region as Slc24a4 | | | | |
| Mef2c | 13 | 0.15 | — | B | 0.86 | 0.18-4.1 | 0.19 | 0.85 |
| Nme8 | 13 | 3.68 | SRV | D | 1.40 | 0.30-6.6 | 0.42 | 0.67 |
| Clu | 14 | 0.00 (indel) | NMD | D | 5.50 | 0.84-36.2 | 1.77 | 0.08 |
| Ptk2b | 14 | 1.85 | MS, SRV | Located within same region as Clu | | | | |
| Fermt2 | 14 | 2.40 | — | D | 1.83 | 0.32-10.6 | 0.68 | 0.50 |
| Cd2ap | 17 | 4.85 | MS, SRV | — | 1.00 | 0.21-4.7 | 0.00 | 1.00 |
| H2-Eb1 | 17 | 21.41 | MS, SRV, stop gained | D | 1.05 | 0.22-5.0 | 0.06 | 0.95 |
| Trem2 | 17 | 0.13 | — | B | 1.20 | 0.25-5.8 | 0.23 | 0.82 |
| Bin1 | 18 | 0.21 | MS | D | 1.33 | 0.28-6.3 | 0.36 | 0.72 |

Figures 3C, 3D, 3E, 3F, 3G, 3H:
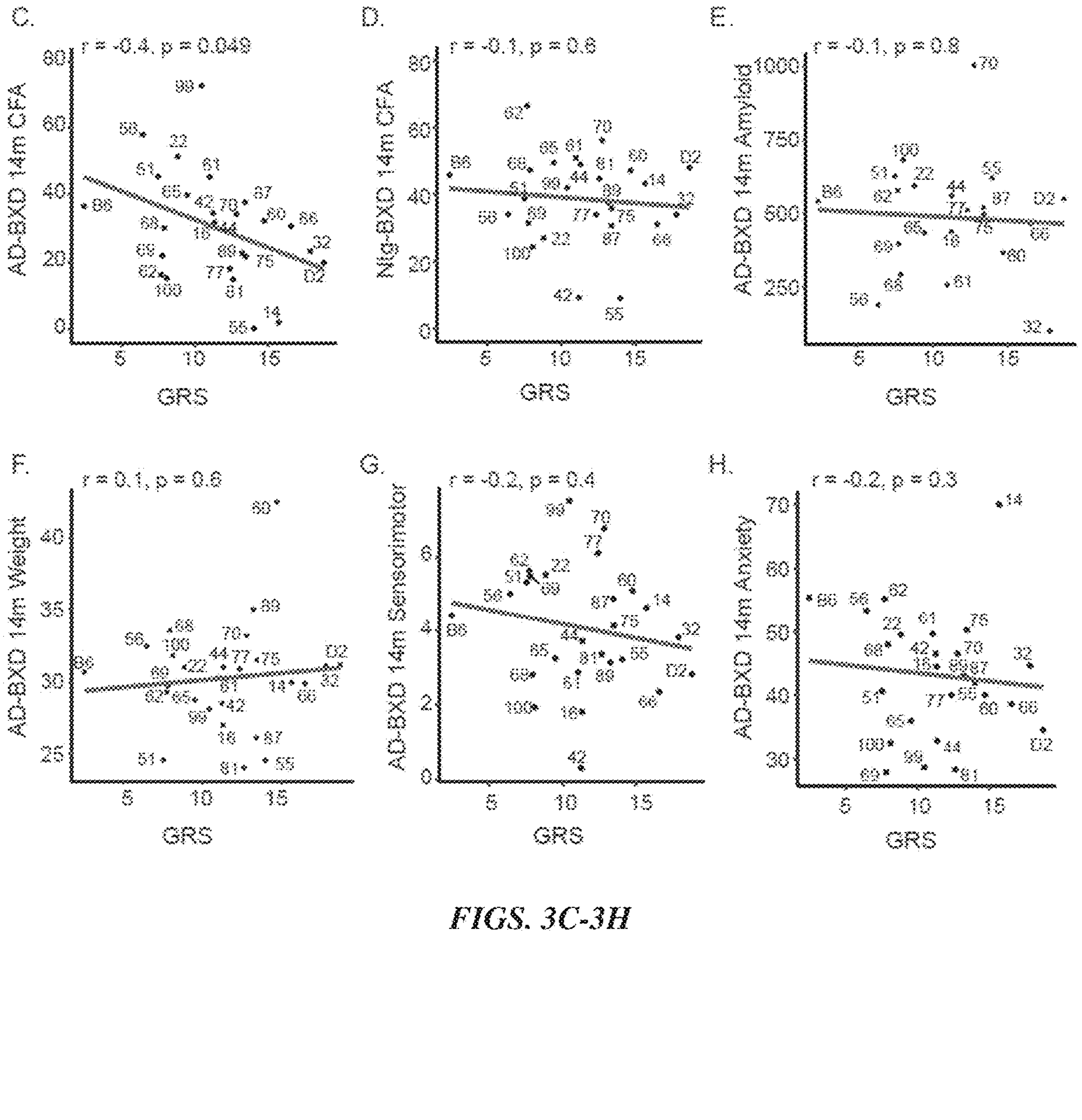

Once each GRS was calculated, we then asked how well a strain's score predicted cognitive outcomes as measured on an uncorrelated task in a separate cohort of AD-BXD mice (i.e. 14 m CFA). Although no individual risk gene significantly differentiated impaired vs unimpaired strains at 6 m, when taken together, the GRS was significantly associated with cognitive outcomes in AD-BXD mice (FIG. 3C). Notably, the GRS was not associated with cognition in Ntg-BXDs, suggesting genes used to create the GRS exhibit more specificity toward mediating AD-related decline (FIG. 3D). We repeated this entire process with 1,000 sets of 19 randomly selected genetic markers and determined the correlation of the GRS and 14 m AD-BXD CFA was among the top 5% of all observed permutations, suggesting the additive association of LOAD risk genes with 5XFAD-related cognitive decline is much greater than a set of genes randomly distributed across the genome. In addition, a GRS derived from genotypes at the same risk alleles, but using the distribution of 'impaired' and 'unimpaired' Ntg-BXD strains, rather than AD-BXD strains, to define odds ratios for each individual LOAD risk gene showed no relationship with late-disease cognitive outcomes in either 14 m Ntg-BXDs or AD-BXDs (data not shown), further demonstrating these genes uniquely interact with the 5XFAD transgene. Finally, the original GRS (FIG. 3B) showed no association to non-cognitive traits such as amyloid levels, weight, sensorimotor abilities, or anxiety (FIG. 3E-H). Overall, these results demonstrate 1) the AD-BXD panel is sensitive to variation in known LOAD risk variants, and 2) the CFA task is particularly sensitive to this variation, and has the potential to be used as a translationally relevant cognitive assay in preclinical AD studies.

AD-BXD Transcriptome Shows Concordance with Late-Onset AD Signature

We next decided to investigate whether or not the AD-BXD panel shared similarities with human AD at the transcriptional level. We first performed RNA-sequencing on hippocampal tissue from a subset of AD-BXDs and Ntg-BXDs and evaluated the expression of genes known to be misregulated in AD. As expected from studies of post-mortem human tissue, the 5XFAD transgene significantly altered the expression of a number of these genes, particularly Bin1, Clu, Cd33 (Karch et al., 2012), Trem2 (Piccio et al., 2016), and C1qa (Hong et al., 2016) (FIG. 4A). Similar to what we observed for behavioral and pathological phenotypes, risk gene expression varied across the AD-BXD panel. This suggests genetic background may influence AD susceptibility by altering underlying transcriptional networks, so to gain a mechanistic understanding of functional categories altered in AD-BXDs relative to Ntg-BXDs, we performed differential expression analysis using DESeq2 (Love et al., 2014) followed by gene set enrichment analysis (GSEA) (Subramanian et al., 2005) (data not shown). As expected, the gene ontology (GO) functional categories most significantly enriched among genes observed to be downregulated in AD largely related to neuronal activity, structure, and function (FIG. 4B, left) while the GO functional categories most significantly enriched among genes observed to be upregulated in AD related largely to immune response (FIG. 4B, right). Together, these data highlight the maintenance of neuron activity, particularly the activity of select ion channels and receptors, as pathways that may be augmented to promote resilience, while immune pathways as those that may need to be suppressed to promote resilience.

To further evaluate whether observed changes in our AD-BXD model paralleled those observed in human patients, we next performed a series of cross-species comparative analyses using aged brain tissue (14 m AD-BXD mice) to best parallel the tissue available from human patients. First, we evaluated the expression of a set of 60 core genes previously defined as a human AD consensus signature, primarily enriched for downregulated mitochondrial and neuronal genes [data not shown, (Hargis and Blalock, 2017)]. We observed higher concordance between our mouse panel and this human AD signature (FIG. 5A) than that reported for other AD models on a single genetic background (Hargis and Blalock, 2017). This effect replicated in 3 independent human datasets tested (data not shown). Second, we noted that the significant upregulation of immune-related pathways in our AD-BXD mice (FIG. 4B) paralleled the significant association of immune-related genes with human AD, both at the transcriptional and genetic level (International Genomics of Alzheimer's Disease, 2015; Zhang et al., 2013). To test whether the identity of genes driving this association were similar across mice and humans, we used GeneWeaver (Baker et al., 2016) to calculate overlap of genes upregulated in aged 14 m AD-BXD mice (data not shown) and two gene lists associated with human AD. First, we utilized a list of genes belonging to the transcriptional co-expression module most highly associated with human AD identified by Zhang and colleagues (Zhang et al., 2013), and second, a list of 151 highly connected AD-related genes identified by Jones et. al. (International Genomics of Alzheimer's Disease, 2015). Each of these lists were significantly enriched for genes with immune-related annotations. In both cases, the overlap between mouse and human signatures was significant (FIG. 5B).

Finally, we tested whether the AD-specific enrichment of immune-related pathways observed in human AD, but not normal aging (Raj et al., 2017), was preserved across our AD and Ntg-BXDs. To do this, we identified GO terms enriched among those genes significantly differentially expressed between 14 m AD and Ntg-BXDs (data not shown, 5XFAD-related genes) and those enriched among genes significantly differentially expressed between 6 m and 14 m Ntg-BXDs (data not shown, normal aging-related genes). To enable comparison across datasets, we identified those GO terms with enough genes to be identified in each set and compared enrichment strength across AD and normal aging in our mouse panel (FIG. 5C and data not shown). Enrichment of immune-related terms was exclusively observed among our list of 5XFAD-related genes, and not normal aging-related genes. A similar trend was observed in neuron and ion-channel related terms, suggesting downregulation of neuron structure, function, and/or activity to also be a unique feature of AD relative to normal aging in the mouse. Changes unique to normal aging include DNA metabolism, RNA processing, and peptidase activity (FIG. 5C, bottom right). Overall, the incorporation of genetic diversity into a mouse model of AD resulted in a transcriptomic profile that more closely matched human AD than previous AD models with limited genetic background variation (Hargis and Blalock, 2017).

Targeted Knockdown of Positional Candidate Trpc3 Reduces Aβ42 Load and AD-Related Cognitive Symptoms In order to contribute new understanding of mechanisms underlying resilience to disease, we pursued functional validation of Trpc3, an ion channel that had not previously been associated with AD, but for which we had strong biological evidence supporting a potential role in disease. It was our hypothesis that targeting a gene that is a cognitive enhancer and putative mediator of Aβ42 levels would likely provide a double benefit to AD carriers by better allowing neurons to participate in networks critical for learning.

Trpc3 is a member of the transient receptor potential channel family and is permeable to cations including calcium (Dietrich et al., 2005). Misregulation of calcium signaling has previously been implicated in the pathogenesis of AD (LaFerla, 2002), and Trpc3 itself has recently been implicated in neuronal excitability and cognitive function in adult mice (Neuner et al., 2015). In addition, Trpc3 function has been shown to be sensitive to cellular cholesterol (Graziani et al., 2006), a pathway closely linked to AD by GWAS hits such as APOE, CLU, and ABCA7 (Karch and Goate, 2015). Across the AD-BXDs, Trpc3 contains both a sequence variant and an insertion in a predicted splice region, further strengthening a possible role for Trpc3 in in cognitive deficits and amyloid processing. Notably, the insertion occurs in exon 10 of Trpc3 (NM_019510), and a calmodulin/IP3R binding site within exons 9 and 10 has previously been shown to modulate TRPC3 activation (Zhang et al., 2001). Given that antibodies directed against beta-amyloid have not resulted in disease-modifying treatments, and beta-amyloid does not correlate strongly with cognition in either humans or our ADBXD panel (data not shown), we hypothesized that targeting a putative modulator of amyloid pathology that also has cognitive function-enhancing capabilities (i.e. Trpc3) may provide an added benefit to susceptible strains by reducing pathology and increasing neuronal excitability.

Figure 6A:
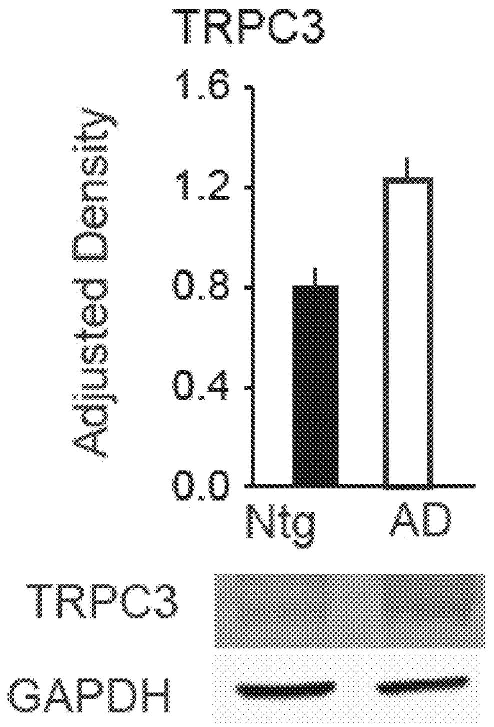
Figure 6B:
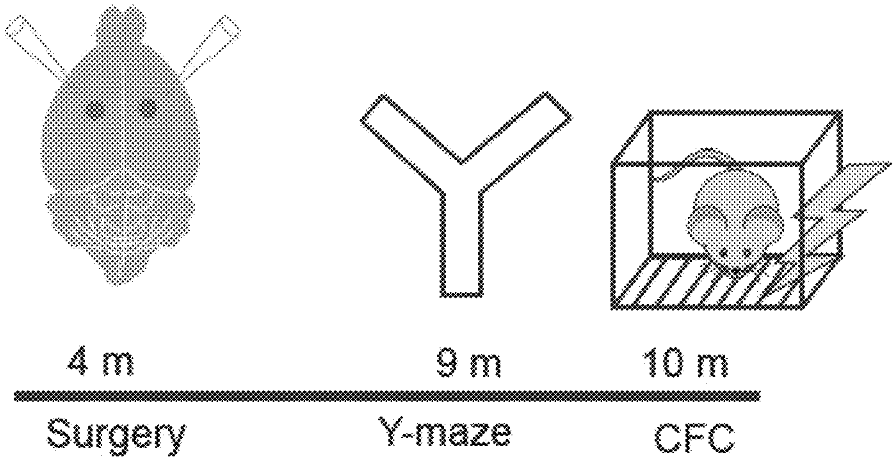

Since TRPC3 protein is increased in hippocampus from 5XFAD mice compared to Ntg controls [FIG. 6A, n=4/grp, $t(1,6)=3.7$, $p=0.01$], we injected our previously validated AAV9 viral vector containing either shRNA targeting Trpc3 (shRNA-Trpc3) or a scrambled shRNA control (shRNA-Ctrl) (Neuner et al., 2015) directly in the dorsal hippocampus of presymptomatic male 4 month-old 5XFAD-B6SJL mice (Oakley et al., 2006). This strain was chosen as it a susceptible strain with robust amyloid deposition when compared to mice from our AD-BXD panel (data not shown). The mice were aged to 9 months, a time point at which a majority of the population exhibits both amyloid accumulation and memory deficits (Kaczorowski et al., 2011; Oakley et al., 2006), and then working memory and CFM was assessed (FIG. 6B).

Figure 6C:
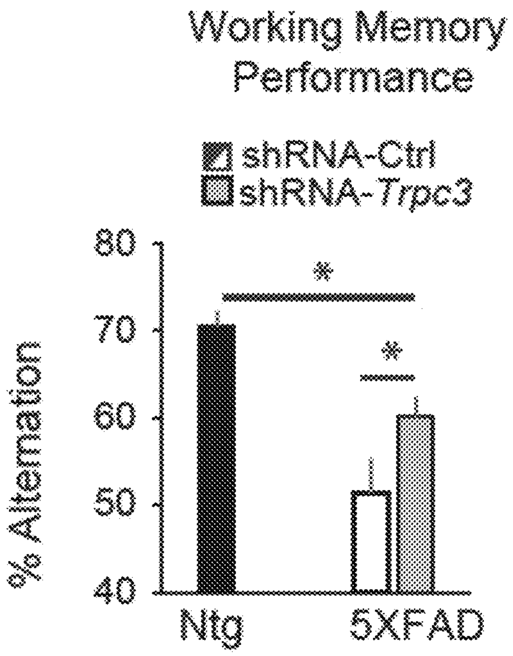
Figure 6D:
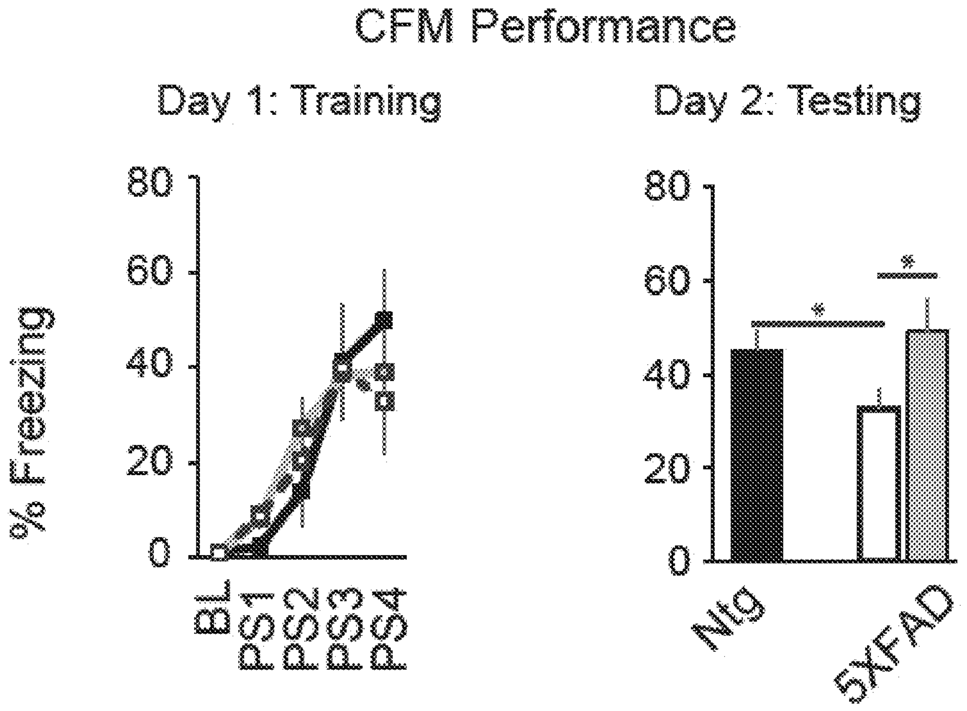

As expected, 5XFAD mice injected with shRNA-Ctrl performed significantly worse than Ntg littermates injected with shRNA-Ctrl on both working memory [FIG. 6C—effect of group, $F(2, 28)=10.6$, $p<0.001$; post-hoc 5XFAD shRNA-Ctrl vs Ntg shRNA-Ctrl: $t(1,18)=4.4$, $p<0.001$] and CFM tests [FIG. 6D—effect of group, $F(2,26)=3.4$, $p=0.05$; post-hoc 5XFAD shRNA-Ctrl vs Ntg shRNA-Ctrl: $t(1,17)=2.3$, $p=0.03$]. Consistent with our hypothesis, 5XFAD mice that had received shRNA-Trpc3 performed better than 5XFAD mice receiving control injections [post-hoc 5XFAD shRNA-Trpc3 vs 5XFAD shRNA-Ctrl, $p<0.05$ on both tasks] and were statistically indistinguishable from controls on the CFM task (post-hoc 5XFAD shRNA-Trpc3 vs Ntg shRNA-Ctrl $p>0.05$). Importantly, no significant effects of group on total distance traveled or arms entered in the y-maze, or baseline freezing during CFC training, were observed indicating no difference between groups on measures of total activity or anxiety (FIG. 7). Similar effects were observed in non-transgenic mice, demonstrating a general effect of Trpc3 knockdown on cognitive aging (FIG. 8).

Figure 6E:
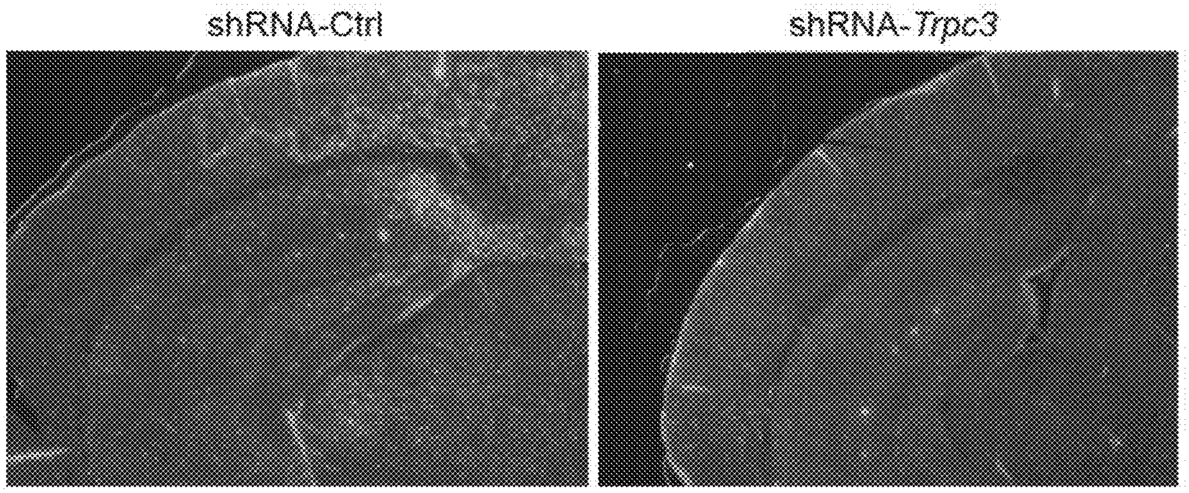
Figure 6F:
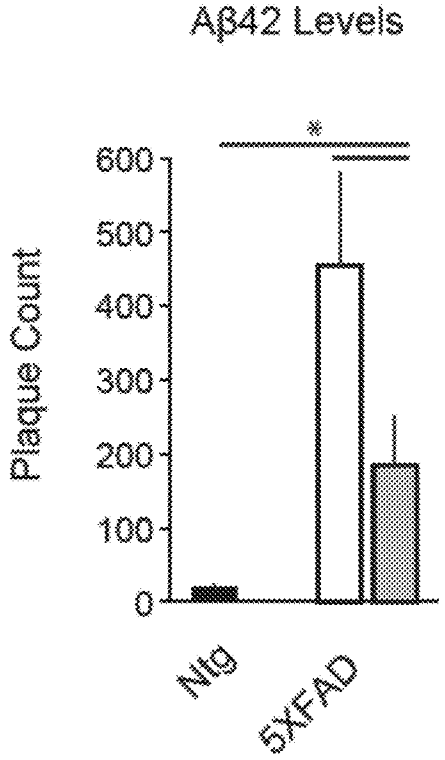
Figure 6G:
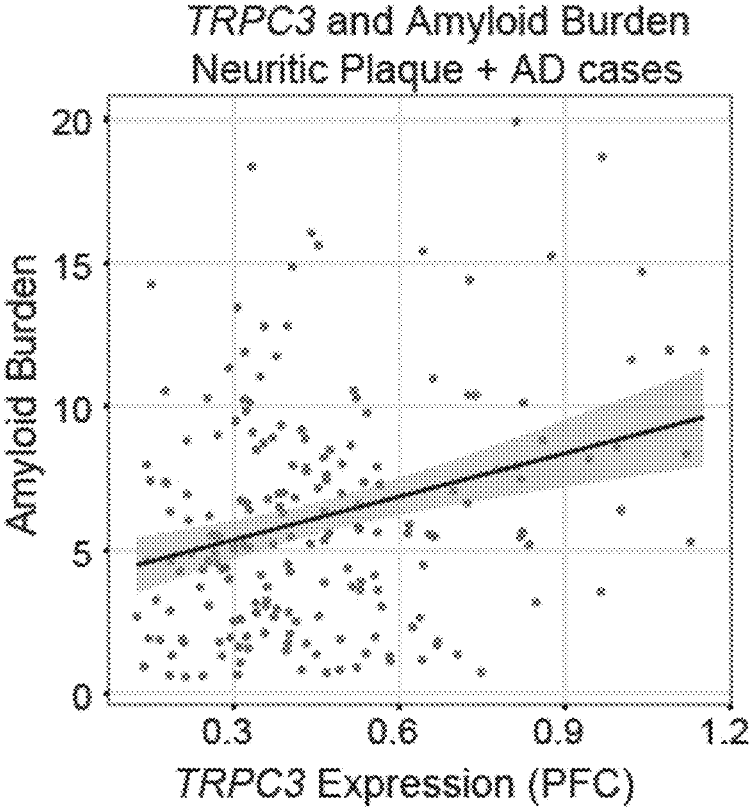

Finally, we investigated the effects of Trpc3 knockdown on accumulation of Aβ42. Mice were harvested at 10 months and one hemisphere of each brain region was fixed in 4% PFA. Immunohistochemistry for Aβ42 was performed and number of plaques counted using Image J's particle analysis software (Hurtado et al., 2010). 5XFAD shRNA-Ctrl mice exhibited a robust increase in the total number of plaques observed in the cortex and hippocampus (FIG. 6E). In contrast, 5XFAD mice treated with shRNA-Trpc3 showed a decrease in the number of plaques [effect of group: $F(2,11)=5.5$, $p=0.03$; post-hoc one-tailed t-test 5XFAD shRNA-Ctrl vs 5XFAD shRNA-Trpc3: $t(1,7)=2.0$, $p=0.04$] and were not significantly different than Ntg mice [post-hoc t-test 5XAFD shRNA-Trpc3 vs Ntg shRNA-Ctrl: $t(1,6)=1.8$, $p=0.12$]. These results demonstrate that in addition to a general role in cognitive aging, Trpc3 plays a disease-specific role in the regulation of amyloid levels in AD.

To assess the translational relevance of this finding, we next evaluated the relationship between TRPC3 and human AD. Using ROS/MAP data, a significant association was identified between TRPC3 expression in the prefrontal cortex of neuritic plaque positive AD cases and a brain-wide measure of amyloid burden (see Methods), even after adjusting for age at death and sex ($p=0.0005$, FIG. 6G). As in our mouse panel, higher levels of TRPC3 were associated with an increased amyloid burden. In contrast, no association was observed between TRPC3 expression and neurofibrillary tangles, cerebral amyloid angiopathy, or Lewy bodies ($p>0.05$). In addition, publically available data was mined for evidence of TRPC3 association with human AD. Of three SNPs annotated to TRPC3 in the International Genomics of Alzheimer's Project (IGAP) dataset (Lambert et al., 2013), one SNP displayed a nominal association with AD (rs114991240, uncorrected p=0.03). Finally, TRPC3 appears in the same module as known AD risk genes APOE, CLU, and DSG2 in a gene regulatory network constructed from post-mortem brain tissue from LOAD patients and cognitively normal controls (Zhang et al., 2013), suggesting its role in a larger regulatory network may influence risk of AD. Together, these results suggest that while variants in TRPC3 itself may not play a highly significant role in regulating risk of AD in human populations, mechanisms and pathways in which TRPC3 is involved (e.g. neuronal excitability, cholesterol metabolism, amyloid production and clearance) are important for modulating risk of AD. Overall, results here implicate Trpc3 for the first time in regulation of AD pathogenesis and demonstrate the ability to transition from candidate gene identified by QTL mapping to functional validation in an in vivo mouse model and translational evaluation using human datasets.

The discovery that decreasing expression of Trpc3 in either normal aging or an aggressive mouse model of AD is sufficient to delay the onset of both cognitive and disease-specific pathological symptoms greatly contributes to our understanding of AD genetics, how they relate to mechanisms underlying normal aging, and provides an additional target on which to focus future studies.

Experimental Model and Subject Details

Female congenic C57BL/6J mice hemizygous for the dominant 5XFAD transgene (Oakley et al., 2006), which consists of 5 human mutations known to cause familial AD [three in amyloid precursor protein (APP; Swedish: K670N, M671L, Florida: I716V, and London: V717I) and two in presenilin 1 (PSEN1; M146L and L286V)], were obtained from The Jackson Laboratory (JAX MMRRC Stock No: 34848-JAX). These mice were bred with 28 males from a set of genetically diverse recombinant inbred strains from the well-established BXD genetic reference panel (Peirce et al., 2004). By selecting the same maternal background strain (i.e. 5XFAD-057BL/6J) across the panel for cross with male BXD strains, we were able to introduce variants in the nuclear DNA, hold the mitochondrial genome constant, and control for strain-specific differences in maternal behavior on offspring behavior. The F1 progeny resulting from this B6-5XFAD by BXD cross are isogenic recombinant inbred backcross mice, each harboring one maternally derived B allele and either a B or D paternally derived allele at any given genomic locus. As expected from a Mendelian pattern of inheritance, ~50% of these F1 mice carry the 5XFAD transgene (termed AD-BXDs) and ~50% are non-transgenic (Ntg) littermate controls referred to Ntg-BXDs. Male and female offspring were group housed (2-5 per cage) and maintained on a 12 hr light/dark cycle with ad libitum access to food and water. All mice were genotyped for the 5XFAD transgene through a combination of in-house genotyping according to The Jackson Laboratory protocols for strain #34848-JAX and outside services (Transnetyx, TN, USA, and The Jackson Laboratory Transgenic Genotyping Services). Working memory and body weights were monitored longitudinally, and more detailed phenotyping occurred at 6 and 14 m. These time points were selected to obtain an adult phenotype (6 m) and a middle-aged to aged time point (14 m) that captured variation in disease symptoms before the mice exhibited severe health-related problems that confounded behavioral testing. All mouse experiments were carried out in accordance with the standards of the Association for the Assessment and Accreditation of Laboratory Animal Care (AAALAC), as well as the recommendations of the National Institutes of Health Guide for the Care and Use of Laboratory Animals.

Method Details

Y-Maze

For all behavioral testing, mice were habituated to transport and to the testing room for three days prior to testing. The y-maze test of spontaneous alternation was performed as described previously (Oakley et al., 2006). The y-maze used for testing was made of clear acrylic with arms that were 2" wide×12" long×2" high. The maze was placed on a table in a dimly lit room and spatial cues were displayed on walls around the table. Mice were placed in a randomized start arm and video tracking software was used to monitor arm entries (ANY-maze, Stoelting Co., IL, USA). An arm entry was called when the mouse's entire body, including the two back feet, entered the arm. The sequence and total number of arms entered was recorded, and the percentage of successful alternations was calculated as follows: number of alternations/maximum possible alternations (total number of arms entered−2)×100. For each animal that was measured longitudinally (i.e. not harvested at the early 6 m time point), the age at which each animal became 'impaired', or performed below chance levels (50%), was recorded and used as the animals "age at onset" [AD-BXDs: n=226 (126 females/100 males) across 28 strains vs Ntg-BXDs, n=171 mice (108 females/63 males) across 25 strains]. Strain averages for age at onset were then calculated.

Sensorimotor Battery

At 6 m [AD-BXDs n=284 (185 females/90 males) across 28 strains, Ntg-BXDs n=220 (158 females/62 males) across 27 strains] and 14 m [AD-BXDs n=222 (104 females/106 males) across 26 strains, Ntg-BXDs n=172 (109 females/63 males) across 25 strains], mice were subjected to a sensorimotor battery consisting of three tasks. First, mice were placed in the center of a 3-foot long narrow (0.5") beam elevated 20.75" off a table surface and the time taken for the mouse to cross the narrow beam onto a safe platform on either side was measured. Second, mice were placed face-down on a wire mesh grid (holes were 1 cm×1 cm) that was placed at a 45° angle. The time taken for a mouse to right itself (negative geotaxis) was recorded. A 3 minute maximum time limit was imposed for both the narrow beam and incline screen tests. If a mouse fell from the narrow beam, the maximum score of 180s was given. Third, grip strength was measured using a standard grip strength meter (Colbourn Instruments). Each of these three tasks were repeated in triplicate and the average score across three trials was used. For each mouse, a z-score based on the 6 m population average was calculated for each task and the three z-scores were summed to derive a sensorimotor composite score, which was used here to relate sensorimotor performance to cognitive abilities.

Elevated Plus Maze

At 6 m [AD-BXDs n=280 (191 females/89 males) across 28 strains, Ntg-BXDs n=220 (158 females/62 males) across 27 strains] and 14 m [AD-BXDs n=221 (116 females/105 males) across 26 strains, Ntg-BXDs n=173 (110 females/63 males) across 25 strains], anxiety was evaluated using an elevated plus maze task. Mice were placed in the center of the maze and allowed to explore for 6 minutes. Video tracking software (ANY-maze, Stoelting Co.) was used to track the mouse and calculate the time spent in open versus closed arms of the maze as well as the number of arm entries into either open or closed arms, the total number of arm entries, and the total distance travelled in the maze.

Contextual Fear Conditioning

Following 3 days of habituation to transport and to the testing room, mice were trained on a standard contextual fear conditioning (CFC) paradigm as previously described (Neuner et al., 2015). Training consisted of a 180s baseline period followed by four mild foot shocks (1s, 0.9 mA), separated by 115±20s. A 40s interval following each foot shock was defined as the post-shock interval, and the percentage of time spent freezing during each of these intervals was measured using FreezeFrame software (Coulbourn Instruments, PA, USA). The percentage of time spent freezing during the final post-shock interval (PS4) was used as an index of contextual fear acquisition (CFA). Twenty-four hours later, hippocampus-dependent contextual fear memory (CFM) was tested by returning the mouse to the testing chamber for 10 min. The percentage of time spent freezing during the testing trial was measured using FreezeFrame software and used as an index of CFM. For CFC, 146 6 m AD-BXD (102 females/44 males) and 209 14 m AD-BXD (111 females/98 males) across 26 strains were used, along with 114 6 m Ntg-BXD (83 females/31 males) across 24 strains and 167 14 m Ntg-BXD mice (106 females/61 males) across 27 strains. Pain sensitivity was evaluated in a subset of mice by recording the length of activity burst following each shock. An average post-shock reactivity score was calculated by averaging the length of each activity burst following the four training shocks.

Enzyme-Linked Immunosorbent Assay (ELISA)

Brains were removed immediately following CFC at appropriate time points (6 m or 14 m) and hemisected. One half of the brain was immediately dissected, snap frozen, and stored at −80° C. until use. Beta-amyloid 1-42 (Aβ42) levels were quantified from sections of temporal cortex [6 m n=72 mice (46 female/46 male) across 22 AD-BXD strains, 14 m n=82 mice (43 female/33 male) across 21 AD-BXD strains] as previously described (Oakley et al., 2006). Briefly, tissue was homogenized in 1×PBS+1% Triton-X 100 using the TissueLyser II system (Qiagen) and sonicated 2×10s on low power. Protein concentration was determined using a NanoDrop 2000 UV-Vis Spectrophotometer (ThermoScientific, USA). Brain homogenates (10 mg/ml) were extracted in a final concentration of 5M GuHCl overnight at 4° C. Samples were then diluted appropriately and run in duplicate on Aβ42-specific sandwich colorimetric ELISAs according to the manufacturer's protocol (Cat #298-92401, Wako Chemicals, Richmond, Va.). Optical densities at 450 nm were read on a Biotek plate reader (BioTek, USA) and Aβ42 concentration was determined by comparison with Aβ42 standard curves. Only readings in the linear range of the standard curve were included in analysis. Duplicates were averaged to determine concentration of Aβ42 in each sample. Finally, Aβ42 concentrations were normalized to total protein concentration and are reported as nanograms of Aβ42 per milligrams of total protein.

Immunohistochemistry and Plaque Quantification

At harvest, the half brain not used for fresh dissection was placed in 4% paraformaldehyde and kept at 4 C until further use. In order to minimize technical variation in immunohistochemistry, brains were sent to Neuroscience Associates (Knoxville, Tenn.), where 40 hemibrains were embedded, processed, and stained simultaneously. Briefly, the brains were freeze-sectioned coronally at 40 μm intervals (not including cerebellum) and staining for Aβ1-42 was performed on every $24^{th}$ section spaced at 960 μm, yielding approximately 9 sections per hemibrain. For analysis, images of each section containing hippocampus were collected on a Nikon Eclipse 90i microscope using NIS-Elements Advanced Research program. Images were taken using a 2× objective with computer automated focusing. Approximately 4 images were captured for each hemibrain and stitched together using NIS-Elements Advanced Research program. ImageJ particle analysis was used to automate detection of plaques (Hurtado et al., 2010). Regions of interest (hippocampus and cortex) in each image were manually outlined and pixel size of each region calculated and used to determine the percentage of each area covered by amyloid plaques, controlling for regional size differences.

Heritability Estimates

Heritability estimates for each phenotype (Table 1) were calculated according to established methods (Belknap, 1998). Briefly, we compared between-strain variance (due to genetic diversity, $V_G$) to total sample variance (due to both genetic and environmental factors, $V_E$) given the average number of biological replicates per strain (n) according to the following formula: $h^2_{RI\bar{x}} = V_G/(V_G+V_E/n)$. The average number of mice per strain was used to represent n and is reported in Table 1. $V_E$ was calculated by summing between-strain variance and within-strain variance, as within-strain variance should capture all variation not due to genetic diversity. As heritability was calculated using both males and females, within-strain variance will also capture variation due to sex. However, as we calculated heritability independently for each trait of interest across AD- and Ntg-BXDs, our heritability estimates do not capture variation due to age or genotype.

RNA Sequencing

Snap frozen hippocampi from AD-BXD strains and Ntg-BXD littermate controls at 6 m [AD-BXDs n=33 (15 females/18 males) across 13 strains, Ntg-BXDs n=31 (17 females/14 males) across 14 strains] and 14 m [AD-BXDs n=36 (16 female/20 male) across 14 strains, Ntg-BXDs n=33 (17 female/16 male) across 15 strains] were used for RNA sequencing. RNA was isolated on a Qiacube using the RNeasy mini kit (Qiagen) and treated with DNase to remove contaminating DNA. RNA quality was confirmed using a BioAnalyzer (Agilent Technologies). All samples had RNA Integrity Numbers (RIN values)>8.0. Sequencing libraries were prepared from 1 μg RNA with the Truseq Stranded mRNA Sample Preparation Kit (Illumina Inc) following the manufacturer's protocol. Final PCR-enriched fragments were validated on a 2200 Tapestation Instrument using the D1000 ScreenTape (Agilent Technologies) and quantified by qPCR using a Universal Library Quantification Kit (Kapa Biosystems) on the QuantStudio 6 Flex (ThermoFisher Scientific). Final library pools were sequenced by 75 bp paired-end sequencing on a HiSeq2500 (Illumina Inc). Because both C57BL/6J and DBA/2J alleles segregate within our panel, the GBRS/EMASE pipeline developed by the Churchill group at The Jackson Laboratory was used in order to align reads to a diploid transcriptome (emase.readthedocs.io/en/latest/). An expectation maximization algorithm was used in order to align reads to the correct allele, allowing for the quantification of both total reads assigned to a gene and the number of reads assigned to either the B or D allele. For final by-strain analysis, samples belonging to the same strain/sex/age/genotype group were averaged. Differential expression analysis was conducted using the DESeq2 package (Love et al., 2014). For evaluation of transgene expression and its effect on endogenous App and Psen1 expression, RNA-sequencing reads from a larger subset of AD- and Ntg-BXDs [n=293 (177 females/116 males across 28 strains)] were sequenced according to identical methods and were additionally aligned to the mutated human APP and PSEN1 sequences. Expression was quantified using transcripts per million and then log transformed to compare expression across groups.

Comparison of AD-BXD and Human Transcriptomes

In order to evaluate how well the AD-BXD transcript profile matches that of human AD, we utilized a dataset recently published by Hargis and Blalock (Hargis and Blalock, 2017) comparing existing mouse models of AD to human AD. They identified a consensus AD signature consisting of 60 genes derived from the top 10% commonly upregulated and downregulated genes across three human AD datasets (data not shown). In order to see how the transcriptome from our AD-BXD panel compared to normal expression patterns, differential expression analysis comparing hippocampal gene expression from 14 m AD-BXD lines to non-carrier littermate controls was performed using DESeq2 (Love et al., 2014). The $\log_2$ fold change (log 2FC) for each of the 60 AD consensus genes that were significantly differentially expressed (nominal p-value<0.05) across AD and Ntg-BXDs was identified and used for comparison across human and mouse datasets obtained from Hargis et. al. (Hargis and Blalock, 2017). To evaluate similarities between immune-enriched genes upregulated in AD-BXDs and gene lists identified as associated with AD from Zhang et. al. (Zhang et al., 2013) and Jones et. al. (International Genomics of Alzheimer's Disease, 2015), all three gene lists were uploaded into GeneWeaver (Baker et al., 2016) and Jaccardian similarity indexes were calculated and evaluated for significance.

Gene Set Enrichment Analysis

Gene set enrichment analysis (GSEA) was performed as previously described (Neuner et al., 2016; Subramanian et al., 2005). Briefly, significantly differentially expressed genes from the comparison of interest (data not shown) were ranked according to $\log_2$ fold change. Gene ontology (GO) gene sets were obtained from the Broad Institute's Molecular Signatures Database (MSigDB) (Liberzon et al., 2015) and ranked gene lists were tested for enrichment using GSEA's GSEAPreranked feature, version 3.0. To compare functional annotation enrichment among differentially expressed genes across AD and normal aging (FIG. 5), GO terms identified in each comparison (data not shown) were extracted from GSEA results. A score for enrichment strength was calculated by transforming the FDR q-values generated by GSEA using the following formula: $-\log_{10}$ (FDRq+0.001), similar to that described in (Raj et al., 2017). The values calculated in each scenario (AD and normal aging) were then plotted against each other in FIG. 5 to identify those pathways with stronger enrichment in AD than normal aging, and vice versa.

Calculation of a Genetic Risk Score

To evaluate whether the AD-BXD panel was sensitive to variation in known AD risk loci, we derived a genetic risk score for each strain, similar to that described by Chouraki and colleagues in 2016 (Chouraki et al., 2016). Strains were first stratified into impaired (below the AD-BXD population average) and unimpaired (above the AD-BXD population average) based on CFM performance at 6 m. We then identified the genotype of each strain at 21 genes known to contribute risk for AD and identified the risk allele of each gene (i.e. the allele that appeared more frequently in the impaired group, Table 2). Note as some genes appeared in the same linkage block, only 19 genotypes were used in the calculation of the GRS. The odds ratio for each gene was calculated and log transformed to determine an individual risk score per gene. These individual risk scores were used to derive an overall genetic risk score for each strain that reflected how many copies of each risk allele were present. Overall genetic risk scores were transformed based on previous methods (Chouraki et al., 2016) using the following formula: total risk score*(# of markers tested/sum of individual gene risk scores). The GRS was then correlated to cognitive traits as reported. To avoid influence from our original definition of 'impaired' versus 'unimpaired' using 6 m CFM, we correlated GRS to uncorrelated, independent cognitive tasks. As contextual fear conditioning is a cross-sectional task, and we wanted to investigate the extent to which these genes regulated cognitive decline, we focused on cognitive tasks from a separate cohort of aged AD-BXDs, particularly 14 m CFA. Finally, to empirically estimate the null distribution for the correlation of our genetic risk score and cognitive traits of interest, we randomly sampled 1000 sets of 19 markers across the genome and repeated the derivation of GRS. We created 1000 GRS from randomly sampled data, and correlated each random GRS to strain-matched cognitive performance, which illustrated the correlation between 14 m CFA and our derived GRS was stronger than the correlation observed for 95% of randomly sampled genes. As an additional control, we repeated the process but based on allelic distribution of risk alleles across Ntg-BXDs. We defined Ntg-BXD strains as 'impaired' vs 'unimpaired' based on 6 m CFM performance, identified the risk allele for each of the 21 genes listed in Table 2, calculated the odds ratio for each, and derived a Ntg-based GRS. This GRS showed no relationship with cognitive outcomes in either Ntg- or AD-BXDs, or any non-cognitive traits tested. Table 2, gene lengths were obtained using start and end positions listed in Ensembl version 92 and SNP counts were obtained from Sanger, release REL-1505 (Keane et al., 2011).

Quantification and Statistical Analysis

All experiments and data analysis were conducted with experimenters blind to strain background and genotype (5XFAD vs Ntg) where appropriate. Statistical analysis was performed using SPSS software Version 23 (IBM), R, and Excel. Distribution was evaluated for normality using Shipiro-Wilkes test. Additional analyses included independent unpaired t-tests, univariate ANOVAs, Pearson correlation, and Jaccard index to test similarity. Correction for multiple comparisons was also used where appropriate (i.e differential expression analysis). Data values reported in both the main text and figure legends are given as mean±standard error of the mean unless otherwise stated. Outliers were identified based on a pre-defined criteria of average values±3 SD outside the mean.

Data and Software Availability

Genotypes from the BXD strains are publically available on GeneNetwork.org. Raw phenotype data will be made available on GeneNetwork and/or via the Mouse Phenome Database. RNA-sequencing from the hippocampus of a subset of AD-BXD strains is available on Gene Expression Omnibus (GEO) under accession number GSE101144. Data will also be deposited in the AMP-AD Knowledge Portal (doi: 10.7303/syn17016211). EMASE software used for alignment of RNA sequencing reads to a diploid transcriptome is available online at: (emase.readthedocs.io/en/latest/).

REFERENCES

Altmann, A., Tian, L., Henderson, V. W., Greicius, M. D., and Alzheimer's Disease Neuroimaging Initiative, I. (2014). Sex modifies the APOE-related risk of developing Alzheimer disease. Annals of neurology 75, 563-573.

Baker, E., Bubier, J. A., Reynolds, T., Langston, M. A., and Chesler, E. J. (2016). GeneWeaver: data driven alignment of cross-species genomics in biology and disease. Nucleic acids research 44, D555-559.

Belknap, J. K. (1998). Effect of within-strain sample size on QTL detection and mapping using recombinant inbred mouse strains. Behavior genetics 28, 29-38.

Berchtold, N. C., Coleman, P. D., Cribbs, D. H., Rogers, J., Gillen, D. L., and Cotman, C. W. (2013). Synaptic genes are extensively downregulated across multiple brain regions in normal human aging and Alzheimer's disease. Neurobiology of aging 34, 1653-1661.

Blalock, E. M., Buechel, H. M., Popovic, J., Geddes, J. W., and Landfield, P. W. (2011). Microarray analyses of laser-captured hippocampus reveal distinct gray and white matter signatures associated with incipient Alzheimer's disease. Journal of chemical neuroanatomy 42, 118-126.

Blalock, E. M., Geddes, J. W., Chen, K. C., Porter, N. M., Markesbery, W. R., and Landfield, P. W. (2004). Incipient Alzheimer's disease: microarray correlation analyses reveal major transcriptional and tumor suppressor responses. Proceedings of the National Academy of Sciences of the United States of America 101, 2173-2178.

Brier, M. R., Gordon, B., Friedrichsen, K., McCarthy, J., Stern, A., Christensen, J., Owen, C., Aldea, P., Su, Y., Hassenstab, J., et al. (2016). Tau and Abeta imaging, CSF measures, and cognition in Alzheimer's disease. Science translational medicine 8, 338ra366.

Chouraki, V., Reitz, C., Maury, F., Bis, J. C., Bellenguez, C., Yu, L., Jakobsdottir, J., Mukherjee, S., Adams, H. H., Choi, S. H., et al. (2016). Evaluation of a Genetic Risk Score to Improve Risk Prediction for Alzheimer's Disease. Journal of Alzheimer's disease: JAD 53, 921-932.

Fanselow, M. S. (2000). Contextual fear, gestalt memories, and the hippocampus. Behavioural brain research 110, 73-81.

Gatz, M., Pedersen, N. L., Berg, S., Johansson, B., Johansson, K., Mortimer, J. A., Posner, S. F., Viitanen, M., Winblad, B., and Ahlbom, A. (1997). Heritability for Alzheimer's disease: the study of dementia in Swedish twins. The journals of gerontology Series A, Biological sciences and medical sciences 52, M117-125.

Hardy, J. A., and Higgins, G. A. (1992). Alzheimer's disease: the amyloid cascade hypothesis. Science 256, 184-185.

Hargis, K. E., and Blalock, E. M. (2017). Transcriptional signatures of brain aging and Alzheimer's disease: What are our rodent models telling us? Behavioural brain research 322, 311-328.

Hokama, M., Oka, S., Leon, J., Ninomiya, T., Honda, H., Sasaki, K., Iwaki, T., Ohara, T., Sasaki, T., LaFerla, F. M., et al. (2014). Altered expression of diabetes-related genes in Alzheimer's disease brains: the Hisayama study. Cerebral cortex 24, 2476-2488.

Hong, S., Beja-Glasser, V. F., Nfonoyim, B. M., Frouin, A., Li, S., Ramakrishnan, S., Merry, K. M., Shi, Q., Rosenthal, A., Barres, B. A., et al. (2016). Complement and microglia mediate early synapse loss in Alzheimer mouse models. Science 352, 712-716.

Hurtado, D. E., Molina-Porcel, L., Iba, M., Aboagye, A. K., Paul, S. M., Trojanowski, J. Q., and Lee, V. M. (2010). A{beta} accelerates the spatiotemporal progression of tau pathology and augments tau amyloidosis in an Alzheimer mouse model. The American journal of pathology 177, 1977-1988.

International Genomics of Alzheimer's Disease, C. (2015). Convergent genetic and expression data implicate immunity in Alzheimer's disease. Alzheimer's & dementia: the journal of the Alzheimer's Association 11, 658-671.

Jackson, H. M., Onos, K. D., Pepper, K. W., Graham, L. C., Akeson, E. C., Byers, C., Reinholdt, L. G., Frankel, W. N., and Howell, G. R. (2015). DBA/2J genetic background exacerbates spontaneous lethal seizures but lessens amyloid deposition in a mouse model of Alzheimer's disease. PLoS One 10, e0125897.

Kaczorowski, C. C., and Disterhoft, J. F. (2009). Memory deficits are associated with impaired ability to modulate neuronal excitability in middle-aged mice. Learning & memory 16, 362-366.

Kaczorowski, C. C., Sametsky, E., Shah, S., Vassar, R., and Disterhoft, J. F. (2011). Mechanisms underlying basal and learning-related intrinsic excitability in a mouse model of Alzheimer's disease. Neurobiology of aging 32, 1452-1465.

Karch, C. M., Jeng, A. T., Nowotny, P., Cady, J., Cruchaga, C., and Goate, A. M. (2012). Expression of novel Alzheimer's disease risk genes in control and Alzheimer's disease brains. PloS one 7, e50976.

Keane, T. M., Goodstadt, L., Danecek, P., White, M. A., Wong, K., Yalcin, B., Heger, A., Agam, A., Slater, G., Goodson, M., et al. (2011). Mouse genomic variation and its effect on phenotypes and gene regulation. Nature 477, 289-294.

Kitazawa, M., Medeiros, R., and Laferla, F. M. (2012). Transgenic mouse models of Alzheimer disease: developing a better model as a tool for therapeutic interventions. Current pharmaceutical design 18, 1131-1147.

Lambert, J. C., Ibrahim-Verbaas, C. A., Harold, D., Naj, A. C., Sims, R., Bellenguez, C., DeStafano, A. L., Bis, J. C., Beecham, G. W., Grenier-Boley, B., et al. (2013). Meta-analysis of 74,046 individuals identifies 11 new susceptibility loci for Alzheimer's disease. Nature genetics 45, 1452-1458.

Liao, F., Zhang, T. J., Jiang, H., Lefton, K. B., Robinson, G. O., Vassar, R., Sullivan, P. M., and Holtzman, D. M. (2015). Murine versus human apolipoprotein E4: differential facilitation of and co-localization in cerebral amyloid angiopathy and amyloid plaques in APP transgenic mouse models. Acta neuropathologica communications 3, 70.

Liberzon, A., Birger, C., Thorvaldsdottir, H., Ghandi, M., Mesirov, J. P., and Tamayo, P. (2015). The Molecular Signatures Database (MSigDB) hallmark gene set collection. Cell systems 1, 417-425.

Love, M. I., Huber, W., and Anders, S. (2014). Moderated estimation of fold change and dispersion for RNA-seq data with DESeq2. Genome biology 15, 550.

Mahley, R. W., Weisgraber, K. H., and Huang, Y. (2009). Apolipoprotein E: structure determines function, from atherosclerosis to Alzheimer's disease to AIDS. Journal of lipid research 50 Suppl, S183-188.

Mielke, M. M., Vemuri, P., and Rocca, W. A. (2014). Clinical epidemiology of Alzheimer's disease: assessing sex and gender differences. Clin Epidemiol 6, 37-48.

Neuner, S. M., Garfinkel, B. P., Wilmott, L. A., Ignatowska-Jankowska, B. M., Citri, A., Orly, J., Lu, L., Overall, R. W., Mulligan, M. K., Kempermann, G., et al. (2016). Systems genetics identifies Hp1bp3 as a novel modulator of cognitive aging. Neurobiology of aging 46, 58-67.

Neuner, S. M., Wilmott, L. A., Hope, K. A., Hoffmann, B., Chong, J. A., Abramowitz, J., Birnbaumer, L., O'Connell, K. M., Tryba, A. K., Greene, A. S., et al. (2015). TRPC3 channels critically regulate hippocampal excitability and contextual fear memory. Behavioural brain research 281, 69-77.

Oakley, H., Cole, S. L., Logan, S., Maus, E., Shao, P., Craft, J., Guillozet-Bongaarts, A., Ohno, M., Disterhoft, J., Van Eldik, L., et al. (2006). Intraneuronal beta-amyloid aggregates, neurodegeneration, and neuron loss in transgenic mice with five familial Alzheimer's disease mutations: potential factors in amyloid plaque formation. The Journal of neuroscience: the official journal of the Society for Neuroscience 26, 10129-10140.

Ohno, M. (2009). Failures to reconsolidate memory in a mouse model of Alzheimer's disease. Neurobiology of learning and memory 92, 455-459.

Onos, K. D., Sukoff Rizzo, S. J., Howell, G. R., and Sasner, M. (2016). Toward more predictive genetic mouse models of Alzheimer's disease. Brain research bulletin 122, 1-11.

Peirce, J. L., Lu, L., Gu, J., Silver, L. M., and Williams, R. W. (2004). A new set of BXD recombinant inbred lines from advanced intercross populations in mice. BMC genetics 5, 7.

Piccio, L., Deming, Y., Del-Aguila, J. L., Ghezzi, L., Holtzman, D. M., Fagan, A. M., Fenoglio, C., Galimberti, D., Borroni, B., and Cruchaga, C. (2016). Cerebrospinal fluid soluble TREM2 is higher in Alzheimer disease and associated with mutation status. Acta neuropathologica 131, 925-933.

Raj, T., Chibnik, L. B., McCabe, C., Wong, A., Replogle, J. M., Yu, L., Gao, S., Unverzagt, F. W., Stranger, B., Murrell, J., et al. (2017). Genetic architecture of age-related cognitive decline in African Americans. Neurology Genetics 3, e125.

Ridge, P. G., Mukherjee, S., Crane, P. K., Kauwe, J. S., and Alzheimer's Disease Genetics, C. (2013). Alzheimer's disease: analyzing the missing heritability. PloS one 8, e79771.

Ryman, D., Gao, Y., and Lamb, B. T. (2008). Genetic loci modulating amyloid-beta levels in a mouse model of Alzheimer's disease. Neurobiology of aging 29, 1190-1198.

Ryman, D. C., Acosta-Baena, N., Aisen, P. S., Bird, T., Danek, A., Fox, N. C., Goate, A., Frommelt, P., Ghetti, B., Langbaum, J. B., et al. (2014). Symptom onset in autosomal dominant Alzheimer disease: a systematic review and meta-analysis. Neurology 83, 253-260.

Sadleir, K. R., Eimer, W. A., Cole, S. L., and Vassar, R. (2015). Abeta reduction in BACE1 heterozygous null 5XFAD mice is associated with transgenic APP level. Molecular neurodegeneration 10, 1.

Sebastiani, G., Krzywkowski, P., Dudal, S., Yu, M., Paquette, J., Malo, D., Gervais, F., and Tremblay, P. (2006). Mapping genetic modulators of amyloid plaque deposition in TgCRND8 transgenic mice. Human molecular genetics 15, 2313-2323.

Selkoe, D. J. (1991). The molecular pathology of Alzheimer's disease. Neuron 6, 487-498.

Sipe, J. D., Carreras, I., Gonnerman, W. A., Cathcart, E. S., de Beer, M. C., and de Beer, F. C. (1993). Characterization of the inbred CE/J mouse strain as amyloid resistant. The American journal of pathology 143, 1480-1485.

Sittig, L. J., Carbonetto, P., Engel, K. A., Krauss, K. S., Barrios-Camacho, C. M., and Palmer, A. A. (2016). Genetic Background Limits Generalizability of Genotype-Phenotype Relationships. Neuron 91, 1253-1259.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Taylor, B. A., Wnek, C., Kotlus, B. S., Roemer, N., MacTaggart, T., and Phillips, S. J. (1999). Genotyping new BXD recombinant inbred mouse strains and comparison of BXD and consensus maps. Mamm Genome 10, 335-348.

Wang, X., Pandey, A. K., Mulligan, M. K., Williams, E. G., Mozhui, K., Li, Z., Jovaisaite, V., Quarles, L. D., Xiao, Z., Huang, J., et al. (2016). Joint mouse-human phenome-wide association to test gene function and disease risk. Nat Commun 7, 10464.

Zerbino, D. R., Achuthan, P., Akanni, W., Amode, M. R., Barrell, D., Bhai, J., Billis, K., Cummins, C., Gall, A., Giron, C. G., et al. (2018). Ensembl 2018. Nucleic acids research 46, D754-D761.

Zhang, B., Gaiteri, C., Bodea, L. G., Wang, Z., McElwee, J., Podtelezhnikov, A. A., Zhang, C., Xie, T., Tran, L., Dobrin, R., et al. (2013). Integrated systems approach identifies genetic nodes and networks in late-onset Alzheimer's disease. Cell 153, 707-720.

Zokaei, N., Giehl, K., Sillence, A., Neville, M. J., Karpe, F., Nobre, A. C., and Husain, M. (2017). Sex and APOE: A memory advantage in male APOE epsilon4 carriers in midlife. Cortex; a journal devoted to the study of the nervous system and behavior 88, 98-105.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method, comprising delivering to a subject having or at risk of Alzheimer's disease (AD) a ribonucleic acid (RNA) that binds to nucleic acid encoding transient receptor potential cation channel subfamily C, member 3 (TRPC3) to reduce expression of TRPC3 and beta-amyloid plaques in the subject relative to a control.

2. The method of claim 1, wherein the subject is a human subject.

3. The method of claim 1, wherein delivery of the RNA alleviates one or more symptoms of AD and/or slow or stop progression of AD.

4. The method of claim 1, wherein delivery of the RNA improves working memory performance at least 10% compared to the subject's working memory performance prior to delivery of the agent and/or reduces the amount of beta-amyloid plaque by at least 40% compared to the amount of beta-amyloid plaque prior to delivery of the agent.

5. The method of claim 1, wherein the TRPC3 comprises an amino acid sequence of any one of SEQ ID NOS: 1-3.

6. The method of claim 1, wherein the TRPC3 is encoded by a nucleic acid sequence of any one of SEQ ID NOS: 4-6.

7. The method of claim 1, wherein the RNA is a guide RNA (gRNA).

8. The method of claim 7, wherein the gRNA is delivered to the subject with a Cas enzyme.

9. The method of claim 1, wherein the RNA is an RNA interference (RNAi) molecule.

10. The method of claim 9, wherein the RNA interference molecule is a small interfering RNA (siRNA).

11. The method of claim 9, wherein the RNA interference molecule is a short hairpin RNA (shRNA).

12. The method of claim 9, wherein the RNA interference molecule is a micro RNA (miRNA).

* * * * *